US006159693A

United States Patent [19]
Shultz et al.

[11] Patent Number: 6,159,693
[45] Date of Patent: Dec. 12, 2000

[54] NUCLEIC ACID DETECTION

[75] Inventors: John W. Shultz, Verona; Michelle A. Mandrekar, Fitchburg; Donna M. Leippe; Martin K. Lewis, both of Madison; Lisa S. Nelson, DeForest, all of Wis.

[73] Assignee: Promega Corporation, Madison, Wis.

[21] Appl. No.: 09/252,436

[22] Filed: Feb. 18, 1999

Related U.S. Application Data

[63] Continuation-in-part of application No. 09/042,287, Mar. 13, 1998.

[51] Int. Cl.$^7$ .......................... C12Q 1/68; G01N 33/53; G01N 33/566; C07H 19/04
[52] U.S. Cl. ................... 435/6; 435/7; 435/17; 435/21; 435/810; 436/501; 536/26; 536/27; 536/28; 935/77; 935/82
[58] Field of Search .............. 435/6, 7, 17, 21, 435/810; 436/501; 536/26, 27, 28; 935/77, 82

[56] References Cited

U.S. PATENT DOCUMENTS

| | | | |
|---|---|---|---|
| 4,446,231 | 5/1984 | Self | 435/7 |
| 4,460,684 | 7/1984 | Bauer | 435/14 |
| 4,595,655 | 6/1986 | Self | 435/7 |
| 4,735,897 | 4/1988 | Vary et al. | 435/6 |
| 4,743,561 | 5/1988 | Shaffar | 436/501 |
| 4,755,458 | 7/1988 | Rabbani et al. | 435/5 |
| 5,498,523 | 3/1996 | Tabor et al. | 435/6 |
| 5,541,311 | 7/1996 | Dahlberg et al. | 536/23.7 |
| 5,648,232 | 7/1997 | Squirrell | 435/34 |

FOREIGN PATENT DOCUMENTS

| | | | |
|---|---|---|---|
| 2055200 | 12/1981 | United Kingdom | G01N 21/76 |
| WO 94/25619 | 11/1994 | WIPO | C12Q 1/00 |
| WO 98/13523 | 4/1998 | WIPO | C12Q 1/68 |
| WO 98/28440 | 7/1998 | WIPO | C12Q 1/68 |

OTHER PUBLICATIONS

Nikiforov et al., "Genetic Bit Analysis: a solid phase method for typing single nucleotide polymorphisms", Nucleic Acids Research, (Sep. 1994), vol. 22(20), pp. 4167–4175.

A.E. Sippel, "Purification and Characterization of Adenosine Triphosphate: Ribonucleic Acid Adenyltransferase from *Escherichia coli*" *Eur. J. Biochem.* 37:31–40 (1973).

K.Chowdhury, N. Kaushik, V.N. Pandey and M.J. Modak, "Elucidiation of the Role of Arg 110 of Murine Leukemia Virus Reverse Transcriptase in the Catalytic Mechanism: Biochemical Characterization of Its Mutant Enzymes," *Biochemistry*, 35:16610–16620 (1996).

S. Karamohamed, M. Ronaghi and P. Nyren, "Biolumino-metric Method for Real–Time Detection of Reverse Transcriptase Activity", *Biotechniques*, 24:302–306 (Feb., 1998).

B. Hove–Jensen, K.W. Harlow, C.J. King, R.L. Switzer, "Phosphoribosylpyrophosphate Synthetase of *Escherichia coli*" *J. Biol. Chem.*, 261(15):6765–6771 (1986).

P. Nyren, S. Karamohamed and M. Ronaghi, "Detection of Single–Base Changes Using a Bioluminometric Primer Extension Assay", *Anal. Biochem.*, 244:367–373 (Jan. 15, 1997).

M. Ronaghi, S. Karamohamed, B. Pettersson, M. Uhlen and P. Nyren, "Real–Time DNA Sequencing Using Detection of Pyrophosphate Release," *Anal. Biochem.*, 242:84–89 (1996).

T.A. Rozovskaya, V.O. Rechinsky, R.S. Bibilashvili, M.Y. Karpeisky, N.B. Tarusova, R.M. Khomutov, H.B.F. Dixon, "The Mechanism of Pyrophosphorolysis of RNA by RNA Polymerase", *Biochem. J.*, 224:645–650 (1989).

M.P. Deutscher and A. Kornberg, "Enzymatic Synthesis of Deoxyribonucleic Acid", *J. Biol. Chem.*, 244(11):3019–28 (1969).

J.D. Moyer and J.F. Henderson, "Nucleoside Triphosphate Specificity of Firefly Luciferase", *Anal. Biochem.*, 131:187–189 (1983).

C. Blondin, L. Serina, L. Weismuller, A. Gilles and O. Barzu, "Improved Spectrophotometric Assay of Nucleoside Monophosphate Kinase Activity Using the Pyruvate Kinase/Lactate Dehydrogenase Coupling System", *Anal. Biochem.*, 220:219–21 (1994).

S. Tabor and C.C. Richardson, "DNA Sequence Analysis With a Modified Bacteriophage T7 DNA Polymerase", *J. Biol. Chem.*, 265(14):8322–8328 (1990).

R.S. Chittock, J.–M. Hawronsky, J. Holah and C.W. Wharton, "Kinetic Aspects of ATP Amplification Reactions", *Anal. Biochem.*, 255:120–126 (Jan. 1, 1998).

Kung, et al., "Picogram Quantitation of Total DNA Using DNA–Binding Proteins in a Silicon Sensor–Based System", *Anal. Biochem.*, 187:220–227 (1990).

Srivastavan & Modak, *J. Biol. Chem.*, 255(5):2000–2004 (1980).

Sano & Feix, *Eur. J. Biochem.*, 71:577–583 (1976).

Sabina, et al., *Science*, 223:1193–1195 (1984).

Parks & Agarwal in *The Enzymes*, vol. 9:307–333, P. Boyer Ed. (1973).

Shimofuruya & Suzuki, *Biochem. Intl.*, 26(5):853–861 (1992).

(List continued on next page.)

*Primary Examiner*—Jeffrey Fredman
*Assistant Examiner*—Arun Chakrabarti
*Attorney, Agent, or Firm*—Welsh & Katz, Ltd.

[57] ABSTRACT

This invention discloses methods for detecting specific nucleic acid sequences, interrogating the identity of a specific base within a sequence, and assaying endonuclease and exonuclease activity. DNA or RNA probes are hybridized to target nucleic acid sequences. Probes that are complementary to the target sequence at each base are depolymerized, while probes which differ from the target at the interrogation position are not depolymerized. The nucleic acid detection systems utilize the pyrophosphorolysis reaction catalyzed by various polymerases to produce deoxyribonucleoside triphosphates or ribonucleoside triphosphates. dNTPs are transformed to ATP by the action of NDPK. The ATP produced by these reactions is detected by luciferase or NADH based detection systems.

33 Claims, No Drawings

OTHER PUBLICATIONS

Nyren, et al., "Detection of Single–Base Changes Using a Bioluminometric Primer Extension Assay", *Anal. Biochem.*, 244:367–373 (1997).

P. Bernard et al., *Am. J. Pathol.*, 153:1055–1061 (1998).

G. Garinis et al., *J. Clin. Lab. Anal.*, 13:122–125 (1999).

Holguin, et al., *Eur. J. Clin. Microbiol. Infect. Dis.*, 18:256–259 (1999).

Boriskin, et al., *Arch. Dis. Child.*, 80:132–136 (1999).

de Vega, et al., "Primer Terminus Stabilizing at the 3'–5' exonuclease active site of _29 DNA polymerase. Involvement of two amino acid residues highly conserved in proofreading DNA polymerases", *EMBO J.*, 15(5):1182–1192 (1996).

S. Patel et al., *Biochemistry*, 30:511–525 (1991).

I. Wong et al., *Biochemistry*, 30:526–537 (1991).

S. Zinnen et al., *J. Biological Chemistry*, 269(39):24195–24202 (1994).

J. Lindquist, Dept. of Bacteriology, University of Wisconsin–Madison, http://www.bact.wisc.edu/bact102/102di13.html (Undated).

J. Lindquist, Dept. of Bacteriology, University of Wisconsin–Madison, http://www.bact.wisc.edu/bact102/102di13a.html (Undated).

Most Probable Number (MPN), WQA Glossary of Terms, 3rd Ed., Water Quality Association (Undated).

P. Nyren, B. Pettersson, and M. Uhlen. "Solid Phase DNA Minisquencing byan Enzymatic Luminometric Inorganic Pyrophosphate Detection Assay," *Anal. Biochem..*, 208:171–175 (1993).

M. Ronaghi, S. Karamohamed, B. Pettersson, M. Uhlen, and P. Nyren, "Real–Time DNA Sequencing Using Detection of Pyrophosphate Release," *Anal. Biochem.*, 242:84–89 (1996).

J. Shultz, D. Leippe, K. Lewis and M. Nelson, "Non–radioactive Measurement of DNA Using Coupled Enzymatic Reactions", Presentation, Mar. 16–20, 1998 at a Parenteral Drug Association meeting in San Francisco, California.

NUCLEIC ACID DETECTION

CROSS REFERENCE TO RELATED APPLICATION

This application is a continuation-in-part of U.S. Ser. No. 09/042,287, filed Mar. 13, 1998, and incorporated herein by reference.

FIELD OF THE INVENTION

The present invention relates to the field of molecular biology, and in particular to the detection of nucleic acids and cells. The present invention methods and compositions for detection of extremely low amounts of nucleic acids, specific nucleic acids, specific nucleotide sequences and cellular materials.

BACKGROUND OF THE INVENTION

Methods for producing large amounts of recombinant protein are well known. As the recombinant protein industry has developed, the need for various quality control assays has arisen. An example is the need for the quantitation of nucleic acids present in recombinant protein preparations. Current FDA guidelines require that the amount of nucleic acid present in recombinant therapeutic proteins be less than 10 pg of DNA per daily dose of recombinant protein. Therefore, methods for detecting extremely low amounts of nucleic acids are needed. Such methods can also find widespread use for the quantitation of nucleic acid in forensic, clinical and agricultural samples.

Several methods of detecting low levels of nucleic acid have been described. One method is based on classical hybridization techniques. This method utilizes radiolabeled nucleic acid probes which bind to the nucleic acid of interest. However, this method has several disadvantages, including poor reproducibility, generation of large amounts of radioactive waste reagent, and high background levels caused by nonspecific binding. Furthermore, this technique is generally inappropriate for determining the presence of low amounts of nucleic acid of unknown sequence.

A second method of detecting nucleic acid utilizes fluorescent dyes capable of intercalating into nucleic acids. However, many interfering substances such as detergents, proteins, and lipids affect the reproducibility of the signal generated by this method.

A third method of detecting low levels of DNA utilizes biotinylated single-stranded DNA binding protein (SSB), streptavidin, an anti-DNA antibody fused to urease, and biotinylated nitrocellulose as reagents. This assay is commercially available from Molecular Devices (Sunnyvale, Calif.) and described in Kung et al., Anal. Biochem., 187:220–27 (1990). The assay is performed by incubating the streptavidin, biotin-SSB, and the anti-DNA antibody together, permitting a complex to be formed. The complex is then captured on the biotinylated membrane, washed, and the amount of captured urease is determined. This method is highly sensitive but has several disadvantages, including costly reagents and the need for extensive controls.

A fourth method takes advantage of depolymerization by polymerases. Polynucleotide polymerases are responsible for the synthesis of nucleic acids in cells. The reverse of this reaction, the depolymerization of nucleic acid, can also occur in the presence of phosphate (phosphorolysis) or pyrophosphate (pyrophosphorolysis). Enzymes reported to carry out pyrophosphorolysis include E. coli DNA Polymerase (Deutscher and Kornberg, J. Biol. Chem., 244(11) :3019–28 (1969)), T7 DNA Polymerase (Wong et al., Biochemistry 30:526–37 (1991); Tabor and Richardson, J. Biol. Chem. 265: 8322–28 (1990)), E. coli RNA polymerase (Rozovskaya et al., Biochem. J. 224:645–50 (1994)), AMV and RLV reverse transcriptases (Srivastava and Modak, J. Biol. Chem. 255: 2000–4 (1980)), and HIV reverse transcriptase (Zinnen et al., J. Biol. Chem. 269:24195–202 (1994)).

U.S. Pat. No. 4,735,897 describes a method of detecting polyadenylated messenger RNA (poly(A) mRNA). Depolymerization of poly(A) mRNA in the presence of phosphate has been shown to result in the formation of ADP, which can be converted by pyruvate kinase or creatine phosphokinase into ATP. RNA may also be digested by a ribonuclease to AMP, converted to ADP by adenylate kinase, and then converted to ATP by pyruvate kinase. The ATP so produced is detected by a luciferase detection system. In the presence of ATP and oxygen, luciferase catalyzes the oxidation of luciferin, producing light which can then be quantitated using a luminometer. Additional products of the reaction are AMP, pyrophosphate and oxyluciferin.

The presence of ATP-generating enzymes in all organisms also allows the use of a luciferase system for detecting the presence or amounts of contaminating cells in a sample, as described in U.S. Pat. No. 5,648,232. For example, ADP may be added to a sample suspected of containing contaminating cells. The ADP is converted by cellular enzymes into ATP which is detected by a luciferase assay, as described above. A major disadvantage of this method is the relative instability of the ADP substrate.

The polymerase chain reaction (PCR) is a well known method for detecting specific nucleic acids. In PCR, two primers are utilized, one that hybridizes to the sense strand of a DNA target and one that hybridizes to the antisense strand of the DNA target. The DNA is denatured by heating to yield single strands and the primers permitted to hybridize to the respective strands. A polymerase and dNTPs are then used to synthesize new DNA strands based on the sequence of the target strands and extended from the primers. Repeated cycles result in the amplification of a DNA product bounded at its 5' and 3' ends by the two primers. PCR is extremely sensitive, but contamination from previously amplified product can limit its usefulness in clinical applications. Also, it is of limited use for the detection of nucleic acid of unknown sequence.

What is needed in the art are reliable, cost-effective methods of detecting extremely low levels of nucleic acids, specific nucleic acids, cells, and cellular material in a wide variety of samples.

SUMMARY OF THE INVENTION

A need exists for quality control assays for proteins produced by recombinant methods. Current FDA guidelines suggest that preparations of recombinant protein should contain less than 10 pg of nucleic acid. There is also a need to be able to quantitate extremely low levels of nucleic acids in forensic samples. Therefore, it is an object of the present invention to provide methods for detecting low amounts of nucleic acids and low numbers of cells or cellular material. It is also an object of the invention to provide compositions for the detection of nucleic acids and kits for the detection of nucleic acids.

The present invention discloses novel methods for detecting low quantities of DNA, RNA and cells. These methods take advantage of novel combinations and optimization of the following reactions: pyrophosphorolysis or enzymatic degradation of nucleic acids; conversion of dNTPs to ATP; the conversion of AMP directly to ATP; amplification of ATP to increase sensitivity; and depolymerization of oligonucleotide probes.

In one embodiment of the present invention, methods are provided for detecting DNA in a reaction containing pyrophosphate, ADP, or a combination thereof. In some embodiments, the method comprises depolymerizing the nucleic acid (NA) at a terminal nucleotide by enzymatically cleaving the terminal internucleoside phosphodiester bond in the presence of pyrophosphate to form a dNTP according to the following reaction:

$$DNA_n + PP_i \rightarrow DNA_{n-1} + dNTP$$

catalyzed by a template-dependent polymerase, such as a DNA polymerase or reverse transcriptase including, but not limited to, T4 DNA polymerase, Taq polymerase, Tne DNA polymerase, *E. coli* DNA polymerase I, Klenow fragment of DNA polymerase I, Klenow exo minus, AMV reverse transcriptase, and MMLV reverse transcriptase. In some embodiments (e.g., quantitative assays for nucleic acids), the depolymerizing step is repeated essentially to completion or equilibrium to obtain at least two nucleoside triphosphate molecules from a strand of minimally three nucleotides. In alternative embodiments, (e.g., qualitative detection of DNA), the depolymerizing step need not be repeated if there are sufficient nucleic acid molecules present to generate a signal. In further embodiments, a subsequent step involves enzymatically transferring terminal 5' phosphate groups from the dNTP molecules to an ADP molecule to form ATP according to the following reaction:

$$dNTP^* + ADP \rightarrow dNDP + ATP^*$$

catalyzed by nucleoside diphosphate kinase (NDPK) and wherein P* is the terminal 5' phosphate so transferred. In some preferred embodiments, the final step is the detection of the ATP, either by a luciferase detection system or a NADH detection system. The depolymerizing step and phosphate transferring step are optionally performed in a single pot reaction. In particularly preferred embodiments where greater sensitivity is desired, the ATP molecules produced by the phosphate transferring step or the dNTPs produced by the depolymerizing step are amplified to form a plurality of ATP molecules.

The present invention also provides methods for detecting poly(A) mRNA in a reaction containing pyrophosphate. In some embodiments, the poly(A) mRNA is first depolymerized at a terminal nucleotide by enzymatically cleaving the terminal internucleoside phosphodiester bond in the presence of pyrophosphate to form a free ATP molecule according to the following reaction:

$$NA_n + PP_i \rightarrow NA_{n-1} + ATP$$

catalyzed by poly(A) polymerase. In alternative embodiments such as quantitative assays for RNA, the depolymerizing step is repeated essentially to completion or equilibrium, to provide at least two nucleoside triphosphate molecules from a strand of minimally three nucleotides. In other alternative embodiments such as for qualitative detection of RNA, the depolymerizing step need not be repeated if there are sufficient nucleic acid molecules present to generate a signal. In preferred embodiments, the ATP molecules so formed are then detected with either a luciferase detection system or a NADH detection system. In particularly preferred embodiments, the reaction sensitivity is increased by optionally amplifying the ATP molecules.

The present invention also provides methods for selectively detecting poly(A) mRNA in a reaction containing pyrophosphate, or ADP, or a combination thereof. In one embodiment, a complementary oligo(dT) probe is hybridized to poly(A) mRNA to form an RNA-DNA hybrid. In further embodiments, the oligo(dT) strand of the RNA-DNA hybrid is then depolymerized at the terminal nucleotide by enzymatically cleaving the terminal internucleoside phosphodiester bond in the presence of pyrophosphate to form dTTP, according to the following reaction:

$$TT_n + PP_i \rightarrow TT_{n-1} + dTTP$$

catalyzed by a reverse transcriptase or a polymerase with reverse transcriptase activity. In alternative embodiments such as quantitative assays for nucleic acids, the depolymerizing step is repeated essentially to completion or equilibrium to obtain at least two nucleoside triphosphate molecules from a strand of minimally three nucleotides. In other alternative embodiments such as qualitative detection of RNA, the depolymerizing step need not be repeated if there are sufficient nucleic acid molecules present to generate a signal. In some preferred embodiments, the phosphate groups from the dTTP are enzymatically transferred to ADP molecules to form ATP molecules according to the following reaction:

$$dTTP^* + ADP \rightarrow dTDP + ATP^*$$

catalyzed by NDPK, wherein P* is the terminal 5' phosphate so transferred. In preferred embodiments, the ATP so formed is detected by a luciferase detection system or NADH detection system. In particularly preferred embodiments where increased sensitivity is desired, the terminal phosphate of the dTTP is transferred to ADP to form ATP as above followed by an amplification of the resulting ATP.

In other embodiments, the present invention also provides methods for detection of DNA in a reaction containing PRPP, ADP, or a combination thereof. In one embodiment, free dNMP molecules are produced from the nucleic acid by digestion with a nuclease that releases a nucleotide with a 5' phosphate. In other embodiments, a pyrophosphate group is then enzymatically transferred from PRPP molecules to the dAMP molecules to form dATP molecules according to the following reaction:

$$dAMP + PRPP \rightarrow dATP + ribose-5'-PO_4$$

catalyzed by PRPP synthetase. In another embodiment, the terminal 5' phosphate groups from the dATP molecules are enzymatically transferred to ADP molecules to form ATP molecules according to the following reaction:

$$dATP^* + ADP \rightarrow dADP + ATP^*$$

catalyzed by NDPK wherein P* is the terminal 5' phosphate so transferred. In particularly preferred embodiments, the ATP so produced is detected by a luciferase detection system or a NADH detection system. In still another embodiment of the present invention, the pyrophosphate transferring step and the phosphate transferring step are performed in a single pot reaction. In other preferred embodiments, if increased sensitivity is required, the ATP molecules are amplified.

In yet other embodiments, the present invention provides methods of detecting RNA in a reaction containing PRPP. In preferred embodiments of the invention, free NMP molecules such as AMP are produced by digestion of RNA with a nuclease. In other embodiments, a pyrophosphate molecule from PRPP molecules is enzymatically transferred to the NMP molecules to form NTP molecules such as ATP according to the following reaction:

$$NMP+PRPP \rightarrow NTP+ribose\text{-}5'\text{-}PO_4$$

catalyzed by PRPP synthetase. In particularly preferred embodiments, the ATP so produced is then detected by a luciferase detection system or an NADH detection system. In other embodiments, if increased sensitivity is required, the ATP so produced is amplified.

In another embodiment, the present invention provides methods for determining the presence and/or amount of cells and cellular material present in the sample. In some embodiments of this invention, the contents of cells are released to form a cell lysate. In other embodiments, phosphate donor molecules (D-P) and AMP molecules are then added to the cell lysate so that ADP molecules are produced by the enzymatic transfer of a phosphate group from the donor to the AMP according to the following reaction:

$$D\text{-}P+AMP \rightarrow D+ADP$$

catalyzed by endogenous enzymes present in the cell lysate. In preferred embodiments, the ATP is then produced by the enzymatic transfer of a phosphate from the donor molecules to adenosine 5'-diphosphate molecules according to the following reaction:

$$D\text{-}P+ADP \rightarrow D+ATP$$

also catalyzed by endogenous enzymes present in the cell lysate sample. In particularly preferred embodiments, the ATP so produced is then detected by either a luciferase detection system or NADH detection system. The phosphate donor of this embodiment can be either dCTP, dGTP, or dTTP.

In other embodiments of the present invention, there are provided compositions for producing ATP from DNA, pyrophosphate, and ADP. In preferred embodiments, this composition comprises a mixture of NDPK and a nucleic acid polymerase that is provided at a concentration sufficient to catalyze the production of ATP from about picogram to microgram amounts of DNA.

In still other embodiments, the present invention also provides compositions for producing ATP from DNA, PRPP, and ADP. In a preferred embodiment, this composition comprises a mixture of a PRPP synthetase and NDPK in sufficient concentration to catalyze the production of ATP from about picogram to microgram amounts of DNA.

In another embodiment, the present invention provides various kits for nucleic acid detection. In one embodiment, a kit is provided that contains reagents for the detection of DNA or RNA by pyrophosphorolysis. In another embodiment, the kit contains a vessel containing a nucleic acid polymerase and a vessel containing a NDPK. In a preferred embodiment, the nucleic acid polymerase and NDPK are provided in the same container. In another embodiment, a kit is provided that contains reagents for the detection of nucleic acid by nuclease digestion. In some embodiments, the kit contains a vessel containing PRPP synthetase and a vessel containing a nuclease. In other embodiments, a kit is provided that contains reagents for the detection of RNA by pyrophosphorolysis. In other embodiments, the kit contains a vessel containing poly(A) polymerase. In still other embodiments, a kit containing reagents for the detection of DNA by nuclease digestion is provided. In one embodiment, this kit contains a vessel containing PRPP synthetase and a vessel containing nucleo- side diphosphate kinase. In other embodiments, the PRPP synthetase and NDPK are optionally provided in the same container. In some embodiments, the kits contain written instructions for use.

In still further embodiments of the present invention, the kits described above can contain primers or probes for primer-mediated specific nucleic acid detection. In some embodiments, the kit contains at least one nucleic acid probe for detection of a nucleic acid of interest. In other embodiments, the kits contain multiple nucleic acid probes, each of which can contain a different base at at least one interrogation position. In other embodiments, the kits contain multiple probes to nucleic acids from different species or alleles or which are useful for detecting point mutations or deletion or insertion mutations. In each of the particularly preferred embodiments, the kits contain instructions for use in interrogating the identity of a specific base within a nucleic acid, for discriminating between two homologous nucleic acids that differ by one or more base pairs, and for determining whether a nucleic acid contains a deletion or insertion mutation.

An embodiment of the present invention further provides a kit containing reagents for the detection of cells and/or cellular material in a sample. In some embodiments, the kit contains a vessel containing AMP and a vessel containing a high energy phosphate donor that is not utilized by luciferase. In other embodiments, the kits contain written instructions for use.

The present invention also provide methods for amplifying a nucleoside triphosphate molecule in a reaction containing adenosine 5'-monophosphate molecules, high energy phosphate donor molecules, or a combination thereof. In some embodiments, the terminal 5' phosphate group from a nucleoside triphosphate molecule (XTP) present in the sample is enzymatically transferred to an AMP molecule added to the sample to form ADP molecules and nucleoside diphosphate molecules (XDP, either a ribonucleoside or deoxyribonucleoside diphosphate) according to the following reaction:

$$XTP+AMP \rightarrow XDP+ADP$$

catalyzed by a first enzyme that can be either nucleoside monophosphate kinase or adenylate kinase. In other embodiments, a phosphate from a high energy phosphate donor molecule (D-P) that can not be utilized by the first enzyme is enzymatically transferred to the adenosine 5'-diphosphate molecules to form adenosine 5'-triphosphate molecules according to the following reaction:

$$ADP+D\text{-}P \rightarrow ATP+D$$

catalyzed by NDPK or pyruvate kinase. These two steps are then repeated until the desired level of amplification is achieved. In preferred embodiments, the high energy phosphate donors are selected from dCTP or AMP-CPP for NDPK, and PEP for pyruvate kinase.

In yet another embodiment, the present invention also provide methods for detecting DNA or RNA in a reaction containing pyrophosphate, or AMP, or a high energy phosphate donor, or a combination thereof, in a single pot reaction. In one embodiment, nucleic acid is depolymerized at a terminal nucleotide by enzymatically cleaving the terminal internucleoside phosphodiester bond in the presence of a pyrophosphate molecule to form a free ribonucleoside or deoxynucleoside triphosphate molecule (XTP) according to reaction 1 as follows:

Reaction 1: $NA_n+PP_i \rightarrow NA_{n-1}+XTP$ catalyzed by a polymerase. In other embodiments, the depolymerizing step is repeated to obtain at least two nucleoside triphosphate molecules. In some embodiments, the XTP molecules are then amplified by enzymatically transferring the terminal 5'phosphate group from the XTP molecule formed in reaction 1 to an AMP to produce an ADP molecule and a nucleoside 5'-diphosphate molecule (XDP) according to reaction 2 catalyzed by a first enzyme:

Reaction 2: XTP+AMP→XDP+ADP.

In other embodiments, a phosphate group from a high energy phosphate donor molecule, which is not a substrate for the first enzyme, is enzymatically transferred to the ADP molecules produced in reaction 2 to produce ATP molecules according to reaction 3 catalyzed by a second phosphotransferase enzyme:

Reaction 3: ADP+D-P→ATP+D.

In preferred embodiments, the two amplification steps are repeated until the desired level of amplification is achieved. In alternative embodiments, enzyme 1 in this method can be either adenylate kinase or nucleoside monophosphate kinase, whereas enzyme 2 can be either pyruvate kinase or NDPK.

Another aspect of the invention provides methods for interrogating the identity of at least one specific base in at least one target nucleic acid in a nucleic acid sample. In these embodiments, a hybridized nucleic acid probe-target nucleic acid complex is provided. The complex contains a nucleic acid target whose sequence contains at least one base that is to be identified and a nucleic acid probe that contains a sequence that is substantially complementary to the target nucleic acid sequence and includes at least one predetermined nucleotide at an interrogation position, wherein the at least one base to be identified is aligned with the predetermined nucleotide at the interrogation position. The nucleic acid probe is depolymerized with a template specific polymerase to release nucleotides. The released nucleotides are then detected.

In a preferred embodiment, the present invention provides methods for interrogating the identity of at least one specific base in at least one target nucleic acid in a nucleic acid sample. In one embodiment, at least one nucleic acid probe and a sample suspected of containing a target nucleic acid are provided. In preferred embodiments, the target nucleic acid and the probe nucleic acid can be either RNA or DNA, the target nucleic acid includes at least one base that is to be identified, and the probe is substantially complementary to the target nucleic acid and includes at least one predetermined nucleotide at an interrogation position. In a particularly preferred embodiment of the present invention, the interrogation position is within six bases of a 3' terminal base of the nucleic acid probe. The nucleic acid probe and target nucleic acid are hybridized to form a nucleic acid probe-target nucleic acid complex. In the complex, the predetermined nucleotide at the interrogation position is aligned with and annealed or paired to the base to be identified in the target nucleic acid. In a particularly preferred embodiment, the complex is treated under conditions such that said probe is depolymerized and releases nucleotides. In some preferred embodiments, the depolymerization is catalyzed by at least one template-dependent polymerase, including, but not limited to Klenow exo minus polymerase, Taq polymerase, AMV reverse transcriptase and MMLV reverse transcriptase. In some embodiments of the present invention, the released nucleotides are detected. In a particularly preferred embodiment of the present invention, the identity of the base to be identified is determined. In other particularly preferred embodiments of the present invention, either a luciferase or NADH detection system is used to detect ATP.

In yet other embodiments, the methods of the present invention are practiced with a first probe, a second probe, a third probe and a fourth probe. In preferred embodiments of the present invention, the interrogation position of the first probe comprises a nucleic acid residue selected from the group consisting of deoxyadenosine residues and adenosine residues, the interrogation position of the second probe comprises a nucleic acid residue selected from the group consisting of uridine residues and deoxythymidine residues, the interrogation position of the third probe comprises a nucleic acid residue selected from the group consisting of deoxyguanosine and guanosine residues, and the fourth nucleic acid probe comprises a nucleic acid residue selected from the group consisting of deoxycytosine and cytosine residues. In particularly preferred embodiments, the method of the present invention is repeated with each separate probe and the results are compared in order to identify the base at the position in the target nucleic acid corresponding to the interrogation position of the probe nucleic acid. A positive result, (e.g., as indicated by increased light units over control samples), demonstrates complementarity of the residue at the interrogation position to the base to be identified. Thus, this system can be used to identify a base within a nucleic acid.

In yet another embodiment of the present invention, the nucleic acid probe-target nucleic acid complex is exposed to conditions permitting the depolymerization of the complex at a probe terminal nucleotide, by enzymatically cleaving the terminal internucleoside phosphodiester bond and forming a free XTP molecule in the presence of pyrophosphate according to the reaction:

probeNA$_n$+PP$_i$→probeNA$_{n-1}$+XTP.

In a particularly preferred embodiment, terminal 5' phosphate groups from the nucleoside triphosphate molecules are enzymatically transferred to ADP molecules to form ATP according to the following general reaction:

XTP*+ADP→XDP+ATP* wherein P* is the terminal 5' phosphate so transferred.

Another preferred embodiment of the present invention provides methods for discriminating between substantially identical nucleic acids in a sample. In particularly preferred embodiments of the invention, the substantially identical nucleic acids can be alleles or homologous nucleic acids from different species. In one embodiment, a sample suspected of containing at least two target nucleic acids sharing a region of identity that have a mismatch in at least a single nucleotide at a predetermined position is provided. Additionally, at least one nucleic acid probe which is substantially complementary to the target nucleic acid region of identity is provided. In alternative preferred embodiments, at least one hybridized nucleic acid probe-nucleic acid target complex is provided.

In particularly preferred embodiments, the probe includes at least one nucleotide at an interrogation position which is complementary to the nucleotide at a predetermined position in the region of identity of one of the target nucleic acids. In preferred embodiments, the target nucleic acid and the probe nucleic acid can be either RNA or DNA. In another particularly preferred embodiment of the present invention, the interrogation position is within ten bases of a 3' terminal base of said nucleic acid probe. The nucleic acid probe and target nucleic acid are hybridized to form a nucleic acid probe-target nucleic acid complex. In the complex, the predetermined nucleotide at the interrogation position is aligned with the nucleotide residue present at the mismatch site in the region of identity in the target nucleic acid. In a particularly preferred embodiment, the complex is treated under conditions such that said probe is depolymerized and releases nucleotides. In some preferred embodiments, the depolymerization is catalyzed by a template dependent polymerase, including, but not limited to Klenow exo minus polymerase, Taq polymerase, Tth polymerase, Tne polymerase, AMV reverse transcriptase and MMLV reverse transcriptase. In some embodiments of the present invention, the released nucleotides are detected. In a particularly preferred embodiment of the present invention, the identity of the base to be identified is determined. In particularly preferred embodiments of the present invention, either a luciferase or NADH detection system is used to detect ATP.

In yet other embodiments, a first probe and a second probe are provided. The first probe comprises a nucleotide at the interrogation position that is complementary to the first target nucleic acid at the predetermined position and the second probe comprises a nucleotide at the interrogation position that is complementary to the second target nucleic acid at the predetermined position. In alternative preferred embodiments, a first nucleic acid probe-nucleic acid target complex and a second nucleic acid probe-target nucleic acid complex are provided. The first complex contains a first nucleic acid probe hybridized to a first nucleic acid target, the first nucleic acid probe being complementary at the interrogation position to the nucleotide residue at the predetermined position of the first nucleic acid target. The second complex contains a second nucleic acid probe hybridized to a second nucleic acid target, the second nucleic acid probe being complementary at the interrogation position to the nucleotide residue at the predetermined position of the second nucleic acid target. In particularly preferred embodiments, the method is repeated with each probe and the results compared in order to identify the specific target nucleic acid present within the sample. A positive result, (e.g., as indicated by increased light units over control samples), demonstrates complementarity of the residue at the interrogation position to the base to be identified.

In yet another embodiment of the present invention, the nucleic acid probe-target nucleic acid complex is exposed to conditions permitting the depolymerization of the probe nucleic acid-target nucleic acid complex at a probe terminal nucleotide by enzymatically cleaving the terminal internucleoside phosphodiester bond in the presence of pyrophosphate and forming a free XTP molecule according to the reaction:

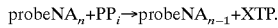
probeNA$_n$+PP$_i$→probeNA$_{n-1}$+XTP.

In a particularly preferred embodiment, terminal 5' phosphate groups from the nucleoside triphosphate molecules are enzymatically transferred to ADP molecules to form ATP according to the following general reaction:

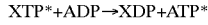
XTP*+ADP→XDP+ATP* wherein P* is the terminal 5' phosphate so transferred.

In another embodiment of the present invention, methods are provided for detecting endonuclease and exonuclease in samples. In one preferred embodiment, a solution suspected of containing endonuclease or exonuclease is provided. A nucleic acid substrate is added to the solution and the mixture is incubated for a period of time sufficient for the endonuclease or exonuclease to act on the nucleic acid. In a particularly preferred embodiment, a double-stranded nucleic acid is used as the substrate. The mixture is then reacted under conditions allowing depolymerization of the nucleic acid so that dNTPs are produced. In another particularly preferred embodiment for exonuclease detection, nucleoside monophosphates produced due to the action of the nuclease are directly converted into nucleoside triphosphates and detected. In another particularly preferred embodiment for endonuclease detection, closed circular DNA is used as the substrate. In a most preferred embodiment, either a luciferase or an NADH detection system is utilized to detect ATP.

In particularly preferred embodiments of the present invention, the nucleic acid containing solution is exposed to conditions allowing the depolymerization of the nucleic acid at terminal nucleotides by enzymatically cleaving the terminal internucleoside phosphodiester bond in the presence of pyrophosphate to form a free dNTP according to the following reaction:

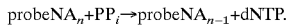
probeNA$_n$+PP$_i$→probeNA$_{n-1}$+dNTP.

In a particularly preferred embodiment, terminal 5' phosphate groups from the nucleoside triphosphate molecules are enzymatically transferred to adenosine 5'-diphosphate molecules to form adenosine 5'-triphosphate according to the following general reaction:

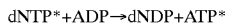
dNTP*+ADP→dNDP+ATP* wherein P* is the terminal 5' phosphate so transferred. In some preferred embodiments, the polymerase is *E. coli* DNA polymerase I or T4 DNA polymerase.

In still other preferred embodiments of the present invention, methods for detecting specific ribonucleic and deoxyribonucleic acids of interest are provided. In one preferred embodiment, at least one nucleic acid probe and sample suspected of containing a target nucleic acid are provided. In other embodiments, the nucleic acid probe is hybridized to the target nucleic acid to form a nucleic acid probe-target nucleic acid complex. Alternatively, a probe nucleic acid-target nucleic acid complex is provided. In a particularly preferred embodiment, the nucleic acid probe-target nucleic acid complex is treated under conditions so that the probe is depolymerized to release nucleotides. In other embodiments, the nucleotides are then detected. In a most preferred embodiment, either a luciferase or an NADH detection system is utilized to detect ATP.

In yet another embodiment of the present invention, the nucleic acid probe-target nucleic acid complex is exposed to conditions allowing the depolymerization of the nucleic acid probe-target nucleic acid complex at a probe terminal nucleotide by enzymatically cleaving the terminal internucleoside phosphodiester bond in the presence of pyrophosphate to form a free XTP according to the reaction:

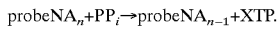
probeNA$_n$+PP$_i$→probeNA$_{n-1}$+XTP.

In a particularly preferred embodiment, terminal 5' phosphate groups from the nucleoside triphosphate molecules are enzymatically transferred to adenosine 5'-diphosphate molecules to form adenosine 5'-triphosphate according to the following general reaction:

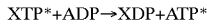
XTP*+ADP→XDP+ATP* wherein P* is the terminal 5' phosphate so transferred. In particularly preferred embodiments, the depolymerization is catalyzed by a template-dependent polymerase, including, but not limited to, Klenow fragment, Klenow exo minus polymerase, DNA polymerase I, Taq polymerase, AMV reverse transcriptase, T4 DNA polymerase, Tth polymerase, Tne polymerase and MMLV reverse transcriptase.

DETAILED DESCRIPTION OF THE INVENTION

The present invention provides a method for detection of extremely low levels of various nucleic acids including both DNA and RNA, oligonucleotides and polynucleotides in biological samples, especially samples of recombinant proteins. The extreme sensitivity, reproducibility, ease and speed of conducting the reactions using the methods of the present invention represent major advantages over methods currently in use for low level detection of nucleic acids (i.e., detection of low concentrations of nucleic acids).

The detection method can be divided into three general steps. The first step is the production of the following nucleotides: nucleoside monophosphates (XMPs) including the ribonucleoside monophosphates (NMPs) AMP, GMP, UMP, and CMP; deoxyribonucleoside monophosphates (dNMPs) including dAMP, dGMP, dTMP, and dCMP; nucleoside triphosphates (XTPs) including the ribonucleoside triphosphates (NTPs) ATP, GTP, UTP, and CTP; and the deoxyribonucleoside triphosphates (dNTPs) including dATP, dGTP, dTTP, and dCTP. In preferred embodiments, the NMPs and dNMPs are produced by nuclease digestion, and the NTPs and dNTPs are produced by depolymerization by pyrophosphorolysis. The second step, used when the initial substrate is DNA, is the transfer of the terminal phosphate from the dNTPs to ADP to form ATP. The optional step of XTP amplification can be performed at this stage to increase the sensitivity of the detection system especially when measuring samples containing low levels of DNA in the range of 1–10 pg of nucleic acid. The third step is detection of ATP by a suitable detection method. Examples of such detection systems are the luciferase detection system and NADH-based detection system.

Definitions

To facilitate understanding of the invention, a number of terms are defined below.

"Nucleoside", as used herein, refers to a compound consisting of a purine or pyrimidine base covalently linked to a pentose, while "nucleotide" refers to a nucleoside phosphorylated at one of its pentose hydroxyl groups. "XTP", "XDP" and "XMP" are generic designations for ribonucleotides and deoxyribonucleotides.

A "polynucleotide" is a covalently linked sequence of nucleotides in which the 3' position of the pentose of one nucleotide is joined by a phosphodiester group to the 5' position of the pentose of the next. An "oligonucleotide" is a polynucleotide of short length. Oligonucleotides are typically less than 100 residues long (e.g., between 8 and 100), however, as used herein, the term is also intended to encompass longer or shorter polynucleotide chains. Oligonucleotides are often referred to by their length. For example, a 24 residue oligonucleotide is referred to as a "24-mer." Oligonucleotides can form secondary and tertiary structures by self-hybridizing or by hybridizing to other polynucleotides. Such structures can include, but are not limited to, duplexes, hairpins, cruciforms, bends, and triplexes. "Nucleic acids" are polynucleotides in which the nucleotide residues are linked in specific sequence by phosphodiester bonds. A base "position" as used herein refers to the location of a given base or nucleotide residue within a nucleic acid. A "nucleic acid of interest" is any particular nucleic acid which can be detected in a sample.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

Nucleic acids are known to contain different types of mutations. As used herein, a "point" mutation refers to a base position at which two otherwise homologous nucleic acids differ. A "lesion", as used herein, refers to site within a nucleic acid where bases are deleted (e.g., a deletion mutation) or inserted (e.g., an insertion mutation), or any nucleic acid sequence differing from the wild-type sequence.

Homologous genes from different species or alleles are also known to vary in sequence. Regions of homologous genes from different species or alleles may be essentially identical in sequence. Such regions are referred to herein as "regions of identity." It is contemplated herein that a "region of substantial identity," although largely homologous, may contain "mismatches," where bases at the same position in the region of identity are different. This base position is referred to as "mismatch position."

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide, referred to as the "5' end" if its 5'phosphate or hydroxyl group is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. Accordingly, a terminal nucleotide, as used herein, is the nucleotide at the 3' or 5' end of a nucleic acid.

As used herein, the term "target nucleic acid," refers to a particular nucleic acid of interest. Thus, the "target" can exist in the presence of other nucleic acids.

As used herein, the term "probe nucleic acid" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids. The term "substantially complementary" refers to any probe which can hybridize to either or both strands of the target nucleic acid sequence under conditions of low stringency as described below or, preferably, in polymerase reaction buffer.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ (melting temperature) of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\%\ G+C)$, when a nucleic acid is in aqueous solution at 1 M NaCl (see e.g., Anderson and Young, Quantitative Filter Hybridization, in *Nucleic Acid Hybridization* (1985). Other references include more sophisticated computations which take structural as well as sequence characteristics into account for the calculation of $T_m$.

As used herein the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together.

The term "homology" refers to a degree of complementarity. There may be partial homology or complete homology (i.e., identity). A partially complementary sequence that at least partially inhibits a completely complementary sequence from hybridizing to a target nucleic acid is referred to using the functional term "substantially homologous."

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions which promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe which can hybridize to either strand of the double-stranded nucleic acid sequence under conditions of low stringency.

When used in reference to a single-stranded nucleic acid sequence, the term "substantially homologous" refers to any probe which can hybridize to (i.e., it is the complement of) the single-stranded nucleic acid template sequence under conditions of low stringency.

The term "interrogation position," as used herein refers to the location of a given base within a nucleic acid probe. Thus, the base at the interrogation position may be any ribonucleotide or deoxyribonucleotide. A set of four probes may be designed which are identical except at the interrogation position. In this example, a different base is incorporated at the interrogation position in each of the four probes.

As used herein, the terms "restriction endonucleases" and "restriction enzymes" refer to a class of enzymes, each of which cut double-stranded DNA at or near a specific nucleotide sequence.

The term "sample" as used herein is used in its broadest sense. A sample suspected of containing a nucleic acid may comprise a cell, chromosomes isolated from a cell (e.g., a spread of metaphase chromosomes), genomic DNA, RNA, cDNA and the like.

The term "detection" as used herein refers to quantitatively or qualitatively identifying a nucleotide or nucleic acid within a sample.

The term "depolymerization," as used herein, refers to the removal of a nucleotide from the 3' end of a nucleic acid by a polymerase in the presence of $P_i$ or $PP_i$.

1. Pyrophosphorolysis

Nucleic acid polymerases generally catalyze the elongation of nucleic acid chains. The reaction is driven by the cleavage of a pyrophosphate released as each nucleotide is added. Each nucleoside triphosphate has three phosphate groups linked to carbon 5 of ribose or deoxyribose. The addition of a nucleotide to a growing nucleic acid results in formation of an internucleoside phosphodiester bond. This bond is characterized in having a 3' linkage to carbon 3 of ribose or deoxyribose and a 5' linkage to carbon 5 of ribose or deoxyribose. Each nucleotide is added through formation of a new 3' linkage, so the nucleic acid strand grows in a 5' to 3' direction.

Several polymerases are also known to catalyze the reverse of the polymerization process. This reverse reaction is called "pyrophosphorolysis." The pyrophosphorolysis activity of DNA polymerase was demonstrated by Deutscher and Kornberg, *J. Biol. Chem.*, 244:3019–28 (1969). Other template dependent nucleic acid polymerases capable of pyrophosphorolysis include, but are not limited to, DNA polymerase α, DNA polymerase β, T4 DNA polymerase, Taq polymerase, Tne polymerase, Tth polymerase, *E. coli* DNA polymerase I, Klenow fragment, Klenow exo minus, AMV reverse transcriptase, and MMLV reverse transcriptase. However, not all polymerases are known to possess pyrophosphorolysis activity. For example, poly(A) polymerase has been reported to not catalyze pyrophosphorylation. (See Sippel, *Eur. J. Biochem.* 37:31–40 (1973)).

A mechanism of pyrophosphorolysis has been suggested for RNA polymerase. Although understanding of the mechanism is not necessary to use the present invention, it is believed that the partial transfer of a $Mg^{2+}$ ion from the attacking pyrophosphate to the phosphate of the internucleoside phosphodiester bond of the RNA can increase the nucleophilic reactivity of the pyrophosphate and the electrophilicity of the diester as described in Rozovskaya et al., *Biochem. J.*, 224:645–50 (1984). The internucleoside phosphodiester bond is enzymatically cleaved by the addition of pyrophosphate to the nucleoside 5' phosphate and a new phosphodiester bond is formed between the pyrophosphate and the nucleoside monophosphate.

The pyrophosphorolysis reaction can be summarized as follows:

Reaction 1: $NA_n + PP_i \rightarrow NA_{n-1} + XTP$ wherein NA is a nucleic acid, $PP_i$ is pyrophosphate and XTP is either a dNTP molecule or NTP molecule. The reaction can then be repeated so as to produce at least two XTP molecules. It should be noted that the reaction can be repeated on the same nucleic acid molecule or on a plurality of different nucleic acid molecules.

Preferred reaction mixes for depolymerization by pyrophosphorolysis, including suitable buffers for each nucleic acid polymerase analyzed are described in greater detail in the Examples. Under these conditions, sufficient NTP or dNTP is produced to accurately detect or assay extremely low amounts of nucleic acids (e.g., about 5–15 picograms).

Even though the preferred reaction conditions for polymerization and depolymerization by pyrophosphorolysis are similar, the rates of these reactions can vary greatly. For example, AMV and RLV reverse transcriptases catalyze pyrophosphorolysis under optimal conditions at a rate of about fifty- to one hundred-fold less than polymerization as demonstrated in Srivastavan and Modak, *J. Biol. Chem.*, 255(5):2000–04 (1980). Thus, the high efficiency of the pyrophosphorolysis reaction was unexpected, and appears to be associated with extremely low levels of DNA substrate, in contrast to previous DNA pyrophosphorolysis studies conducted using much higher amounts of DNA. A possible explanation for this effect might also be that the molar concentrations of free deoxyribonucleoside triphosphates produced at very low DNA levels would be predicted to be very low. Indeed these levels would be expected to be far below the Michaelis constant ($K_m$) of the enzyme. Thus, reincorporation of released dNTPs would be expected to be vanishingly small.

The pyrophosphorolysis activity of different nucleic acid polymerases also varies. For example, T4 polymerase appears to possess the greatest pyrophosphorolysis activity as measured by a luciferase assay for ATP produced by pyrophosphorolysis. Pyrophosphorolysis using T4 polymerase resulted in about a 10 fold increase in light production as compared to MMLV-RT and a 4 fold increase in light production as compared to Taq polymerase, as described in the examples.

During the development of the present invention, it was discovered that the detection of some types of nucleic acids at low picogram levels is generally enhanced by fragmenting or partially digesting the nucleic acid. Preferably, fragmentation is accomplished by sonication or restriction enzyme digestion of the nucleic acid in order to provide a plurality of smaller nucleic acid fragments. Although an understanding of the mechanism is not necessary in order to practice the present invention, this step probably enhances detection because the pyrophosphorolysis reaction only proceeds from the DNA ends, as demonstrated in the following Examples. By providing a greater number of DNA ends, more reactions are allowed to occur at any one time. It should be noted that DNA ends can be present within a molecule as well as at the end of a linear DNA fragment. For example, polymerases can catalyze pyrophosphorolysis from a gap or a nick in a DNA segment. The type of enzyme and substrate used for pyrophosphorolysis reactions determine whether fragmentation is necessary. For instance, the data set forth in the Examples demonstrate that fragmenting greatly increases detection of plasmid DNA when Taq polymerase is used, but does not affect detection when T4 polymerase is used. However, when chromosomal DNA is the substrate, fragmentation increases detection with both enzymes.

The type of cuts made by restriction enzyme digestion also affects the pyrophosphorolysis activity of different nucleic acid polymerases. As shown in the examples, MMLV-RT and Taq polymerase catalyze pyrophosphorolysis of DNA fragments with 5' overhangs, but not 3' overhangs. In contrast, T4 DNA polymerase catalyzes both 3'- and 5'-end overhang and blunt-end mediated pyrophosphorolysis. Thus, T4 DNA polymerase is a preferred enzyme for pyrophosphorolysis. When other nucleic acid polymerases are utilized for pyrophosphorolysis of restriction enzyme treated DNA, it is contemplated that care is taken to match the overhang specificity of the polymerase with the type of overhang created by the restriction endonuclease. Such care is well within the skill of those in the art.

It is to be noted that sequence specificity of pyrophosphorolysis of DNA has been previously noted during sequencing by Tabor and Richardson, *J. Biol. Chem.*, 265(14):8322–28 (1990). The sequence specificity of the pyrophosphorolysis reaction was noted when some dideoxynucleotide terminated sequence fragments were shown to be more susceptible to degradation by pyrophosphorolysis than other fragments.

Further, it is contemplated that the type of polymerase used in the pyrophosphorolysis reaction is matched to the correct nucleic acid substrate in order to produce the best results. In general, DNA polymerases and reverse transcriptases are preferred for depolymerizing DNA, while RNA polymerases are preferred for depolymerizing RNA. Reverse transcriptases or DNA polymerases with reverse transcriptase activity are preferred for depolymerizing RNA-DNA hybrids.

During the development of the present invention, it was determined that poly(A) polymerase can catalyze pyrophosphorolysis, even though no such reaction had been previously reported. Indeed, poly(A) polymerase has been widely reported to not catalyze pyrophosphorolysis. (See e.g., Sippel, *Eur. J. Biochem.*, 37:31–40 (1973) and Sano and Feix, *Eur. J. Biochem.*, 71:577–83 (1976)). Surprisingly, during the development of the present invention, it was found that poly(A) polymerase catalyzes pyrophosphorolysis. In these preferred embodiments of the present invention, the manganese chloride present in the previously reported buffers is omitted, the concentration of sodium chloride is decreased, and the pH is lowered from about 8.0 to about 7.5. Furthermore, in particularly preferred embodiments, the poly(A) polymerase pyrophosphorolysis reaction buffer contains about 50 mM Tris-Cl pH 7.5, 10 mM $MgCl_2$, 50 mM NaCl, and 2 mM $NaPP_i$ (sodium pyrophosphate).

It is important to note that the depolymerization reaction is the reverse of the polymerization reaction. Therefore, as increasing amounts of free nucleoside triphosphates are produced by depolymerization, a state of equilibrium can theoretically be attained in which polymerization and depolymerization reactions are balanced. Alternatively, where small amounts of nucleic acid are detected, the reaction can go essentially to completion without reaching equilibrium, (i.e., the nucleic acid is depolymerized into its constituent subunit nucleotides by greater than 90%). This factor is important in quantitative tests because the total amount of nucleotides released is proportional to the amount of signal generated in the detection assay. When used for qualitative detection of nucleic acid, as long as a threshold level of nucleotides are produced, it is not necessary that the reaction reach equilibrium or go essentially to completion. In preferred embodiments, the mixture of nucleoside triphosphate molecules produced by depolymerization is preferably converted to ATP as described below. For either quantitative or qualitative detection, a detectable threshold ATP concentration of approximately $1\times10^{-12}$ M in 100 µl of sample is preferably provided for detection of light in a typical luciferase assay.

In a preferred embodiment of the present invention for detecting nucleic acids, nucleic acid polymerase and pyrophosphate ($PP_i$) are added to a sample containing from less than about 1 µg nucleic acid, to less than about 10 pg of nucleic acid. To increase the sensitivity of the DNA detection, the DNA can be fragmented by treatment with a restriction endonucleases or by sonication. Next, the nucleic acid is degraded by pyrophosphorolysis releasing free NTPs or dNTPs. Enzymes useful in the pyrophosphorolysis reaction include, but are not limited to the following polymerases: AMV reverse transcriptase, MMLV reverse transcriptase, DNA polymerase alpha and beta, Taq polymerase, Tne polymerase, T4 DNA polymerase, E. coli DNA polymerase I, Klenow fragment, Klenow exo minus, Tth polymerase, and poly(A) polymerase. Most preferably, T4 polymerase is utilized for DNA pyrophosphorolysis reactions because of its recognition of 3' and 5' overhangs and blunt ends and high processivity as noted above.

Luciferase, which is part of the preferred ATP detection system, is inhibited by $PP_i$. In preferred embodiments,, care is taken so as to avoid transferring a highly inhibiting amount of $PP_i$ to the ATP detection reaction. Preferably, the amount $PP_i$ carried over to the ATP detection reaction results in a concentration of $PP_i$ in the luciferase detection reaction of less than about 100 µM, although less than about 10 µM is desirable. Therefore, the amount of $PP_i$ utilized in the pyrophosphorolysis reaction is determined by the size of the aliquot which is taken for use in the luciferase detection system. It is contemplated that the aliquot size can vary depending upon the test system used, but the amount of $PP_i$ transferred or carried over to the luciferase detection reaction should correspond to the $PP_i$ concentration parameters described above, so that the concentration of $PP_i$ is at least below about 100 µM, and preferably below about 10 µM.

2. Nuclease Digestion

In another embodiment of the present invention, the nucleic acids are first degraded into NMP or dNMP by exonuclease digestion according to the following reaction:

Reaction 2: $NA_n + H_2O \rightarrow NA_{n-1} + XMP$ wherein NA is a nucleic acid, XMP is either a dNMP or NMP, and n is the number of nucleotides in the nucleic acid.

Nuclease digestion can be accomplished by a variety of nucleases which release a nucleotide with a 5' phosphate, including S1 nuclease, nuclease BAL 31, mung bean nuclease, exonuclease III and ribonuclease H. Nuclease digestion conditions and buffers are known in the art and are available from commercial sources, and some are also described in the examples, herein incorporated by reference.

After digestion with nuclease, the NMPs or dNMPs are converted to NTPs or dNTPs respectively. U.S. Pat. No. 4,375,897 (herein incorporated by reference) describes the detection of RNA by digestion with nucleases followed by conversion to NTP. However, this method utilizes a two-step scheme in which adenylate kinase converts AMP to ADP, and pyruvate kinase then converts ADP to ATP. This method is essentially limited to the detection of poly(A) mRNA because no mechanism is suggested for conversion of dNTPs to ATP, the preferred substrate for luciferase. Furthermore, nuclease digestion or pyrophosphorolysis of DNA results in a mixture of dNTPs which do not act as efficient substrates for luciferase.

In the biosynthesis of purine and pyrimidine mononucleotides, PRPP is the obligatory ribose-5'-phosphate donor. PRPP itself is formed in a reaction catalyzed by PRPP synthetase through the transfer of pyrophosphate from ATP to ribose-5'-phosphate. This reaction is known to be reversible as described in Sabina et al., Science, 223:1193–95 (1984).

In some embodiments of the present invention, the NMP or dNMP produced by nuclease digestion is preferably converted directly to NTP or dNTP by the enzyme PRPP synthetase in the following reaction:

Reaction 3: $XMP+PRPP \rightarrow XTP+\text{ribose-5'-}PO_4$ wherein XMP is either AMP or dAMP and XTP is either ATP or dATP. Preferably, this reaction produces a threshold ATP concentration of approximately $1\times10^{-12}$ M in 100 µl of sample.

In this reaction, the pyrophosphate group of PRPP is enzymatically transferred to XMP molecules, forming XTP molecules. Examples of suitable reaction conditions and buffers are set forth in the accompanying Examples. When RNA is the substrate, the ATP produced can be directly detected.

Utilization of the PRPP reaction in the nucleic acid detection system of the present invention has advantages over previously reported methods. For example, only one step is necessary to convert an AMP or dAMP to ATP or dATP, thereby simplifying the detection system. In addition, contamination of the detection reaction with exogenous ATP, ADP, or AMP is less likely using methods of the present invention, as compared to previously reported methods.

3. Conversion of Nucleotides to ATP

It is contemplated that in some embodiments, the dNTPs or NTPs produced by pyrophosphorolysis or nuclease digestion followed by conversion of the NMPs or dNMPs to XTP which can then be used directly as substrates for luciferase, allowing detection of the nucleic acid. However, the preferred substrate for luciferase is ATP, as demonstrated by Moyer and Henderson, Anal. Biochem., 131:187–89 (1983). When DNA is the initial substrate, NDPK is conveniently utilized to catalyze the conversion of dNTPs to ATP by the following general reaction:

Reaction 4: $dNTP^* + ADP \rightarrow dNDP + ATP^*$ wherein dNTP is a mixture of deoxyribonucleoside triphosphates and dNDP is the corresponding deoxyribonucleoside diphosphate. In the reaction, the terminal 5'-triphosphate (P*) of the dNTP is transferred to ADP to form ATP. Likewise, the reaction can proceed on NTPs generated through RNA pyrophosphorylation.

Enzymes catalyzing this reaction are generally known as NDPKs. NDPKs are ubiquitous, relatively nonspecific enzymes. For a review of NDPK, see Parks and Agarwal, in The Enzymes, Volume 8, P. Boyer Ed. (1973). The conversion of NTPs or dNTPs to ATP by NDPK is preferably accomplished by adding NDPK and a molar excess of ADP over the amounts of NTPs or dNTPs expected to be produced by pyrophosphorolysis, or nuclease digestion followed by pyrophosphorylation by PRPP synthetase. Alternatively, if an ATP amplification scheme is used, a molar excess of AMP can be used as the preferred substrate. The utilization of ADP requires optimization of the amount of ADP added. Too much ADP results in high background levels. A reaction containing NDPK contains about 0.01 to 0.50 μM ADP, preferably about 0.05 μM ADP. Various useful buffers and reaction components are set forth in the Examples.

4. Amplification

As an optional step, the NTP, dNTP, or ATP generated by the pyrophosphorolysis or nuclease digestion schemes can be amplified to give even greater sensitivity. For example, amplification may be required when detection systems other than luciferase are utilized or when increased levels of signal are needed for detection by a less sensitive luminometer. "Amplification of NTP" refers to a continuous reaction, wherein 1 NTP gives rise to 2 NTPs, which can be cycled to yield 4 NTPs and so on. When AMP is added to feed the amplification reaction, ATP accumulates. PCT publication WO 94/25619 and Chittock et al., *Anal. Biochem.*, 255:120–6 (1998), incorporated herein by reference, disclose amplification systems for ATP characterized by the following coupled reactions:

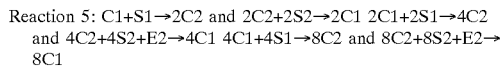

Reaction 5: C1+S1→2C2 and 2C2+2S2→2C1 2C1+2S1→4C2 and 4C2+4S2+E2→4C1 4C1+4S1→8C2 and 8C2+8S2+E2→8C1 wherein C1 is the target compound present in a sample to be amplified, S1 is the amplification substrate, E1 is a catalytic enzyme capable of utilizing C1 and S1 to produce C2, S2 is a high energy phosphate donating substrate, and E2 is a catalytic enzyme capable of utilizing C2 and S2 to produce C1, which then recycles through the reaction. According to this reaction scheme, each pass through the coupled reaction doubles the amount of C1, which can be subsequently detected. Patent Application GB 2,055,200, herein incorporated by reference, discloses an amplification system utilizing adenylate kinase and pyruvate kinase.

In providing a coupled ATP amplification reaction for use in nucleic acid detection, two main requirements should be considered. First, E1 should not be able to utilize the high energy phosphate donor utilized by E2. If E1 can utilize the high energy phosphate donor, the ATP amplification reaction proceeds in the absence of NTP or dNTP produced as a result of pyrophosphorolysis or nuclease digestion followed by pyrophosphorylation. This results in the undesirable occurrence of false positive results. Second, a molar excess of the added high energy phosphate donor is preferably provided as compared to the amount of XTP expected in the reaction. Third, E1 should be able to utilize either the NTP, dNTP, or ATP produced in step 1 by pyrophosphorolysis or nuclease digestion of the nucleic acid.

The amplification system of some preferred embodiments of the present invention can be characterized, as follows:

Reaction 6: XTP+AMP→XDP+ADP ADP+D-P→ATP wherein D-P is a high energy phosphate donor and E1 and E2 are enzymes capable of catalyzing the transfer of phosphates from an XTP to AMP and from the D-P to ADP, respectively. The ATP so produced can reenter the reaction (i.e., as XTP) and the reaction repeated until the substrates are exhausted or equilibrium is reached, resulting in the production of two ATPs for every ATP supplied to or generated by the reaction. When the target XTP is any nucleoside triphosphate other than ATP, the initial pass through the cycle yields only 1 ATP which then reenters the cycle to produce two ATP, both of which reenter the cycle to produce 4 ATP and so on. Preferably, the amplification reaction produces a threshold ATP concentration of approximately $1 \times 10^{-12}$ M in 100 μl t of sample.

In some preferred embodiments, the XTP in the amplification system above is NTP or dNTP, which can preferably be ATP provided by pyrophosphorolysis (e.g., Reaction 1) or created from XTP by NDPK conversion of ADP to ATP (e.g., Reaction 4) or provided by nuclease digestion coupled with transformation of the XMPs to XTPs (e.g., Reaction 3) followed by NDPK conversion to ATP (e.g., Reaction 4). It should be appreciated, however, that when an amplification step is utilized for a DNA substrate, the step of converting dNTP to ATP is inherent in the amplification system. Therefore, a separate converting step is not required for the present invention.

A nucleoside monophosphate kinase (NMPK) or adenylate kinase is preferably utilized as enzyme 1 (E1). NMPKs occur as a family, each of which is responsible for catalyzing the phosphorylation of a particular NMP. Until recently, it was generally thought that ATP and dATP were preferred phosphate donors. However, Shimofuruya and Suzuki *Biochem. Intl.*, 26(5):853–61 (1992) recently demonstrated that at least some NMPKs can utilize other phosphate donors such as CTP and UTP. Enzyme 2 (E2) is preferably NDPK or pyruvate kinase. NDPK's generally catalyze the transfer of the terminal 5'-triphosphate of NTPs to NDPs to form NTPs from the NDP. Pyruvate kinase catalyzes the transfer of phosphate from phosphoenolpyruvate (PEP) to ADP to form ATP. These enzymatic activities are utilized in the amplification reaction to transfer a phosphate group from a high energy phosphate donor (D-P) to either ADP or an NDP.

In particularly preferred embodiments, a high energy phosphate donor (D-P) that can be used by E2 but not by E1 is used. When E2 is NDPK, dCTP or α, β methylene adenosine 5'-triphosphate (AMP-CPP) can be utilized as D-P. When E2 is pyruvate kinase, PEP is the preferred high energy phosphate donor. Prior to the development of the present invention, the ability of NDPK to utilize these substrates at efficiencies allowing production of minute quantities of ATP was not known. As the recent literature suggests that NMPK (E1) can utilize phosphate donors other than ATP or dATP, it is surprising that these high-energy phosphate donors utilized with NMPK meet the requirements of the amplification reaction. The nonspecificity of adenylate kinase is also well known, and in the examples adenylate kinase is E-1, dCTP is not used as D-P. The high energy phosphate donor and/or AMP is preferably provided in a molar excess as compared to the amount of ATP or dNTP expected to be present in the sample, so that the high energy phosphate donor is not recycled at an appreciable rate. Although it is not intended that the present invention be limited to any particular embodiment, various buffers and reaction components are provided in the Examples.

5. Detection of ATP

In particularly preferred embodiments, the third step of nucleic acid detection is detection of the NTP, dNTP, or amplified ATP. Two well-known detection systems include the light emitting luciferase detection system, and the NADH light adsorption detection system (NADH detection system).

Luciferase detection systems are particularly useful for detecting ATP. In the presence of ATP and oxygen, luciferase catalyzes the oxidation of luciferin, producing light which can then be quantitated using a luminometer. Additional products of the reaction are AMP, pyrophosphate and oxyluciferin.

In particularly preferred embodiments, ATP detection buffer referred to as LAR buffer is utilized. This detection buffer is formulated by mixing 19.1 ml deionized water; 800 μl 0.5M Tricine, pH 8.0; 70 μl 1M $MgSO_4$; 4 μl 0.5M EDTA; 0.108 g DTT (dithiothreitol); 0.003 g luciferin; and adjusting pH to 7.8 if necessary. Preferably, about 5 to 10 ng of luciferase is used in the reaction. In some embodiments, ENLITEN® (Promega FFQ021) is used instead of LAR buffer. Although it is not intended that the present invention be limited to a specific concentration of luciferase, greater amounts of luciferase have a tendency to increase nonspecific background. In preferred embodiments, deletion of coenzyme A from the LAR reaction mix can decrease background.

In the NADH detection system, a combination of two enzymes, phosphoglycerate kinase and glyceraldehyde phosphate dehydrogenase, are used to catalyze the formation of NAD from NADH in the presence of ATP. Because NADH is fluorescent while NAD is not, ATP is measured as a loss in fluorescence intensity. Examples of NADH based ATP assays are disclosed in U.S. Pat. Nos. 4,735,897, 4,595,655, 4,446,231 and 4,743,561, and UK Patent Application GB 2,055,200, all of which are herein incorporated by reference.

In some embodiments, certain of the above reactions can be performed as single pot reactions. A "single pot reaction" is a reaction wherein at least two enzymes (i.e., E1 and E2) with catalytic activity are present in the same reaction mix and act on one or more substrate(s) (i.e., S1 and S2). In some embodiments, the reactions catalyzed by the enzymes occur simultaneously where E1 acts on S1 and E2 acts on S2. Alternatively, the reactions catalyzed by E1 and E2 can occur in a step-wise or coupled manner (e.g., where E1 acts on S1 to produce an intermediate $S2_i$ and E2 then acts on $S2_j$). Of course, in yet other embodiments, such a coupled reaction can also be essentially simultaneous.

6. Coupled Reactions

The ability to utilize combinations or mixtures of the enzymes of the present invention in single pot reactions is surprising, in light of the extremely low levels of nucleic acid detection which are achieved using the present invention. This low level detection is possible even though some enzymes are used under suboptimal conditions. As previously described, during the development of the present invention, it was found to be necessary to optimize the concentration of $PP_i$ utilized in the pyrophosphorolysis reactions to prevent inhibition of luciferase. Therefore, aliquots from the NMP, dNMP, NTP, dNTP and ATP producing reactions can be directly added to LAR buffer for luciferase detection without any purification of the reaction products. The luciferase reaction is not poisoned or otherwise quenched by the components of the reactions. This desirable feature allows high throughput screening with a minimal amount of time and effort, and also allows great flexibility in the design of the overall detection schemes. However, it is not intended that the present invention be limited to any particular reaction condition, reagents, or embodiments.

In some preferred embodiments, the pyrophosphorolysis reaction producing dNTP and the NDPK catalyzed reaction in which the NTPs or dNTPs are converted to ATP are performed in a single pot reaction in the nucleic acid polymerase buffer in these embodiments. NDPK activity is sufficient to convert dNTP to ATP, even though the polymerase buffer conditions are suboptimal for NDPK activity. The polymerase enzyme and NDPK can both be present initially in the reaction, or the NDPK can be added directly to the reaction after an incubation period sufficient for the production of NTP or dNTP. Alternatively, a nucleic acid polymerase and NDPK can be provided in the same vessel or mixture for use in the reactions described above. The mixture preferably contains the nucleic acid polymerase and NDPK in a concentration sufficient to catalyze the production of ATP when in the presence of a nucleic acid, pyrophosphate and ADP. Preferably, the polymerase is provided in a concentration of about 1 to 100 u/µl (i.e., where "u" is units) most preferably at about 5 u/µl. Preferably, the NDPK is provided in a concentration of 0.1 to 100 u/µl, most preferably at about 5 u/µl. In further preferred embodiments, the mixture is greater than 99% pure.

Similarly, the PRPP synthetase and NDPK reactions can be performed in a single pot reaction in the PRPP synthetase buffer. Again, in these embodiments, NDPK activity is sufficient even though conditions for NDPK activity are suboptimal. The nuclease digested sample containing free NMPs and dNMPs can be added to a reaction mix initially containing PRPP synthetase and NDPK, or added to a PRPP synthetase reaction followed by addition to a reaction mix containing NDPK and the luciferase detection reaction components. By way of example, certain preferred buffers and reaction components can be found in the Examples. However, it is not intended that the present invention be limited to specific buffers or reaction components. PRPP synthetase and NDPK can be provided in the same vessel or mixture for use in the reactions described above. The mixture preferably contains the PRPP synthetase and NDPK in a concentration sufficient to catalyze the production of ATP when in the presence of PRPP and ADP. Preferably, the NDPK is provided in a concentration of 0.1 to 100 u/µl, most preferably at about 5 u/µl. Preferably, the PRPP synthetase is provided in a concentration of 0.001 to 10 u/µl, most preferably at about 0.01 u/µl. If amplification is desired, the PRPP synthetase reaction is preferably heat inactivated, otherwise the PRPP synthetase converts the added AMP to ATP. Preferably the mixture is greater than 99% pure.

The pyrophosphorolysis reaction and amplification reaction can also be performed in a single pot reaction. In this single pot reaction, poly(A) polymerase or any suitable template dependent polymerase can be used, including, but not limited to, AMV reverse transcriptase, MMLV reverse transcriptase, DNA polymerase alpha or beta, Taq polymerase, Tth polymerase, Tne polymerase, E. coli DNA polymerase I, T4 DNA polymerase, Klenow fragment, Klenow exo minus, or poly(A) polymerase. In some embodiments, a first enzyme for converting AMP to ADP can be myokinase (e.g., adenylate kinase) or NMPK, and in other embodiments, a second enzyme for converting ADP to ATP can be pyruvate kinase or NDPK. In addition, in preferred embodiments, the reaction is fed AMP. In particularly preferred embodiments, Apyrase-treated AMP is utilized to reduce background due to contaminating ADP and ATP. Preferably 1 µl of 1 u/µl Apyrase is added to 19 µl of 10 mM AMP, followed by incubation at room temperature for 30 minutes and heat inactivation of the Apyrase by incubation at 70° C. for 10 min. High energy phosphate donors are also added to the reaction. In preferred embodiments, when pyruvate kinase is utilized, PEP is added. In other preferred embodiments, when NDPK is utilized, dCTP is added. Preferably, the high energy phosphate donor is added about 15 min after a preincubation with the polymerase, although this is not necessary. These reactions can be characterized as follows:

Reaction 7: $NA_n + PP_i \rightarrow NA_{n-1} + XTP$  $XTP + AMP \rightarrow ADP + XDP$
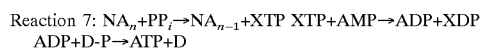

wherein NA is a nucleic acid, XTP is a nucleoside triphosphate (either a deoxynucleoside or ribonucleoside triphosphate), XDP is a nucleoside diphosphate (either a deoxynucleoside or ribonucleoside diphosphate), and D-P is a high energy phosphate donor. It should be appreciated that this reaction produces ATP, the preferred substrate for luciferase, from dNTPs. The amplification reaction proceeds as described in reaction 7 to produce a threshold ATP concentration of approximately $1 \times 10^{-12}$ M in 100 $\mu$l of sample. Preferably, the polymerase is provided in a concentration of about 1 to 100 u/$\mu$l, most preferably at about 5 u/$\mu$l. Preferably, the NDPK is provided in a concentration of 0.1 to 100 u/$\mu$l, most preferably at about 1 u/$\mu$l. Preferably, the mixture is greater than 99% pure.

7. Poly(A) mRNA Detection

In other embodiments, the reactions described above can be used to selectively detect poly(A) MRNA according to the following scheme. First oligo(dT) primers are hybridized to the poly(A) tails of the mRNA to form a DNA-RNA hybrid. Next, a pyrophosphorolysis reaction is performed using reverse transcriptase (RT). Reverse transcriptases which can be used in the present invention include, but are not limited to, Mouse Moloney Leukemia Virus (MMLV) RT and Avian Myeloma Virus (AMV) RT, or any template-dependent polymerase with reverse transcriptase activity. An advantage of this detection system is that these RTs catalyze pyrophosphorolysis of double-stranded nucleic acid and double-stranded RNA-DNA hybrids, but not single-stranded nucleic acids. Thus, the amount of poly(A) mRNA in a total cellular RNA sample can be determined using these enzymes. The pyrophosphorolysis reaction produces dTTP according to the following reaction:

Reaction 8: $TT_n + PP_i TT_{n-1} + dTTP$;

wherein $TT_n$ is oligo(dT) and $PP_i$ is pyrophosphate.

In other embodiments, the dTTP can be converted to ATP by NDPK as described in reaction 4 above, optionally amplified, and detected as described above.

8. Detection of the Presence of Cellular Material

In another embodiment of the present invention, the reactions described above can be used to detect the presence of cells in a sample. U. S. Pat. No. 5,648,232, incorporated herein by reference, describes a method for detecting cells in a sample. That method takes advantage of the adenylate kinase activity, present in all living organisms. Briefly, a sample suspected of containing microorganisms or other living cells is subjected to conditions that cause cell lysis. ADP is then added to the lysate, which is converted by endogenous adenylate kinase activity to ATP by the following reaction:

Reaction 9: 2ADP→ATP+AMP

The ATP produced by this reaction is then detected by the luciferase assay system.

The present invention also provides methods utilizing different substrates for detecting the presence of cells in a lysate of a sample suspected of containing cellular material. This system takes advantage of a coupled reaction catalyzed by endogenous adenylate kinase activity and NDPK activity according to the following reaction scheme:

Reaction 10: AMP+D-P→D+ADP and ADP+D-P→ATP+D wherein D-P is a high energy phosphate donor added to the cell lysate and AMP is adenosine monophosphate added to the cell lysate sample. In this reaction, ADP molecules are produced by the enzymatic transfer of a phosphate group from the high energy phosphate donor molecules (D-P) to the added AMP molecules. Then, ATP is produced by the enzymatic transfer of phosphate from D-P molecules to the ADP molecules according to the general reaction described above that is catalyzed by endogenous enzymes present in the cell lysate sample During the development of the present invention, co-optimization of the concentrations of nucleotides added to the samples was necessary to optimize light output from these reactions. In preferred embodiments, about 0.02 mM to 1.5 mM AMP and 0.02 mM to 1.8 mM dCTP are added to the test sample. In particularly preferred embodiments, about 0.18 mM AMP and 1.8 mM dCTP are added to the test sample. After addition of nucleotides to the sample, the samples are preferably incubated at room temperature for about 10 to 60 minutes, and light output from the samples determined by a luminometer. Other preferred buffers and reactions components can be found in the Examples.

The present invention provides important advantages over previously described cell detection systems. As AMP and dCTP are much more stable than ADP, results obtained using the present invention are more reproducible than previously used methods.

9. Detection Kits

In other embodiments of the present invention, nucleic acid detection test kits are provided for performing pyrophosphorolysis nucleic acid detection methods. In preferred embodiments the nucleic acid detection test kit comprises the essential reagents required for the method of the nucleic acid detection invention. For example, in particularly preferred kits for nucleic acid detection by pyrophosphorolysis, the kit includes a vessel containing an enzyme capable of catalyzing pyrophosphorolysis, including, but not limited to Taq polymerase, Tne polymerase, Tth polymerase, T4 DNA polymerase, Klenow fragment, Klenow exo minus, E. coli DNA polymerase I, AMV reverse transcriptase, MMLV reverse transcriptase, or poly(A) polymerase. In preferred embodiments, the concentration of polymerase ranges from about 0.1 to 100 u/$\mu$l; in particularly preferred embodiments, the concentration is about 5 u/$\mu$l. Kits for use in DNA detection also include a vessel containing NDPK and a vessel containing ADP. Preferably, these reagents are free of contaminating ATP and adenylate kinase. The NDPK is provided in concentration of about 0.1 to 100 u/$\mu$l, preferably about 1.0 u/$\mu$l. The contaminants can be removed from the enzymes by dialysis treatment. Optionally, the kit contains vessels with reagents for amplification of dNTPs or NTP to ATP. Amplification reagents include, but are not limited to pyruvate kinase, adenylate kinase, NMPK, NDPK, AMP (e.g., as the amplification substrate), and dCTP or AMP-CPP (e.g., as high-energy phosphate donors). In particularly preferred embodiments, the kit can be packaged in a single enclosure including instructions for performing the assay methods. In some embodiments, the reagents are provided in containers and are of a strength suitable for direct use or use after dilution. In alternative preferred embodiments, a standard set can also be provided in order to allow quantitation of results. In yet other preferred embodiments, test buffers for optimal enzyme activity are included. Most preferably, the NDPK and nucleic acid polymerase are provided in the same reaction mix, so that a single pot reaction can be consistently performed. In another embodiment, these kits are adapted for use in the detection of endonuclease or exonuclease activity. Kits for the detection of nuclease activities include a DNA substrate for the exonuclease or endonuclease (e.g., circular plasmid or linear DNA and instructions for use of the regents in assays for endonuclease or exonuclease detection.

In yet other embodiments, the present invention provides a nucleic acid detection kit for performing nuclease digestion nucleic acid detection methods of the present invention.

In some embodiments, this test kit comprises the essential reagents required for this method. These reagents include, but are not limited to, a nuclease, PRPP synthetase, PRPP, NDPK, and ADP together with luciferase and luciferin. In preferred embodiments, the nuclease is provided in a concentration of about 1 to 500 u/μl; in particularly preferred embodiments at a concentration of about 20 u/μl. In a particularly preferred embodiment, the PRPP synthetase is provided in concentration of about 0.01 u/μl to 10 u/μl, preferably about 0.1 u/μl. In some preferred embodiments, the kit includes all these reagents with luciferase and luciferin being provided as a single reagent solution. Most preferably, the PRPP synthetase and NDPK are provided in a single reaction mix so that a single pot reaction containing these two enzymes can be performed, simplifying the detection method. In preferred embodiments, the kits of the present invention are in the form of a single package preferably including instructions to perform the method of the invention. The reagents are provided in vessels and are of a strength suitable for direct use or use after dilution. Preferably, buffers which support the optimal enzyme activity are provided. Optionally, reagents for amplification of the ATP signal are provided as described above.

In another aspect of the present invention, test kits are provided for determining the presence of microorganisms or other cells in a test sample. In preferred embodiments, the test kits comprise the essential reagents required for the method. In some preferred embodiments, these reagents include, but are not limited to, a high energy phosphate donor which cannot be utilized by luciferase, preferably dCTP, and AMP together with luciferase and luciferin. In alternative preferred embodiments, the kit includes all these reagents with luciferase and luciferin being provided in the same solution. In other preferred embodiments, the reagents are free of contaminating components, including, but not limited to, adenylate kinase and ATP (i.e., contaminants that can cause a false positive result). In still other preferred embodiments, cell lysis cocktail can be provided for efficiently releasing the contents of the target cells for each of the assays intended. In some embodiments for detecting prokaryotic microorganisms, only a cationic detergent is needed. In yet other embodiments for fungal spore, yeast, or eukaryotic cells assays, a further nonionic detergent reagent is included. In preferred embodiments, reagents are provided in vessels and are of a strength suitable for direct use or use after dilution. In particularly preferred embodiments, a buffer solution for diluting the cell samples can also be provided.

In still further embodiments of the present invention, the kits described above can contain primers or probes for primer-mediated specific nucleic acid detection. In some embodiments, the kit contains at least one nucleic acid probe for a nucleic acid of interest. In other embodiments, the kits contain multiple primers, each of which contain a different base at an interrogation position. In each of the embodiments, the kits contain instructions for use in interrogating the identity of a specific base within a nucleic acid, for discriminating between two homologous nucleic acids which differ by one or more base pairs, and for determining whether a nucleic acid contains a deletion or insertion mutation. The types of nucleic acid probes which can be included in the kits and their uses are described in greater detail below.

10. Primer-Mediated Specific Nucleic Acid Detection

Depolymerization reactions can also be used to interrogate the identity of a specific base in a nucleic acid. For example, the identity of single base point mutations, deletions, or insertions in a nucleic acid can be determined as follows.

In one embodiment, a nucleic acid probe is synthesized which is substantially complementary to a target nucleic acid containing or suspected of containing a point mutation. It is contemplated that multiple nucleic acid probes may be utilized to identify multiple traget nucleic acids within a sample. It will be recognized that various hybridization conditions can be used, so as to vary the stringency at which hybridization occurs. Thus, depending upon the system utilized, the complementarity of the probe can be varied. Depending on the length of the probe, the GC content, and the stringency of the hybridization conditions, the probe can have as many as 10 base mismatches with the target nucleic acid, and preferably less than 5 mismatches. Most preferably, the probe has only one base mismatch with the target nucleic acid or is completely complementary to the target nucleic acid. The nucleic acid probe comprises single-stranded nucleic acid (e.g., DNA or RNA). The probe can be of varying lengths, preferably from about 10 to 100 bases, most preferably about 15 to 30 bases. In particularly preferred embodiments, the probe is complementary to the target at all bases between the interrogation position and 3' end of the nucleic acid probe.

In preferred embodiments, the probe is designed to have a predetermined nucleotide at an interrogation position. When the complementary probe base pairs or hybridizes to the target nucleic acid, the base at the interrogation position aligns with the base in the nucleic acid target whose identity is to be determined under conditions such that base pairing may occur. It is contemplated that the interrogation position can be varied within the probe. For example, in some preferred embodiments, the interrogation position is preferably within 10 bases of the 3' end of the nucleic acid probe. In still other preferred embodiments, the interrogation position is within 6 bases of the 3' end of the nucleic acid probe. In particularly preferred embodiments, the interrogation position is at the next to last or last base at the 3' end of the nucleic acid probe.

In some preferred embodiments, four different probes of equal length are synthesized, each having a different nucleotide at the interrogation position. Accordingly, it is contemplated that in some embodiments, a set of DNA probes includes a first probe with a deoxyadenosine residue at the interrogation position, a second probe with a deoxythymidine residue at the interrogation position, a third probe with a deoxyguanosine residue at the interrogation position, and a fourth probe with a deoxycytosine residue at the interrogation position. Likewise, it is also contemplated that a set of RNA probes includes a first probe with an adenosine residue at the interrogation position, a second probe with a uridine residue at the interrogation position, a third probe with a guanosine residue at the interrogation position, and a fourth probe with a cytosine residue at the interrogation position.

In the next step of some embodiments, the probe or probes are hybridized to the target nucleic acid in separate reactions so that a probe nucleic acid-target nucleic acid complex is formed. It is contemplated that hybridization conditions can vary depending on the length and base composition of the probe. In the probe-target nucleic acid complex, the nucleotide at the interrogation position is aligned with the specific base to be identified in the nucleic acid. In embodiments in which a set of probes is utilized, a different reaction is performed with each probe. Because the probes differ at the interrogation position, only one of the probes is complementary to the specific base in the target nucleic acid which is aligned with the interrogation position.

In the next step of some embodiments, the nucleic acid probe-target nucleic acid complexes are individually reacted under conditions allowing depolymerization of the probe by pyrophosphorolysis. The preferred reaction conditions for pyrophosphorolysis are described above as reaction 1 and in the following Examples. The nucleotides are then detected. In preferred embodiments, the reaction mix also contains reagents necessary to catalyze the conversion of XTP to ATP equivalents as described in reaction 4 and in the following Examples. In some preferred embodiments, the nucleotides and/or ATP produced by the depolymerization reaction are then detected by either a luciferase or NADH detection system. Complementarity of the base at the interrogation position of the nucleic acid probe to the corresponding base in the nucleic acid target is characterized by detection of a signal generated from ATP following depolymerization.

In particularly preferred embodiments, the identity of the specific base is determined by comparing the amount of ATP produced in each reaction. Depolymerization of the probe proceeds from its 3' end. When the base at the interrogation position is not complementary to the specific base in the nucleic acid, very little or no ATP is produced, and thus no signal results. In alternative embodiments, this method can be practiced with from one to four probes. It is contemplated that utilizing multiple probes, (e.g., each with a different base at the interrogation position), will prove unnecessary if a positive signal is produced (e.g., with the first probe tested).

In yet another preferred embodiment, the primer-mediated specific nucleic acid detection method of the present invention can be used to simply identify or detect a nucleic acid of interest. For this method, a nucleic acid probe (e.g., DNA or RNA) is utilized which is substantially complementary to the target nucleic acid, which can be RNA or DNA. It is contemplated that in some embodiments multiple probes may be utilized to detect multiple target nucleic acids. In a particularly preferred embodiment, the nucleic acid probe is entirely complementary to the target nucleic acid. The nucleic acid probe comprises single-stranded nucleic acid (e.g., DNA or RNA). The probe can be of varying lengths, preferably from about 10 to 100 bases, most preferably about 15 to 30 bases. Detection is carried out as described above. The nucleic acid probe-nucleic acid target complex is exposed to conditions permitting depolymerization of the probe, which results in the production of XTPs. Detection of the nucleic acid of interest is characterized by a difference in the signal generated by the XTPs produced. Preferably, the XTPs are converted to ATP as described above and the ATP detected by a luciferase or NADH detection system.

In another embodiment, the presence or absence of a lesion in the target nucleic acid may be detected. A lesion may either be an insertion mutation or a deletion mutation in the wild-type target nucleic acid. The wild-type target nucleic acid contains a region of complementarity, to which the nucleic acid probe can hybridize. Thus, the region of complementarity in the wild-type target nucleic acid is defined by the 5' and 3' end of the nucleic acid probe. When the region of complementarity contains a lesion, the nucleic acid probe may still hybridize to the target nucleic acid, but the hybridization is only partial. Depending on the size and nature of the lesion, either the 5' or 3' end of the probe may hybridize to the target nucleic acid, or a hybridization structure characterized by the presence of a loop may be formed. In each of these cases, depolymerization will be prevented. Preferably, the nucleic acid probe is designed so that the lesion to be detected begins about less than ten bases from 3' end of the probe, preferably less than about 6 bases. The nucleic acid probe comprises single-stranded nucleic acid (e.g., DNA or RNA). The probe can be of varying lengths, preferably from about 10 to 100 bases, most preferably about 15 to 30 bases. Detection of a nucleic acid containing a lesion is characterized by the difference of a signal generated from the XTP produced. Preferably, the XTPs are converted to ATP as described above and the ATP detected by a luciferase or NADH detection system.

It is contemplated that an increase in the signal produced by the primer-mediated specific nucleic acid detection methods described above can be realized by a novel cycling method. In this embodiment of the invention, two primers are designed which are complementary to each other and which have a 3' overhang at each end when they hybridize to one another. In preferred embodiments, the primers are designed so that the 3' overhang is a single base overhang. In alternative embodiments, the primers also can hybridize to a target nucleic acid. In particularly preferred embodiments, a polymerase which acts from the 3' end of nucleic acids and which does not recognize 3' overhangs is utilized for the depolymerization reaction.

In preferred embodiments, the first step of the reaction involves hybridization of an excess of one of the primers to the target nucleic acid in the presence of the polymerase and under conditions allowing depolymerization as described above. In some embodiments, no 3' overhang exists, and the depolymerase reaction proceeds from the 3' end of the primer. In some embodiments, the reaction is terminated by separating the primer from the target nucleic acid by heating the primer-target nucleic acid complexes. On average, only one base is removed from primers which were bound to the target nucleic acid, and a fraction of shortened primers are created.

In the second step, an excess of the second primer is added to the reaction. Due to the law of mass action, the shortened primers produced in the first step have a tendency to bind to the newly added complementary primers, while the non-shortened primers bind to the target nucleic acid. The shortened primers which bind to the complementary primers produce a complex with no 3' overhang on one end, and are depolymerized. This effectively doubles the amount of substrate available for the depolymerization reaction. Steps one and two can be repeated additional times until the desired level of detection is achieved. In an alternative preferred embodiment, the reactions can be coupled with NDPK as described above, to produce ATP equivalents which are detectable by a luciferase based or NADH based assay system.

The ability to interrogate the identity of a specific base in a nucleic acid also allows for discrimination between nucleic acids from different species, or even from different alleles. The ability to detect and discriminate between nucleic acids of related or unrelated species also allows the identification of species contained within a given nucleic acid-containing sample. For example, the method can be used to determine which species of several related bacteria are contained within a sample (e.g., clinical samples, environmental samples, or samples from non-human animals). It is contemplated that in some embodiments multiple nucleic acid probes may be utilized to detect multiple nucleic acid targets within a sample.

In preferred embodiments of this method, nucleic acids with substantially identical sequences from at least two species or alleles are detected. The region of identity contains at least a single nucleotide mismatch between the species or alleles in at least one predetermined position and a 3' end and a 5' end.

Next, in some embodiments, an RNA or DNA probe which is substantially complementary to the region of identity is synthesized. The probe can be of varying lengths, preferably from about 10 to 100 bases, most preferably about 15 to 30 bases. As above, this complementary probe includes an interrogation position. The interrogation position can be varied within the probe. For example, the interrogation position is preferably within 10 bases of the 3' end of the nucleic acid probe. More preferably, the interrogation position is within 6 bases of the 3' end of the nucleic acid probe. Most preferably, the interrogation position is at the next to last or last base of the 3' end of the nucleic acid probe. The nucleic acid probes are designed so that the base at the interrogation position is complementary to the nucleotide at the predetermined position of one species or allele, but not another due to the mismatch. Likewise, a second probe can be synthesized which is complementary at the interrogation position to the nucleotide at the predetermined position of a second species or allele.

This same procedure can be employed to identify the presence of multiple species within a given sample. In these embodiments, all that is required is the identification of substantially identical sequences between species which contain base mismatches.

In the next step of some embodiments, separate reactions are performed utilizing each probe. The probes are allowed to hybridize to the target nucleic acid to form a probe nucleic acid-target nucleic acid complex. In the probe nucleic acid-target nucleic acid complex, the nucleotide at the interrogation position is aligned with the nucleotide at the predetermined position in the nucleic acid, so that base pairing occurs. The probe-target nucleic acid complex is then reacted under conditions allowing depolymerization of the probe from its 3' end. Preferred conditions for depolymerization are described in the Examples and in reaction 1. The nucleotides are then detected. In some preferred embodiments, the nucleotides are converted to ATP equivalents as described in reaction 4 and in the Examples. In preferred embodiments, the ATP is detected by luciferase or NADH detection systems.

These embodiments of the present invention allow for discrimination between nucleic acids from different species or alleles, as NTPs are produced by depolymerization only when the nucleotide at the interrogation position of the probe is complementary to the nucleotide at the predetermined position of the nucleic acid from the species. As described above, significant depolymerization proceeds only if the base at the interrogation position is complementary to the base at the predetermined position in the target nucleic acid. The NTP concentration, including the ATP concentration, differs when a mismatch is present as compared to when a mismatch is not present. These differences can be detected (e.g., by either an ATP or NADH detection system).

11. Detection of Endonuclease and Exonuclease Activities

The present invention may also be used to detect endonuclease or exonuclease activity in a sample suspected of containing such activity. In one embodiment, a nucleic acid substrate is added to the sample suspected of containing endonuclease or exonuclease activity. In some embodiments, the substrate is preferably a double stranded nucleic acid, most preferably DNA. The mixture is incubated for a period of time sufficient for any endonuclease or exonuclease activity present in the sample to digest the substrate. In some embodiments, the incubation may be for about 1 to 18 hours, while in preferred embodiments the incubation is for about 12 hours. After the incubation, the amount of residual nucleic acid is detected via depolymerization by pyrophosphorolysis. Accordingly, in some embodiments, an aliquot of the incubation mixture then is exposed to conditions permitting depolymerization. These conditions are described above in reaction 1 and in the Examples. Nucleotides produced by depolymerization are then detected. In some embodiments, the nucleotides produced by depolymerization are converted to ATP equivalents as described in reaction 4 and in the examples. In preferred embodiments, the ATP is detected by a luciferase or NADH detection system. Because the residual nucleic acid is being assayed, a decrease in the assay value (e.g., light units when a luciferase detection system is utilized) as compared to a "no nuclease" control characterizes the presence of endonuclease or exonuclease activities.

In another embodiment of the present, endonuclease activity may be specifically detected. Closed circular DNA is not normally a substrate for pyrophosphorolysis because there are no DNA ends from which depolymerization can initiate. Therefore, in some embodiments, a closed circular DNA substrate is added to a sample suspected of containing an endonuclease. The mixture is incubated for a period of time sufficient for any endonuclease activity present in the sample to digest the substrate (e.g., create double-stranded breaks or nicks in the substrate). In some embodiments, the incubation may be for about 1 to 18 hours, while in preferred embodiments the incubation is for about 12 hours. After incubation, an aliquot of the incubation mixture then is exposed to conditions permitting depolymerization. These conditions are described above in reaction 1 and in the Examples. Nucleotides produced by depolymerization are then detected. In some embodiments, the nucleotides produced by depolymerization are converted to ATP equivalents as described in reaction 4 and in the Examples. In preferred embodiments, the ATP is detected by a luciferase or NADH detection system. The presence of endonuclease activity is characterized by an increase in assay units as compared to a no endonuclease control (e.g., an increase in light units when a luciferase detection system is utilized).

In another embodiment of the present invention, exonuclease activity may be detected qualitatively or quantitatively by converting dNMP produced by exonuclease digestion to ATP. In some embodiments, a nucleic acid substrate, preferably DNA, is added to a sample suspected of containing exonuclease activity. The mixture is allowed to incubate for a period of time sufficient for any exonuclease present in the sample to act on the substrate. In some embodiments, the incubation period is from about 0.5 to about 4 hours, while in preferred embodiments, the incubation period is about one hour. After incubation, an aliquot of the incubation mixture is then exposed to conditions permitting the conversion of dNMPs produced by exonuclease digestion to dNTPs. This reaction requires PRPP synthetase and PRPP and is described above in reaction 3 and in the Examples. The nucleotides are then detected. In some embodiments, the dNTPs may be converted to ATP as described in reaction 4 above and in the Examples. In some embodiments, the ATP is detected by a luciferase detection system or a NADH detection system. The presence of exonuclease activity is characterized by an increase in assay units as compared to a no nuclease control (e.g., an increase in light units when a luciferase detection system is utilized).

Other aspects of the present invention will be made apparent in the following Examples. These Examples are intended to illustrate the invention and in no way limit any aspect of the invention. Sequence ID numbers corresponding to probes are provided in Table 93.

EXAMPLES

The following abbreviations have been utilized in this application: DNA (deoxyribonucleic acid); RNA (ribonucleic acid); mRNA (messenger RNA); NDPK (nucleoside diphosphate kinase); NTP (ribonucleoside 5'-triphosphate); NDP (ribonucleoside 5'-diphosphate); ATP (adenosine 5'-triphosphate); GTP (guanosine 5'-triphosphate); CTP (cytidine 5'-triphosphate); UTP (uridine 5'-triphosphate); ADP (adenosine 5'-diphosphate); AMP (adenosine 5'-monophosphate); GMP (guanosine 5'-monophosphate); UMP (uridine 5'-monophosphate); CMP (cytidine 5'-monophosphate); dAMP (deoxyadenosine 5'-monophosphate); dGMP (deoxyguanosine 5'-monophosphate); dTMP (deoxythymidine 5'-monophosphate); dCMP (deoxycytidine 5'-monophosphate); dATP (deoxyadenosine 5'-triphosphate); dGTP (deoxyguanosine 5'-triphosphate); dCTP (deoxycytidine 5'-triphosphate); dTTP (deoxythymidine 5'-triphosphate); dNTP (deoxyribonucleoside 5'-triphosphate); dNDP (deoxyribonucleoside 5'-diphosphate); XTP (ribonucleoside 5'-triphosphate and/or deoxyribonucleoside 5'-triphosphate); XMP (ribonucleoside 5'-monophosphate and/or deoxyribonucleoside 5'-monophosphate); Ppi (pyrophosphate); PRPP (phosphoribosylpyrophosphate); AMP-CPP (α,β methylene adenosine 5'-triphosphate); PEP (phosphoenol pyruvate); MMLV (mouse maloney leukemia virus); AMV (avian myeloblastosis virus); HIV (Human Immunodeficiency Virus); RLV (Rauscher Leukemia Virus); and u (unit).

Example 1

Detection of ATP Using Luciferase

The ultimate sensitivity of detection using an enzyme based detection system is related to the ability of the enzymatic reaction to produce a measurable signal over background. This example describes the detection of very low levels of ATP using luciferase.

Luciferase Assay Reagent buffer (LAR) was produced by mixing: 19.1 ml nanopure water; 800 μl 0.5M Tricine (Sigma T9784), pH 8.0; 70 μl 1M $MgSO_4$ (Promega AA319, Lot #970931); 4 μl 0.5M EDTA (Promega AA189, Lot #962131); 0.13 g DTT (dithiothreitol, Promega V31SA); 0.003 g Beetle Luciferin (Promega E160C, Lot #79838); 0.0044 g Coenzyme A, pH 7.8 (Pharmacia 28-3001-03 Lot #7053001031). A 0.1M ATP solution was prepared by dissolving solid ATP (Sigma A9187) in Tris-Cl 10 mM pH 7.5. This stock solution was diluted into Tris-Cl 10 mM pH 7.5 to produce solutions at 100 μM, 1 μM, 10 nM, and 100 pM. Recombinant luciferase (Promega #1701, Lot #6414002) was diluted to 1 mg/ml, 100 μg/ml, and 10 μg/ml using nanopure water.

Reactions were assembled in duplicate containing the following components as described in Table 1.

TABLE 1

| | | Component | |
|---|---|---|---|
| Reaction # | LAR | Luciferase | Total Luciferase Added |
| 1 | 50 ul | 1 ul 1 mg/ml | 1 μg |
| 2 | 50 ul | 1 ul 100 μg/ml | 100 ng |
| 3 | 50 ul | 1 ul 10 μg/ml | 10 ng |
| 4 | 50 ul | 0 | 0 ng |

Immediately upon addition of the luciferase, the tube was read in a Turner TD-20e Luminometer. The values obtained are listed in Table 2.

TABLE 2

| Reaction | Light Units 1 | Light 2 | Average | Filter*Units |
|---|---|---|---|---|
| 1 | 90.6 | 66.09 | 78.345 | 286, 22406.67 |
| 2 | 2048 | 2096 | 2072 | none, 2072 |
| 3 | 148 | 122 | 135 | none, 135 |
| 4 | 0 | 0 | 0 | none, 0 |

*Light reduction filter used to reduce signal, light units measured must be multiplied by filter to obtain light output.

Luciferase requires both ATP and luciferin to produce a light signal. The light produced in the reactions above is the result of ATP contamination of either the LAR reagent or the luciferase added to the reactions. Ten and five nanogram levels of luciferase were chosen for further studies since they produced the lowest level of background light without ATP addition, yet were expected to give greatly increased light upon addition of ATP.

Reactions were assembled in duplicate containing 50 μl LAR buffer, 1 μl stock luciferase providing either 5 or 10 ng of luciferase to the reaction, and ATP at the concentrations listed below. Light output from reactions was then immediately determined with a Turner TD-20e Luminometer. The results are described in Table 3. These data indicate that luciferase is capable of detecting low levels of ATP if levels of luciferase are used that minimize the background resulting from ATP contamination of the reagent.

TABLE 3

| Luciferase (ng) | ATP Conc. | μl | Light Units | | Filter | Avg. Light Units |
|---|---|---|---|---|---|---|
| 10 | 0 | 0 | 131.7 | 119.6 | (none) | 125.7 |
| 10 | 100 uM | 5 | 26.09 | 25.25 | 286 | 7221.5 |
| 10 | 1 uM | 5 | 249.5 | 226.1 | (none) | 237.8 |
| 10 | 10 nM | 5 | 131.7 | 232.6 | (none) | 182.2 |
| 10 | 100 pM | 5 | 215.4 | 143.9 | (none) | 179.7 |
| 5 | 0 | 0 | 52.76 | 50.04 | (none) | 51.4 |
| 5 | 100 uM | 5 | 17.99 | 18.47 | 286 | 5213.8 |
| 5 | 1 uM | 5 | 156.4 | 174.4 | (none) | 167.9 |
| 5 | 10 nM | 5 | 46.13 | 34.37 | (none) | 40.3 |

Example 2

Limit of ATP Detection Using Luciferase

This example demonstrates that the light output values obtained from reactions with very low levels of ATP are statistically different from appropriate control reactions. The limit of detection can be defined as the amount of the analyte that generates a signal which has less than a 0.05 probability of identity to the data from control reactions using the Student's t-Test.

ATP (Sigma A9187, Lot #36H7808 Promega, stored overnight at −20° C.) in 10 mM Tris-Cl pH 7.5 was diluted to 500 nM and 50 nM. Various amounts of ATP were added to 350 μl LAR, with 10 mM Tris-Cl added to make up the difference in volume (385 total). Only 10 mM Tris-Cl was added to the control to determine the background signal. After mixing, 6 aliquots of 50 μl control and samples were transferred to luminometer tubes. Luciferase (2 μl of 2.5 ng/μl in 1× CCLR with 1 mg/ml BSA (1× CCLR, Cell Culture Lysis Reagent, Promega E153A, Lot #7903201)) was added to the reaction, the tube was tapped to mix the reagents and light output was immediately determined with the Turner TD-20e luminometer. The data is presented in Table 4.

TABLE 4

| Reaction | ATP (M) | Light |
|---|---|---|
| 1 | 0 | 2.744 |
| 2 | 0 | 2.606 |
| 3 | 0 | 2.849 |
| 4 | 0 | 2.834 |
| 5 | 0 | 2.801 |
| 6 | 0 | 2.778 |
| 7 | $4.5 \times 10^{-10}$ | 4.883 |
| 8 | $4.5 \times 10^{-10}$ | 5.192 |
| 9 | $4.5 \times 10^{-10}$ | 4.945 |
| 10 | $4.5 \times 10^{-10}$ | 4.220 |
| 11 | $4.5 \times 10^{-10}$ | 5.282 |
| 12 | $4.5 \times 10^{-10}$ | 5.216 |
| 13 | $9.1 \times 10^{-10}$ | 7.167 |
| 14 | $9.1 \times 10^{-10}$ | 8.100 |
| 15 | $9.1 \times 10^{-10}$ | 7.774 |
| 16 | $9.1 \times 10^{-10}$ | 8.047 |
| 17 | $9.1 \times 10^{-10}$ | 8.010 |
| 18 | $9.1 \times 10^{-10}$ | 7.677 |
| 19 | $1.82 \times 10^{-9}$ | 10.70 |
| 20 | $1.82 \times 10^{-9}$ | 11.02 |
| 21 | $1.82 \times 10^{-9}$ | 11.93 |
| 22 | $1.82 \times 10^{-9}$ | 11.91 |
| 23 | $1.82 \times 10^{-9}$ | 12.27 |
| 24 | $1.82 \times 10^{-9}$ | 11.92 |

The Student's t-Test (a 2-tailed test for 2 samples with unequal variance) was used to analyze the data. The light output from each ATP concentration was compared to the light output of the background control, and a p-value determined for each comparison. The results of the analysis are presented in Table 5. A p-value of less than 0.05 indicates that the 2 sets of results being compared are statistically different from each other. Each of the ATP concentrations compared to background signal have a p-value of less than 0.05. Therefore, this statistical test indicates that each of the ATP concentrations analyzed is detectable over background.

TABLE 5

| | p-value |
|---|---|
| $1.82 \times 10^{-9}$ M ATP | $2.2 \times 10^{-5}$ |
| $9.1 \times 10^{-10}$ M ATP | $9.5 \times 10^{-8}$ |
| $4.5 \times 10^{-10}$ M ATP | $2.3 \times 10^{-7}$ |

Example 3
Detection of dATP Using Luciferase

Detection of polydeoxyribonucleosides using luciferase can in theory be performed through the measurement of dATP if the enzyme used for detection can utilize dATP. In this example, the ability of luciferase to use deoxyadenosine triphosphate (dATP) as compared to adenosine triphosphate (ATP) was tested.

Reactions were assembled containing 50 µl LAR, 2 or 4 µl luciferase stock (providing 5 or 10 ng of luciferase to the reactions) and 0 or 5 µl 1 mM dATP (Sigma, final concentration of dATP approximately 100 µM). Luciferase was the last component added. Immediately upon enzyme addition, the light output of the reactions was determined using a Turner TD-20e Luminometer. The results are provided in Table 6. These data show that luciferase can be used to directly detect dATP.

TABLE 6

| Luciferase Level | dATP + or − | Light Units | | Avg. Units Units |
|---|---|---|---|---|
| 5 ng | − | 423 | 295.7 | 359.4 |
| 5 ng | + | 1450 | 1621 | 1535.5 |
| 10 ng | − | 703 | 705.5 | 704.3 |
| 10 ng | + | 3684 | 3441 | 3562.5 |

Example 4

Pyrophosphate Inhibition of Luciferase

The reaction of luciferase produces pyrophosphate from ATP or dATP and is inhibited by pyrophosphate. Some of the reaction schemes described later use pyrophosphate as a substrate for other enzymes. In order to use levels of pyrophosphate in these reactions which do not inhibit detection of nucleotide using luciferase, we determined the levels of inhibition produced by various concentrations of pyrophosphate on the production of light from luciferase.

A new buffer, LAR without Coenzyme A, was made as described in Example 1. This buffer and the original LAR were then used to formulate various reactions with the compositions shown below. The reactions were assembled with luciferase being the final component added. Immediately upon enzyme addition, the light output of the reactions were determined with a Turner TD-20e Luminometer. The results are provided in Table 7. These data indicate that the light output from luciferase can be measured in the presence of pyrophosphate and that more than 50% of the activity can be seen with pyrophosphate concentrations as high as 100 µM. In addition, these data indicate that removal of Coenzyme A from the LAR greatly lowers the background light produced by the reactions without greatly effecting the activity of luciferase.

TABLE 7

| LAR With CoA (µl) | LAR Minus CoA (µl) | ATP (2 µM) | | Pp$_i$ | | Luciferase (2.5 µg/ml) | Light Units | | Avg. |
|---|---|---|---|---|---|---|---|---|---|
| | | | 1 mM | 100 µM | | | | | |
| 50 µl | — | — | − | − | | 2 µl | 209.9 | 227 | 218.5 |
| 50 µl | — | 5 µl | − | − | | 2 µl | 3462 | 3674 | 3568 |
| 50 µl | — | — | + | − | | 2 µl | 9.73 | 9.43 | 9.6 |
| 50 µl | — | 5 µl | + | − | | 2 µl | 169.5 | 180.9 | 175.2 |
| 50 µl | — | 5 µl | − | + | | 2 µl | 1452 | 1449 | 1450.5 |
| — | 50 µl | — | − | − | | 2 µl | 0.035 | 0.046 | 0.041 |

TABLE 7-continued

| LAR With CoA (μl) | LAR Minus CoA (μl) | ATP (2 μM) | 1 mM | Pp$_i$ 100 μM | Luciferase (2.5 μg/ml) | Light Units | | Avg. |
|---|---|---|---|---|---|---|---|---|
| — | 50 μl | 5 μl | - | - | 2 μl | 3735 | 3289 | 3512 |
| — | 50 μl | -    | + | - | 2 μl | 0.0003 | 0.0003 | 0.0003 |
| — | 50 μl | 5 μl | + | - | 2 μl | 254.5 | 308 | 281.3 |
| — | 50 μl | 5 μl | - | + | 2 μl | 2041 | 2069 | 2055 |

Example 5
Testing ADP as an Inhibitor of Luciferase

Some of the reaction schemes described later use ADP as a substrate for other enzymes. ADP is a possible inhibitor of luciferase. Therefore, we determined the levels of inhibition produced by various concentrations of ADP on the production of light from luciferase and ATP.

Stock solutions of ADP (Sigma) or ATP were dissolved in 10 mM Tris-Cl pH 7.5 and diluted to produce various stock concentrations. Reactions were assembled which contained 2 μl 2.5 μg/ml luciferase, 50 μl LAR, 5 μl ADP or 5 μl 10 mM Tris-Cl pH 7.5 and 5 μl ATP or 5 μl 10 mM Tris-Cl pH 7.5. The luciferase was the final component added to these reactions. Immediately upon enzyme addition, the light output of the reactions was measured using a Turner TD-20e Luminometer. The final nucleotide concentrations of the reactions and the light output of the reactions are summarized in Table 8. These data indicate that ADP does not greatly effect the ability of luciferase to produce light using ATP as a substrate. Thus, if low concentrations of ADP are added to luciferase reactions from reactions performed using other enzymes, little effect on ATP detection through the use of luciferase is expected.

TABLE 8

| ATP | ADP | Light Output | | Average |
|---|---|---|---|---|
| — | — | 485.8 | 423.5 | 454.7 |
| 2 μM | — | 4945 | 4930 | 4937.5 |
| — | 100 μM | 4800 | 4418 | 4609 |
| 2 μM | 100 μM | 6834 | 7207 | 7020.5 |
| — | 1 μM | 513 | 463 | 488 |
| 2 μM | 1 μM | 4303 | 4152 | 4227.5 |
| — | 10 nM | 419.6 | 419 | 419 |
| 2 μM | 10 nM | 4534 | 4625 | 4579.5 |

Example 6
NDPK Transformation of ADP to ATP, Using Deoxynucleotides

Luciferase can detect ATP at much lower concentrations than dATP or other nucleotides. If dNTPs could be used to generate ATP, an increase in sensitivity may result. For this reason, we tested the ability of enzymes to transfer the terminal phosphate of dNTPs to ADP, forming ATP and dNDPs.

Reactions were assembled which contained 100 μl LAR, 10 ng luciferase in the presence or absence of dNTPs (1 μM final concentration when added), and 10 units NDPK (Sigma #N0379, Lot #127F81802). The reactions were assembled with the exception of luciferase and incubated 15 min at room temperature. Luciferase was added and light output of the reactions was measured immediately using a Turner TD-20e Luminometer. The light output values measured are provided in Table 9. These data confirm that NDPK is capable of transferring the phosphate from nucleoside triphosphates to ADP to form ATP which can be detected using luciferase.

TABLE 9

| Tube # | dNTP | ADP | NDPK | ATP | Light Units |
|---|---|---|---|---|---|
| 1 | — | + | + |   | 883 |
| 2 | — | — | + | + | 15361 |
| 3 | — | + | — |   | 543 |
| 4 | — | — | — | + | 21970 |
| 5 | dATP | + | + |   | 13356 |
| 6 | dATP | — | + |   | 151 |
| 7 | dCTP | + | + |   | 13007 |
| 8 | dCTP | — | + |   | 6.9 |
| 9 | dGTP | + | + |   | 13190 |
| 10 | dGTP | — | + |   | 7.3 |
| 11 | TTP | + | + |   | 19230 |
| 12 | TTP | — | + |   | 9.0 |

Example 7
NDPK Transformation of ADP to ATP Using NDPK and ATP Analogs

Some enzymes which may be used to transform nucleotides show specificity for adenosine nucleotides as phosphate donors. Adenosine nucleotides may not be used as high energy phosphate donors for these converting enzymes if a luciferase detection system is to be utilized. This is because light is generated by luciferase from the added adenosine nucleotide. However, the converting enzymes may be utilized if an analog of adenosine is identified that can be used by the converting enzymes but not by luciferase. This example indicates how such analogs can be tested for their ability to be used by converting enzymes but not by luciferase.

Approximately 5 mg ATP (Sigma A9187, Lot #36H7808), α,β methyleneadenosine 5'-Triphosphate (AMP-CPP) (Sigma M6517, Lot #96H7813) and β,γ methylene adenosine 5'-triphosphate (AMP-PCP) (Sigma M7510, Lot #34H7840) were diluted in Tris-Cl, 10 mM, pH 7.5. The absorbance of a 1:100 dilution of these solutions into 50 mM Tris-Cl, pH 7.5 was read at 259 nm using a Beckman DU650 Spectrophotometer. The absorbances were used to determine the concentration of these solutions using a molar extinction coefficient of $15.4 \times 10^3$M. Recombinant luciferase was diluted into CCLR containing 1 mg/ml BSA to a concentration of 2.5 ng/μl. When the reactions were assembled, 2 μl luciferase was added from the 2.5 ng/μl stock solution and the light emission of the solutions were immediately read Turner TD-20e Luminometer. The data is provided in Table 10.

TABLE 10

| Reaction | LAR | ATP | AMP-CPP* | AMP-PCP* | # rxn | Avg. |
|---|---|---|---|---|---|---|
| 1 | 50 µl | — | — | — | 3 | 426.4 |
| 2 | 50 µl | 4 µM | — | — | 7 | 5762 |
| 3 | 50 µl | — | 552 µM | — | 2 | 349.2 |
| 4 | 50 µl | 4 µM | 552 µM | — | 2 | 5072.5 |
| 5 | 50 µl | — | 5.52 µM | — | 2 | 465.8 |
| 6 | 50 µl | 4 µM | 5.52 µM | — | 2 | 5843.5 |
| 7 | 50 µl | — | 5.52 nM | — | 2 | 429.8 |
| 8 | 50 µl | 4 µM | 55.2 nM | — | 2 | 4152 |
| 9 | 50 µl | — | — | 1.14 mM | 2 | 260.35 |
| 10 | 50 µl | 4 µM | — | 1.14 mM | 2 | 3735.5 |
| 11 | 50 µl | — | — | 11.4 µM | 2 | 431.25 |
| 12 | 50 µl | 4 µM | — | 11.4 µM | 2 | 5930 |
| 13 | 50 µl | — | — | 114 nM | 2 | 389.35 |
| 14 | 50 µl | 4 µM | — | 114 nM | 2 | 6093.5 |

*Final concentration in the reaction, solution produced by addition of 5 ul of a more addition concentrated stock solution.

Micromolar solutions of these ATP analogs do not produce light above that of reactions containing no added nucleotide and do not greatly lower the light output of reactions containing low levels of ATP from the values seen in the absence of these analogs. These analogs do not inhibit luciferase and are not utilized by luciferase. Thus, these data indicate that these analogs can be tested for their ability to be used with enzymes for the transformation of nucleotides.

The following reactions were performed to determine if either AMP-CPP or AMP-PCP could be used by NDPK. All reactions were assembled in duplicate and incubated at room temperature 20 min. Ten nanograms luciferase was added and the light output of the reactions immediately measured using a Turner TD-20e Luminometer. The data is provided in Table 11. These data demonstrate the analog AMP-CPP is utilized by the enzyme NDPK as a substrate to generate ATP from ADP. The values seen with AMP-CPP, ADP and NDPK present are substantially higher than those seen for ADP alone, ADP and NDPK without AMP-CPP and NDPK alone. Analogous experiments can be performed to test other enzymes for their ability to use nucleotide substrates in a similar fashion.

TABLE 11

| Reaction | LAR-CoA | ADP (2 × 10⁻⁴M) | NDPK | AMP-CPP (2 × 10⁻⁵M) | AMP-PCP (2 × 10⁻⁵M) | Avg. |
|---|---|---|---|---|---|---|
| 1 | 100 µl | — | — | — | — | 0.21 |
| 2 | 100 µl | 0.5 µl | — | — | — | 60.23 |
| 3 | 100 µl | 0.5 µl | 1 µl | — | — | 59.77 |
| 4 | 100 µl | 0.5 µl | 1 µl | 5 µl | — | 617.95 |
| 5 | 100 µl | — | 1 µl | 5 µl | — | 1.81 |
| 6 | 100 µl | 0.5 µl | 1 µl | — | 5 µl | 69.35 |
| 7 | 100 µl | — | 1 µl | — | 5 µl | 0.03 |
| 8 | 100 µl | — | 1 µl | — | — | 0.05 |

Example 8
NMPK Transformations of ADP

This example demonstrates a method for testing the ability of an enzyme to transform nucleoside diphosphates into nucleotides which can be used by luciferase for the generation of light. The enzyme Nucleoside Monophosphate Kinase (NMPK, Sigma, N-4379) can transfer phosphate from ATP to UMP, forming UDP and ADP. This experiment demonstrates that this enzyme preparation can also be used to form ATP from ADP, probably through the reaction:

2ADP→ATP+AMP

The reactions were assembled in duplicate as prescribed in Table 12 and incubated at room temperature for 30 min. At that time, 10 ng of luciferase was added and the light output of the solutions was measured using a Turner TD-20e Luminometer. The data is provided in Table 12. These data indicate that NMPK can transform ADP into ATP. Similar experiments can be used to test the ability of other enzymes to perform similar transformations.

TABLE 12

| Reaction | LAR-CoA* | NMPK** | ADP (10⁻⁵M) | Avg. Light |
|---|---|---|---|---|
| 1 | 100 µl | — | — | 0.58 |
| 2 | 100 µl | 10 µl | — | 0.23 |
| 3 | 100 µl | — | 5 µl | 14.81 |
| 4 | 100 µl | 10 µl | 5 µl | 211.4 |

*Luciferase Assay Reagent formulated without added Coenzyme A or ATP.
**Sigma N-4379, Lot #96H0166, dissolved in ATP free water to 3.35 U/ml.

Example 9
Combination of NMPK And NDPK, dCTP, and AMP

One potential method for amplifying an ATP signal requires two enzymes and a phosphate donor. For this system to operate, the first enzyme, E1, must be able to convert AMP to ADP but must be unable to use the phosphate donor. The second enzyme, E2, must be able to effectively use the phosphate donor to transform any ADP formed to ATP. This example demonstrates a method to test the ability of a combination of enzymes to be used in such a combination reaction scheme. The Examples above demonstrate that NDPK can transform ADP to ATP using dCTP as a phosphate donor.

The reactions were assembled as presented in Table 13 and incubated for 30 min at room temperature. Then 10 ng of luciferase in 2 µl of 1×CCLR with 1 mg/ml BSA was added and the light output of the reactions was measured using a Turner TD-20e Luminometer. The data is presented in Table 13.

The reaction which could have produced significant ATP if NMPK could transform AMP to ADP using dCTP as a substrate is reaction 4. This reaction produced only minute amounts of ATP as measured by luciferase mediated light production. Reaction 5 (where NDPK was used to transform ADP to ATP using added dCTP) and reaction 6 (where NMPK was used to transform ADP to ATP) produced much more ATP. Since all enzymes were shown to be active, these data indicate that NMPK essentially cannot use dCTP to transform AMP to ADP. This is the essential requirement for the ATP amplification system described above. In this particular instance E1 (NMPK) cannot use the phosphate donor (dCTP) but can utilize AMP and ATP to produce 2 ADP molecules (the reverse of the reaction 6). The second enzyme, E2 (NDPK), can use the phosphate donor (dCTP) to transform the ADP produced by the first enzyme to create 2ATP from the 2ADP using 2dCTP. These ATPs can then re-enter the cycle. This protocol can be used to test combinations of enzymes and phosphate donors for their ability to act as the enzymes in our ATP amplification schemes.

In addition, this combination of reactions allows the user to determine if any of the enzymes used are contaminated with unexpected activities that may influence the system. For example, removing the NMPK, dCTP, or AMP from the system prevents any ATP accumulation, as expected. However, eliminating the NDPK only has a small influence on the rate of ATP accumulation. These data suggest that the NMPK source used contains a small amount of activity which can take the place of NDPK in this system.

Performing similar experiments should allow a user to determine if other enzymes can be used in such amplifica-

TABLE 13

| Reaction | LAR-CoA | AMP | dCTP | NMPK* | NDPK** | Water | Tris-Cl | ADP | Light |
|---|---|---|---|---|---|---|---|---|---|
| 1 | 100 µl | — | — | 10 µl | 1 µl | — | 15 µl | — | 0.008 |
| 2 | 100 µl | 5 µl | — | — | — | 11 µl | 10 µl | — | 0.126 |
| 3 | 100 µl | — | 10 µl | — | — | 11 µl | 5 µl | — | 0.159 |
| 4 | 100 µl | 5 µl | 10 µl | 10 µl | 1 µl | — | — | — | 10.93 |
| 5 | 100 µl | — | 5 µl | — | 1 µl | 10 µl | — | 10 µl | 4049 |
| 6 | 100 µl | — | — | 10 µl | — | 1 µl | 5 µl | 10 µl | 2309 |
| 7 | 100 µl | — | — | — | — | 11 µl | 5 µl | 10 µl | 115.9 |

*NMPK concentration at 5 mg/ml of Sigma N4379.
**NDPK concentration of 10 units/µl Sigma NO379, Nucleoside stocks at: AMP (Sigma A2002, Lot #20H7035), 2 × 10-5M; dCTP (Promega U122A, Lot #6858402), 2 × 10$^{-5}$M, ADP 1 × 10$^{-5}$M (Sigma A2754 Lot #65H7880), 10 mM Tris-Cl.

Example 10
Amplification of ATP Using NMPK, NDPK, dCTP and AMP with ATP Spikes

The enzyme combination presented in Example 9 should be capable of greatly increasing the relative ATP concentration through the cyclic amplification reaction scheme presented earlier. This example demonstrates the amplification of different levels of input ATP using these enzymes and nucleotides. The reactions were assembled as presented in Table 14 and incubated at room temperature. When the reactions reached incubation time 0, 20, 40, 60, 80, 100, 120, 180, and 240 min, 112 µl samples of each reaction were transferred to luminometer tubes and 10 ng luciferase were added. The light output of the reactions was immediately tions schemes, as shown in Example 11.

TABLE 14

| Reaction | AMP | dCTP | NMPK | NDPK | ATP |
|---|---|---|---|---|---|
| 1 | 10 µl | 10 µl | 100 µl | 10 µl | 1 pmol |
| 2 | 10 µl | 10 µl | 100 µl | 10 µl | 100 fmol |
| 3 | 10 µl | 10 µl | 100 µl | 10 µl | 10 fmol |
| 4 | 10 µl | 10 µl | 100 µl | 10 µl | — |
| 5 | 10 µl | 10 µl | — | 10 µl | 1 pmol |
| 6 | 10 µl | 10 µl | 100 µl | — | 1 pmol |
| 7 | — | 10 µl | 100 µl | 10 µl | 1 pmol |
| 8 | 10 µl | — | 100 µl | 10 µl | 1 pmol |

TABLE 15

| Reaction | 0 Min | 20 Min | 40 Min | 60 Min | 80 Min | 100 Min | 120 Min | 180 Min | 240 Min |
|---|---|---|---|---|---|---|---|---|---|
| 1 | 95 | 179.5 | 249.9 | 339.5 | 562 | 670.9 | 709.4 | 1157 | 1497 |
| 2 | 20.42 | 37.11 | 54.95 | 85.1 | 122.5 | 164.9 | 206.1 | 409.7 | 746 |
| 3 | 12.3 | 25.09 | 39.37 | 55.79 | 93.8 | 120.5 | 156.1 | 325.7 | 573.7 |
| 4 | 11.8 | 25.54 | 37.45 | 54.64 | 87.8 | 113.1 | 143.8 | 299.1 | 548.7 |
| 5 | 96.4 | 75 | 63.63 | 56.75 | 51.72 | 54.72 | 56.61 | 58.97 | 60.97 |
| 6 | 110 | 183.5 | 247.8 | 285.9 | 426.1 | 503.9 | 624.5 | 958 | 1301 |
| 7 | 91.7 | 99 | 98.6 | 85.2 | 93.2 | 94.2 | 95.4 | 91.5 | 90.4 |
| 8 | 3.521 | 2.755 | 2.31 | 2.058 | 2.092 | 2.173 | 1.682 | 1.088 | 0.73 | measured using a Turner TD-20e Luminometer. The data is presented in Table 15.

The reactions with ATP added (Reactions 1, 2, and 3) increased in ATP more rapidly than the reactions without added ATP (Reaction 4). The rate of increase of the ATP was dependent upon the amount of ATP first added to the reaction. Thus, this combination of enzymes amplified the input ATP signal and the amount of ATP produced at a particular time was dependent upon the starting amount of ATP added.

Example 11
Amplification of ATP Using Adenylate Kinase and Pyruvate Kinase

This example demonstrates a second ATP amplification system using a non-nucleoside based phosphate donor. The enzymes used are: adenylate kinase (an enzyme which produces 2ADP from one ATP and one AMP but which cannot use PEP as a phosphate donor and Pyruvate Kinase (an enzyme which phosphorylates ADP to form ATP using PEP as a phosphate donor). The reactions were assembled as presented in Table 16. These reactions were incubated at room temperature and 109 μl of the reactions was removed at 0, 30, 60, and 120 min. Luciferase (2 μl, 10 ng in 1×CCLR with 1 mg/ml BSA) was added and the light output of the reaction was immediately measured using a Turner TD-20e Luminometer. The data is presented in Table 17.

After 30 min incubation the reaction containing ATP (reaction 1) increased much more rapidly than the reaction with no ATP added (reaction 2). Thus, the ATP sample was amplified. Also note that in this set of reactions, the ATP content of reactions 1 and 2 reached a final ATP level. This indicates that the reactions reached an equilibrium value.

Finally, note that the reaction with no added AMP also increased over time. This suggests that one of the components was contaminated with either AMP or ADP. Further experiments demonstrated that the contaminating nucleotide was present in the pyruvate kinase solution used in this study. The following example demonstrates a method for removing this contaminating nucleotide.

nucleoside contamination. One of the components suspected of contamination is pyruvate kinase. A sample of this enzyme was dialyzed against 50 mM $KPO_4$, 15 mM $MgCl_2$ pH 7.6 in SpectraPor Dialysis tubing with a molecular weight cut off of 3,500 da. The dialysis was performed twice against 1000× amount of buffer for several hours at 4° C. to remove free adenosine. The reactions were assembled according to Table 18. These data indicate that following dialysis the enzyme solution was slightly more dilute than prior to dialysis. By adding 5.3 μl of the post dialysis enzyme and 5.0 μl of the pre-dialysis enzyme, equal amounts of PK were added to the reactions.

Five hundred microliters of LAR-CoA was added to the assembled reactions and the final reactions incubated at room temperature. At 0, 10, 20, and 30 min, 114 μl of these reactions were added 10 ng luciferase in 5 μl 1×CCLR with 1 mg/ml BSA and the light output of the solutions was immediately measured using a Turner TD-20e Luminometer. The data is presented in Table 19.

TABLE 16

| Reaction | ATP | AMP | AK | PEP | PK | Tris-CL | ALAR-CoA | Buffer |
|---|---|---|---|---|---|---|---|---|
| 1 | 12.5 μl | 5 μl | 10 μl | 5 μl | 12.5 μl | — | — | 500 μl |
| 2 | — | 5 μl | 10 μl | 5 μl | 12.5 μl | 12.5 μl | — | 500 μl |
| 3 | 12.5 μl | — | 10 μl | 5 μl | 12.5 μl | 5 μl | — | 500 μl |
| 4 | 12.5 μl | 5 μl | — | 5 μl | 12.5 μl | — | 10 μl | 500 μl |
| 5 | 12.5 μl | 5 μl | 10 μl | — | 12.5 μl | — | 5 μl | 500 μl |
| 6 | 12.5 μl | 5 μl | 10 μl | 5 μl | — | — | 12.5 μl | 500 μl |

*The concentrations of these components were: ATP, $1 \times 10^{-6}$M; AMP, $1 \times 10^{-4}$M; Adenylate Kinase (AK) Sigma M5520, lot #16H9558), 7 U/μl in 50 mM $KPO_4$, 15 mM $MgCl_2$, pH 7.5 (Buffer A); PEP, (Phosphoenolpyruvate, Sigma P-7002, Lot #46H3777, 100 mM in deionized water; PK (pyruvate kinase, (Sigma P-7286, Lot #45H9504), 0.1 U/μl in Buffer A), and; Tris-Cl, 10 mM Tris-Cl, pH 7.5.

TABLE 17

| | Time (Min) | | | |
|---|---|---|---|---|
| Reaction | 0 | 30 | 60 | 120 |
| 1 | 93.6 | 536.4 | 683.8 | 670.4 |
| 2 | 14.98 | 120.6 | 594.8 | 639.3 |
| 3 | 105.5 | 219.4 | 321 | 384.7 |
| 4 | 112.5 | 97.2 | 98.8 | 94.1 |
| 5 | 83.1 | 16.84 | 16.03 | 15.02 |
| 6 | 90.6 | 21.61 | 22.79 | 21.2 |

Example 12
Removal of Interfering Substances in Pyruvate Kinase Using Dialysis

This example demonstrates methods for detecting contaminating nucleosides in enzymes used in the various technologies discussed in the other examples and removing the contaminating material.

Additionally, another amplification scheme is described. This scheme utilizes: Adenylate Kinase (E1); NDPK (E2); AMP; and the ATP analog AMP-CPP as the high energy phosphate donor. If AMP is left out of this reaction, no increase in an initial ATP signal should take place unless one of the other materials is contaminated with AMP (or ADP).

Reactions performed as described in Example 11 suggested that one of the components may have adenosine Two main observations can be derived from this data. First, the AK, NDPK, AMP, AMP-CPP enzyme-substrate combination can be used to amplify an ATP signal. However, production of ATP from some contamination source allows reactions not given ATP added to achieve a final ATP concentration similar to those given an ATP spike.

The reaction to which no AMP or PK were added (reaction 2) does not increase over time. However, the reactions to which the undialyzed PK was added and no AMP was added give high light output over time (reaction 5). Addition of dialyzed PK to reactions lacking AMP (reaction 8) demonstrate increased light output over time, but the rate of increase is dramatically reduced from that seen without dialysis.

This Example demonstrates that yet another ATP amplification system can be used to generate higher ATP levels from a starting ATP spike. In addition, this Example shows that these systems can be used to determine if solutions contain contaminating nucleotides and that dialysis can be used to fractionate contaminating nucleotides from enzymes utilized in ATP amplification reactions.

TABLE 18

| Reaction | AMP | ATP | NDPK | AMP-CPP | AK | PK | $P_1$ Buffer | Tris |
|---|---|---|---|---|---|---|---|---|
| 1 | 10 µl | 10 µl | 5 µl | 10 µl | 10 µl | — | 5 µl | — |
| 2 | — | 10 µl | 5 µl | 10 µl | 10 µl | — | 5 µl | 10 µl |
| 3 | 10 µl | — | 5 µl | 10 µl | 10 µl | — | 5 µl | 10 µl |
| 4 | 10 µl | 10 µl | 5 µl | 10 µl | 10 µl | 25 µl Sample 1 | — | — |
| 5 | — | 10 µl | 5 µl | 10 µl | 10 µl | 25 µl Sample 1 | — | 10 µl |
| 6 | 10 µl | — | 5 µl | 10 µl | 10 µl | 25 µl Sample 1 | — | 10 µl |
| 7 | 10 µl | 10 µl | 5 µl | 10 µl | 10 µl | 26.5 µl Sample 2 | — | — |
| 8 | — | 10 µl | 5 µl | 10 µl | 10 µl | 26.5 µl Sample 2 | — | 10 µl |
| 9 | 10 µl | — | 5 µl | 10 µl | 10 µl | 26.5 µl Sample 2 | — | 10 µl |

*The compositions of these solutions were: AMP, $1 \times 10^{-4}$M; ATP, $2 \times 10^{-6}$M; NDPK, 0.1 U/µl; AMP-CPP, $1 \times 10^{-3}$M; AK, 0.75 units/µl; PK, 5 µl of pyruvate kinase pre-dialysis (sample 1) or post dialysis (sample 2), Pi buffer (described above); and, Tris, 10 mM Tris-Cl, pH 7.5.

TABLE 19

| Reaction | Time (Min) | | | |
|---|---|---|---|---|
| | 0 | 10 | 20 | 30 |
| 1 | 60.35 | 349.7 | 529 | 563.1 |
| 2 | 54.73 | 50.74 | 49.79 | 52.79 |
| 3 | 51.62 | 59.11 | 279 | 420.7 |
| 4 | 87.4 | 666.6 | 754.2 | 779 |
| 5 | 73.1 | 213.9 | 354.6 | 412.4 |
| 6 | 24.41 | 479.1 | 701.7 | 707.6 |
| 7 | 69.9 | 449.3 | 577.3 | 595.2 |
| 8 | 50.92 | 76.03 | 118.4 | 148.9 |
| 9 | 12.92 | 229.3 | 541.3 | 569.4 |

TABLE 20

| Tube # | AMP | PRPP | PRPP Syn | Light Units | |
|---|---|---|---|---|---|
| 1 | + | + | + | 3440 | 3424 |
| 2 | + | − | + | 0.522 | 0.501 |
| 3 | + | + | − | 6.649 | 4.619 |
| 4 | − | + | + | 7.096 | 7.139 |
| 5 | + | − | − | 1.874 | 0.430 |
| 6 | − | − | − | 5.203 | 4.794 |
| 7 | − | + | + | 96.0 | 0.361 |
| 8 | − | − | − | 462.8 | 0.603 |

Example 13
PRPP Synthetase, Reactions with Adenosine

The enzyme 5' phosphorylribose 1' pyrophosphate synthetase (PRPP Synthetase) transfers a pyrophosphate from ATP to D-ribose 5' phosphate. This experiment was performed to determine if this enzyme could be used with AMP and 5'phosphoribose 1' pyrophosphate to generate ATP and D-ribose 5' phosphate.

ATP, AMP and PRPP were diluted in 10 mM Tris, pH 7.3. PRPP Synthetase (Sigma #P0287) was diluted in PRPP Synthetase reaction buffer (see below). 2 µl ATP, 2 µl AMP, 2 µl PRPP, and 2 µl PRPP Synthetase (or appropriate buffers) were added as indicated in Table 20 to 20 µl PRPP Synthetase reaction buffer.

The reactions were incubated in the 37° C. water bath for 30 min. The tubes were removed from the water bath and 100 µl LAR (without CoA) was added. Then, 126 µl was transferred to a luminometer tube. 10 ng luciferase was added in 5 µl 1×CCLR containing 1 mg/ml BSA and light output measured with Turner TD-20e Luminometer. The data presented in Table 21. This data demonstrates that PRPP Synthetase can transfer pyrophosphate from non-nucleotide substrates to AMP to form ATP.

The nucleotide concentrations in the reaction were: ATP (when added) $1.2 \times 10^5$M; AMP (when added) $2.9 \times 10^{-5}$M, and; PRPP (when added) $2.6 \times 10^{-5}$M. $6 \times 10^{-4}$ units of the enzyme (PRPP Synthetase) was added per reaction. PRPP Synthetase buffer is 50 mM triethanolamine, 50 mM potassium phosphate, pH 7, 0.37 mM EDTA, 10 mM $MgCl_2$, 1 mg/ml BSA.

Example 14
PRPP Synthetase, Reactions with Deoxyadenosine Monophosphate

Some schemes for the detection of DNA require the conversion of dAMP, generated by nuclease digestion of DNA, to dATP. This example demonstrates that the enzyme PRPP Synthetase can perform the transformation of dAMP to dATP using PRPP as a cosubstrate. In addition, this transformation can be monitored by luciferase detection at much higher sensitivities if the dATP formed is used to transform ADP to ATP through the action of NDPK added to the reaction.

The reactions were assembled in duplicate as shown in Table 21. The concentrations of the reaction components were: dAMP $2.9 \times 10^{-4}$M in 10 mM Tris pH 7.3; AMP $2.9 \times 10^{-4}$M in 10 mM Tris pH 7.3; PRPP $2.6 \times 10^{-4}$M in 10 mM Tris pH 7.3; PRPP Syn (PRPP Synthetase) (Sigma #P0287) 100× dilution of stock enzyme which is at 0.03 u/µl. The components were added to twenty microliters of PRPP Synthetase Buffer (see Example 13). After incubating for 47 min at 37° C., 100 µl LAR was added to all reactions along with 10 ng luciferase and the light output of the reactions was immediately measured. The data is presented in Table 22. PRPP was able to utilize dAMP as a substrate (comparing reaction 1 to 2, 3, 4 and 5). However, the amount of light produced by reaction was low, probably due to the fact that luciferase uses dATP at a much lower efficiency than ATP as presented earlier.

TABLE 21

| Reaction | dAMP | PRPP | PRPP Syn |
|---|---|---|---|
| 1 | 2 µl | 2 µl | 2 µl |
| 2 | 2 µl | — | 2 µl |
| 3 | 2 µl | 2 µl | — |
| 4 | 2 µl | — | — |
| 5 | — | 2 µl | 2 µl |

TABLE 22

| Reaction | Tube A | Tube B | Avg. Light |
|---|---|---|---|
| 1 | 18.2 | 22.1 | 20.15 |
| 2 | 1.4 | 1.4 | 1.4 |
| 3 | 4.2 | 3.8 | 4 |
| 4 | 2.1 | 1.8 | 1.95 |
| 5 | 13.1 | 15.8 | 14.45 |

In order to demonstrate the transfer of phosphate from dATP to ADP to form ATP, the reactions presented in Table 23 were assembled in duplicate in twenty microliters of PRPP Synthetase Buffer (for solution compositions, see tables above). They were then incubated at 37° C. for 34 min. The added components had the following formulations: ADP $2.3 \times 10^{-2}$M in 10 mM Tris-Cl pH 7.3; NDPK-1000× dilution of Sigma #N0379 at 10 u/µl (final concentration 0.01 u/µl). The tubes were then incubated for an additional 60 min at 37° C., 10 ng luciferase added, and the light output measured using a Turner TD-20e Luminometer. The data is presented in Table 24. These data indicate that the dATP produced by the PRPP Synthetase reaction can be transferred to ADP by the action of NDPK to produce ATP.

TABLE 23

| Reaction | dAMP | PRPP | PRPP Syn | ADP | NDPK |
|---|---|---|---|---|---|
| 1 | 2 µl | 2 µl | 2 µl | 2 µl | 2 µl |
| 2 | 2 µl | 2 µl | 2 µl | — | — |
| 3 | 2 µl | 2 µl | 2 µl | 2 µl- | — |
| 4 | 2 µl | 2 µl | 2 µl | — | 2 µl |
| 5 | — | 2 µl | 2 µl | 2 µl | 2 µl |

TABLE 24

Light Units

| Reaction | Tube A | Tube B |
|---|---|---|
| 1 | 812.1 | 839.3 |
| 2 | 19.2 | 37.5 |
| 3 | 53.6 | 52.6 |
| 4 | 168.4 | 173.1 |
| 5 | 43.6 | 38.9 |

Example 15
Digestion of Poly(dA) Using Nucleases

One potential method for detecting DNA would be to digest the polymer to dNMPs, transform the dNMPs to dNTPs, form ATP from the dNTPs using ADP and NDPK, and then detect the ATP using luciferase. This example demonstrates the digestion of a deoxyadenosine polymer.

A solution of dAMP was made by adding 990 µl water and 10 µl 1×TE buffer (10 mM Tris-Cl, 1 mM EDTA pH 8.0) to 25 units polyadenylic acid (Pharmacia 27-786, Lot #5017836021). A reaction was assembled with the following materials: 450 µl nanopure water, 50 µl 10×S1 Nuclease buffer (Promega Corp. M577A, Lot #6748605) and 10 µl polydeoxyadenylic acid solution above. The absorbance change at 260 nm was monitored on a Beckman DU650 Spectrophotometer. The rate of change in the absorbance of the solution was 0.0020 Abs/min. At this point, 1 µl S1 Nuclease (Promega Corp. E576B, Lot #6800810) was added and the absorbance change of the solution redetermined and found to be 0.0156 abs/min. Since small oligonucleotides and mononucleotides display absorbance values higher than a corresponding amount of polynucleotide, this indicates that this enzyme can digest the polymer.

The reaction conditions given below are those used to digest the polydeoxyadenylic acid polymer samples that are used in later examples.

Three reactions were assembled which contained:

Reaction 1: 90 µl polydeoxyadenylic acid solution described above, 10 µl 10×S1 nuclease reaction buffer.

Reaction 2: As Reaction 1 above.

Reaction 3: 90 µl nanopure water, 10 µl S1 nuclease reaction buffer.

At time equals zero min of digestion, 10 µl of each was removed and added to 490 µl 50 mM Tris-Cl pH 8.0. Immediately, 1 µl S1 nuclease was added to the remaining reaction mixtures 1 and 3 but not 2, and the mixtures were allowed to incubate at room temperature. Additional 10 µl samples of the reactions were removed after 20, 50 and 140 min of reaction and diluted into 490 µl 50 mM Tris-Cl pH 8.0. The data is presented in Table 25. The absorbance of the solution in Reaction #1 increased, again indicating that the polymer in this reaction was digested over time. A second set of reactions was produced as described above. The only difference with these reactions was that 50 units of Poly (dA)(Sigma P-0887, Lot #67H0226) was dissolved in 1.5 ml of TE buffer and used in the reactions. After the 140 min of digestion, these reactions were used as described in Example 16.

TABLE 25

| | Net Absorbance At 260 nm Of Samples From Reaction | | |
|---|---|---|---|
| Time (Min) | #1 | #2 | #3 |
| 0 | 0 | 0 | 0 |
| 20 | 0.0726 | −0.0088 | −0.0025 |
| 50 | 0.1425 | 0.0291 | −0.0041 |
| 140 | 0.1445 | −0.003 | −0.0044 |

Example 16
Detection of Poly (dA) Using Nucleases and PRPP Synthetase

In this example, the digested polynucleotide described in Example 15 is detected by two different methods. Both methods begin with transformation of the deoxynucleotides to deoxynucleoside triphosphates using PRPP Synthetase and PRPP. In the first method, ADP is converted to ATP using the deoxynucleoside triphosphates formed in the PRPP synthetase reaction and the resulting ATP detected using luciferase. In the second method, AMP is converted to ATP using the dNTPs formed by the PRPP Synthetase reaction, simultaneously amplified and detected using luciferase.

Table 26 presents the components of the PRPP Synthetase reaction. The concentrations of the components were: PRPP, $2.6 \times 10^{-4}$ M in 10 mM Tris-Cl pH 7.5; PRPP Synthetase, $6.0 \times 10^{-4}$ Units (Sigma P0287) per 2 µl in PRPP Synthetase Buffer. For composition of Buffer, refer to PRPP Synthetase Buffer in Example 13. The nucleoside digests containing S1 were diluted in deionized water to yield the amount of polymer listed in Table 26 in 8 µl solution and added to the appropriate reactions. The digest containing no polymer was diluted identically to those with polymer. Eight microliters of this solution contained all the components in the samples containing 720 ng polymer except the Poly(dA). All the reactions were incubated 32 min at 37° C. At this point all the reactions were heated at 95° C. for 5 min to inactivate the PRPP Synthetase and cooled in an ice bath 5 min.

TABLE 26

| Reaction | Digest | Buffer | PRPP | PRPP Synthetase | Poly(dA)* | S1 |
|---|---|---|---|---|---|---|
| 1 | 720 ng | 80 µl | 2 µl | 2 µl | — | — |
| 2 | 72 ng | 80 µl | 2 µl | 2 µl | — | — |
| 3 | 7.2 ng | 80 µl | 2 µl | 2 µl | — | — |
| 4 | 0.72 ng | 80 µl | 2 µl | 2 µl | — | — |
| 5 | — | 80 µl | 2 µl | 2 µl | 720 ng | — |
| 6 | — | 80 µl | 2 µl | 2 µl | — | (720 ng) |

A. First Detection Method

Twenty microliters of each reaction was added to 100 µl LAR minus CoA. Ten nanograms luciferase was immediately added and the light production of the reactions was measured. A second 20 µl sample was added to 100 µl LAR minus CoA, followed by addition of ADP (2 µl 2 µg/ml stock) and NDPK (2 µl $1 \times 10^{-2}$ u/µl), and allowed to incubate 20 min at room temperature. After the incubation, 10 ng luciferase was added to the reactions and the light production of the reactions was measured using a Turner TD-20/20 luminometer at 52.1% sensitivity. The data obtained for these measurements are presented in Table 27.

These data show that direct measurement of the dNTPs is possible using luciferase if relatively high amounts of digested DNA are to be detected (see reaction 1 vs. 5 and 6 in the no NDPK column). However, much more sensitive detection is provided when the dNTPs are used to convert ADP to ATP using NDPK.

TABLE 27

| | | Light Units | |
|---|---|---|---|
| Reaction | DNA | No NDPK | With NDPK |
| 1 | 180 ng | 43 | 711 |
| 2 | 18 ng | 15 | 227 |
| 3 | 1.8 ng | 13 | 77 |
| 4 | 0.18 ng | 11 | 37 |
| 5 | no S1 | 13 | 161 |
| 6 | no poly | 11 | 28 |

B. Second Detection Method

Twenty microliters of the reaction mixtures from the heat inactivated PRPP Synthetase reactions were added to ATP amplification reactions in an attempt to use the initial dNTPs to produce ATP. This would allow easier detection of the dATP produced by the PRPP synthetase reaction.

The reactions were assembled as demonstrated in Table 28. The reactions were mixed and the first aliquot of 109.3 µl (1/7 of the reaction) was removed immediately after adenylate kinase was added. The aliquot was placed in a luminometer tube, 10 ng luciferase was added, the tube tapped to mix, and then the light output was measured with a Turner TD-20/20 luminometer at 52.1% sensitivity. Subsequent aliquots were removed at 20 min intervals and measured immediately. The reactions were incubated at room temperature. The data obtained is presented in Table 29.

These results show that it is possible to amplify the dATP produced from digested DNA after conversion to nucleoside triphosphates. Note that the light output obtained by this method is greater than the light output of the non-amplified PRPP Synthetase method.

TABLE 28

| | Reaction Components** | | | | | | | |
|---|---|---|---|---|---|---|---|---|
| Reaction | DNA | LAR-CoA | AMP | PEP | AK | PK | Tris | PRPP Buffer |
| 1 | poly(dA) 180 ng, 20 µl* | + | + | + | + | + | — | — |
| 2 | poly(dA) 18 ng, 20 µl* | + | + | + | + | + | — | — |
| 3 | poly(dA) 1.8 ng, 20 µl* | + | + | + | + | + | — | — |
| 4 | poly(dA) 0.18 ng, 20 µl* | + | + | + | + | + | + | — |
| 5 | poly(dA) no S1 nuclease. 20 µl* | + | + | + | + | + | + | — |
| 6 | S1 nuclease, no poly(dA), 20 µl* | + | + | + | + | + | + | — |
| 7 | ATP 14 µl 2 mM | + | + | + | + | + | — | 6 µl |
| 8 | dATP 14 µl 2 mM | + | + | + | + | + | — | 6 µl |
| 9 | dATP 14 µl 200 nM | + | + | + | + | + | — | 6 µl |
| 10 | dATP 14 µl 20 nM | + | + | + | + | + | — | 6 µl |
| 11 | none | + | + | + | + | + | 14 µl | 6 µl |

*These reactions used 20 µl of the heat-inactivated PRPP Synthetase reactions from the first part of this example.
**The components were: ATP (Sigma A9187) in 10 mM Tris pH 7.5, dATP (Sigma D6500) in 10 mM Tris-Cl pH 7.5, AMP 7 µl of $2 \times 10^{-4}$M in 10 mM Tris-Cl pH 7.5, LAR-CoA (LAR without CoA) 700 µl per reaction tube, PEP (phosphoenol pyruvate-ammonium salt) (synthesized) 7 µl 100 mM, AK (adenylate kinase/myokinase) (Sigma M5520) 14 µl 0.75 u/µl in Buffer A, PK (pyruvate kinase) (Sigma P7286, dialyzed 48 hours) 17.5 µl 0.13 u/µl, Tris-Cl 10 mM pH 7.5, PRPP Synthetase Buffer-see example 13.

TABLE 29

|    | 0 Minutes* | 20 Minutes* | 40 Minutes* |
|----|------------|-------------|-------------|
| 1  | 11.56      | 187.30      | 5860.0      |
| 2  | 1.89       | 25.26       | 1598.0      |
| 3  | 2.09       | 12.52       | 671.3       |
| 4  | 1.34       | 20.21       | 1638.0      |
| 5  | 1.56       | 17.04       | 1009.0      |
| 6  | 1.11       | 9.44        | 691.1       |
| 7  | 27.21      | 315.30      | 7426.0      |
| 8  | 8.84       | 186.20      | 7177.0      |
| 9  | 1.52       | 9.76        | 295.6       |
| 10 | 1.14       | 5.18        | 184.1       |
| 11 | 0.72       | 4.10        | 169.7       |

*Light output in Relative Light Units.

Example 17
Digestion of PhiX 174 HinF 1 Fragments

Polynucleotides encountered in nature are often double stranded. The DNA fragments generated by digestion of PhiX 174 DNA using endonuclease HinFI are double-stranded DNA fragments of various sizes. In order to test whether double stranded DNA could be detected, the PhiX 174 was directly used as a test substrate or digested with nucleases to produce nucleotides which could be converted to nucleoside triphosphates as in previous Examples.

The following conditions were used to digest DNA fragments from bacteriophage PhiX 174. These materials were placed in three 1.5 ml polypropylene tubes: 50 µl of PhiX 174 HinF I fragments (Promega G175A, Lot #773603); 40 µl 5 mM MgSO$_4$; 5 µl Exo III buffer (10×) (Promega E577B, 4853216), and 5 µl Nanopure water. Fifty microliters TE buffer and 40 µl 5 mM MgSO$_4$; 5 µl ExoIII buffer (10×) and 5 µl Nanopure water were added to one sample. Two of the samples containing PhiX 174 DNA were further treated with 2 µl Exo III (Promega M181A, 5512708) and the tubes placed in a 37° C. water bath for 60 min. ExoIII was also added to the sample without DNA and the sample incubated at 37° C. 60 min.

At this time, 800 µl nanopure water and 100 µl (10×) S1 Nuclease Buffer (Promega M577A, Lot #6748605) were added to all samples. Three microliters S1 nuclease (Promega E576B, Lot #789881) were then added to all samples. All samples were incubated at 37° C. for 30 min.

Two hundred microliters from each of the three tubes containing DNA were diluted with 300 µl 1×TE Buffer and the absorbance read at 260 nm using a Beckman DU 650 spectrophotometer. The readings recorded were: tube one (no nuclease addition), 0.3073; tube two (treatment with Exo III), 0.5495; tube three (treatment with Exo III and S1), 0.5190. The increased absorbance values of the tubes treated with nuclease indicates that the polymer was digested. These digests were subsequently used in other studies (see Example 18).

Example 18
Detection of PhiX 174 HinF 1 Fragments Using Nucleases, PRPP Synthetase, NDPK This example demonstrates the detection of DNA by digestion of the polymer to nucleoside monophosphates using nucleases, transformation of the nucleoside monophosphates to nucleoside triphosphates using PRPP Synthetase and PRPP along with transformation of ADP to ATP using the nucleoside triphosphates generated by the action of PRPP Synthetase, and detection of the ATP using luciferase. A sample of deoxynucleotide (Poly (dA)) was prepared as described in example 17. Different amounts of deoxynucleotide were used in the reactions as presented in Table 30.

The following additions were made to each reaction: 2 µl PRPP, 2 µl PRPP Synthetase, and 20 µl PRPP Synthetase buffer. The reactions proceeded at 37° C. for 28 min at which time the reactions were transferred to 100 µl LAR containing 2 µl ADP and 2 µl NDPK. This second reaction was allowed to proceed at room temperature for 20 min. The amount of ATP produced was measured by the addition of 10 ng of luciferase followed by measuring light output with a luminometer. The data is presented in Table 30.

These data show that this combination of enzymes allows detection of DNA.

TABLE 30

| Reaction | Nucleotide | Amount In Rxn | Light Units |
|----------|------------|---------------|-------------|
| 1 | dAMP | 200 ng, 600 pmoles | 1018 |
| 2 | dAMP | 20 ng, 60 pmoles | 636 |
| 3 | dAMP | 2 ng, 6 pmoles | 178 |
| 4 | dAMP | 200 pg, 600 fmoles | 83 |
| 5 | none | 0 ng | 69 |
| 6 | PhiX 174 only | 100 ng (= 300 pmoles dNMP; approx. 75 pmoles dAMP) | 46 |
| 7 | PhiX 174 + ExoIII | 100 ng | 472 |
| 8 | PhiX 174 + Exo + S1 | 100 ng | 448 |
| 9 | No DNA + Exo + S1 | 0 ng | 55 |

Example 19
Detection of PhiX 174 HinF 1 Fragments Using Reverse Transcriptase and NDPK The following example demonstrates the detection of double-stranded DNA fragments having nucleotide overhangs on their ends using reverse transcriptase. The reactions were assembled as demonstrated in Table 31.

The components were: Buffer, 5×MMLV-RT Buffer, (Promega Part #M531A, Lot #7090101); DNA, PhiX 174 HinF 1 Fragments (Promega Part #G175A, Lot #7733602); NaPP$_i$, 10 mM Sodium Pyrophosphate (Promega Part #C113A, Lot #6675705); ADP, 1 µM ADP (Sigma A-5285, Lot #56H7815); NDPK, NDPK, (Sigma N-0379, Lot #127F81802) 1 U/µl in 25 mM sodium citrate; MMLV-RT (Promega M170A, Lot #6980019, 1 U/µl), incubated for 30 min at 37° C., then 2 µl of the reactions was added to 100 µl of L/L (Promega FF2021, luciferase/luciferin reagant). The light production by the reactions was immediately measured with a Turner TD-20e Luminometer. The data is presented in Table 31.

These data show that MMLV-RT can be used to pyrophosphorylate DNA and that the resulting nucleotides can be used to transform ADP to ATP and the ATP formed detected using luciferase. Other enzymes can be tested for their ability to perform this reaction in a similar fashion.

TABLE 31

| Rx | Buffer | DNA | NaPPi | ADP | NDPK | Water | MMLV-RT | Light |
|----|--------|-----|-------|-----|------|-------|---------|-------|
| 1 | 4 µl | 1 µl of 100 ng/µl 100 | 1 µl | 2 µl | 1 µl | 10 µl | 1 µl | 165. |
| 2 | 4 µl | 1 µl of 20 ng/µl | 1 µl | 2 µl | 1 µl | 10 µl | 1 µl | 155. |

TABLE 31-continued

| Rx | Buffer | DNA | NaPPi | ADP | NDPK | Water | MMLV-RT | Light |
|---|---|---|---|---|---|---|---|---|
| 3 | 4 μl | 1 μl of 4 ng/μl | 1 μl | 2 μl | 1 μl | 10 μl | 1 μl | 58.9 |
| 4 | 4 μl | 1 μl of 800 pg/μl | 1 μl | 2 μl | 1 μl | 10 μl | 1 μl | 18.0 |
| 5 | 4 μl | 1 μl of 160 ng/μl | 1 μl | 2 μl | 1 μl | 10 μl | 1 μl | 4.54 |
| 6 | 4 μl | 1 μl of 32 ng/μl | 1 μl | 2 μl | 1 μl | 10 μl | 1 μl | 1.70 |
| 7 | 4 μl | — | 1 μl | 2 μl | 1 μl | 11 μl | 1 μl | 0.95 |
| 8 | 4 μl | 1 μl of 100 ng/μl | | 1 μl | 2 μl | 1 μl | 11 μl | 0.62 |

Example 20
Limit of DNA Fragment Detection Using Reserve Transcriptase, NDPK, and Luciferase As shown in Example 18, DNA can be detected using luciferase when the DNA is fragmented and pyrophosphorylated using a reverse transcriptase to produce dNTPs and the terminal phosphate is transferred from the dNTPs to ADPs to form ATP. This Example demonstrates that the light units produced in reaction containing very low levels of DNA are statistically significant compared to values for the appropriate control reactions. As with Example 2, the limit of detection is statistically determined using Student's t-Test. The reactions presented in Table 32 were assembled in duplicate. The components were: Buffer 5×MMLV-RT Buffer (Promega M531A); DNA, PhiX 174 HinF1 fragments diluted in TE (Promega G175A); TE, Tris-Cl EDTA (Promega AA641); NaPPi, 40 mM Sodium Pyrophosphate (Promega C113A); ADP, ADP 2 μM in Tris-C1 10 mM pH 7.3 (Sigma A5285); NDPK, 1 unit/μl in water (Sigma N0379); water, nanopure water; MMLV-RT, MMLV reverse transcriptase 200 units/μl (Promega M170A).

All reagents except DNA and MMLV-RT were added to a 1.5 ml polypropylene tube and mixed. Then duplicate 16.5 μl aliquots were transferred to new polypropylene tubes. One microliter of MMLV-RT was added to each tube, followed by 2.5 μl of DNA at varying concentrations or 2.5 μl of TE. The reactions were incubated at 37° C. for 10 min, then 2 μl of the 20 μl reaction was added to 100 μl of L/L reagent (which includes luciferase, Promega F202A and F180A, mixed) in a luminometer tube. The tubes were tapped to mix, and then light output levels were immediately measured using a Turner TD-20e luminometer at 52.1% sensitivity (this sensitivity is comparable to the Turner TD-20/20 readings). The data is presented in Table 33.

The light output for each DNA concentration (6 readings each) was compared to the light output of the background control (no DNA), and a p-value determined for each comparison. The results of the analysis are presented in the following Table 34. As in Experiment 2, the p-values were less than 0.05 for each sample tested. Therefore, less than 10 pg of DNA can be reliably detected.

TABLE 32

| Reaction | Buffer | DNA | TE | NaPPi | ADP | NDP | Water | MMLV-RT |
|---|---|---|---|---|---|---|---|---|
| 1 | 4 μl | — | 2.5 μl | 0.5 μl | 1 μl | 1 μl | 10 μl | 1 μl |
| 2 | 4 μl | 2.5 μl of 40 pg/μl | — | 0.5 μl | 1 μl | 1 μl | 10 μl | 1 μl |
| 3 | 4 μl | 2.5 μl of 100 pg/μl | — | 0.5 μl | 1 μl | 1 μl | 10 μl | 1 μl |
| 4 | 4 μl | 2.5 μl of 200 pg/μl | — | 0.5 μl | 1 μl | 1 μl | 10 μl | 1 μl |

TABLE 33

| Reaction | Amount of DNA | Light Units |
|---|---|---|
| 1 | no DNA tube 1A | 1.166 |
| 2 | no DNA tube 1A | 1.189 |
| 3 | no DNA tube 1A | 1.190 |
| 4 | no DNA tube 1B | 1.071 |
| 5 | no DNA tube 1B | 1.124 |
| 6 | no DNA tube 1B | 1.159 |
| 7 | 10 pg DNA tube 2A | 1.355 |
| 8 | 10 pg DNA tube 2A | 1.498 |
| 9 | 10 pg DNA tube 2A | 1.464 |
| 10 | 10 pg DNA tube 2B | 1.485 |
| 11 | 10 pg DNA tube 2B | 1.519 |
| 12 | 10 pg DNA tube 2B | 1.189 |
| 13 | 25 pg DNA tube 3A | 2.360 |
| 14 | 25 pg DNA tube 3A | 2.159 |
| 15 | 25 pg DNA tube 3A | 2.344 |
| 16 | 25 pg DNA tube 3B | 2.126 |
| 17 | 25 pg DNA tube 3B | 2.087 |
| 18 | 25 pg DNA tube 3B | 2.148 |
| 19 | 50 pg DNA tube 4A | 4.501 |
| 20 | 50 pg DNA tube 4A | 4.920 |
| 21 | 50 pg DNA tube 4A | 4.751 |
| 22 | 50 pg DNA tube 4B | 4.721 |
| 23 | 50 pg DNA tube 4B | 4.809 |
| 24 | 50 pg DNA tube 4B | 4.929 |

TABLE 34

Student's t-Test For DNA Detection

| | p-value |
|---|---|
| 10 pg | 0.002377925 |
| 25 pg | 3.9211E-07 |
| 50 pg | 4.2734E-09 |

Example 21
Detection of Blunt End DNA Fragments Using Reverse Transcriptase and NDPK The following example demonstrates the detection of DNA fragments having blunt ends using reverse transcriptase. A reaction master mix was made containing: 80 µl 5×MMLV-RT Buffer (Promega Part #M531A, Lot #7090101); 10 µl 40 mM Sodium Pyrophosphate (Promega Part #C113A, Lot #6675705); 10 µl 1 µM ADP (Sigma A-5285, Lot #56H7815); 20 µl NDPK (Sigma N-0379, Lot #127F81802 1 U/µl); and 210 µl deionized water.

DNA samples consisted of ladders of blunt-ended DNA fragments in multiples of 25 bp (Promega G451, Lot #84791) and 50 bp (Promega G452, Lot #84796) in 1×TE buffer. These materials were diluted into 1×TE buffer to produce a series of solutions at different DNA concentrations. The reactions were assembled as demonstrated in Table 35. The composition of these components was: MM, Master Mix (described above), and 200 u/µl MMLV-RT (Promega Part #M531A).

These reactions were incubated for 30 min at 37° C. After incubation, 2 µl of the solution was added to 100 µl L/L reagent and the light production of the reaction was measured using a Turner TD-20e Luminometer. The data is presented in Table 35. These data demonstrate that sensitive DNA detection of blunt-ended fragments can be achieved through pyrophosphorolysis of the DNA followed by conversion of ADP to ATP.

TABLE 35

| Rx | MM | DNA | MMLV-RT | Light |
|---|---|---|---|---|
| 1 | 18 µl | 100 ng 25 bp ladder | 1 µl | 142.5 |
| 2 | 18 µl | 20 ng 25 bp ladder | 1 µl | 66.28 |
| 3 | 18 µl | 4 ng 25 bp ladder | 1 µl | 20.33 |
| 4 | 18 µl | 800 pg 25 bp ladder | 1 µl | 5.216 |
| 5 | 18 µl | 160 pg 25 bp ladder | 1 µl | 1.606 |
| 6 | 18 µl | 32 pg 25 bp ladder | 1 µl | 0.902 |
| 7 | 18 µl | — | 1 µl | 0.717 |
| 8 | 18 µl | 100 ng 25 bp ladder | — | 0.571 |
| 9 | 18 µl | 100 ng 50 bp ladder | 1 µl | 149.2 |
| 10 | 18 µl | 20 ng 50 bp ladder | 1 µl | 84.43 |
| 11 | 18 µl | 4 ng 50 bp ladder | 1 µl | 27.56 |
| 12 | 18 µl | 800 pg 50 bp ladder | 1 µl | 6.694 |
| 13 | 18 µl | 160 pg 50 bp ladder | 1 µl | 2.829 |
| 14 | 18 µl | 32 pg 50 bp ladder | 1 µl | 1.323 |
| 15 | 18 µl | — | 1 µl | 0.951 |
| 16 | 18 µl | 100 ng 50 bp ladder | — | 0.751 |

Example 22
Detection of Poly(A) mRNA Using Poly(A) Polymerase

This example demonstrates the detection poly(A) mRNA by the pyrophosphorylation of the poly(A) segment. The reactions were assembled as demonstrated in Table 36. The compositions of the reaction materials was: 10×Buffer-0.5M Tris-HCl, pH 7.5, 0.1M $MgCl_2$, 0.5M NaCl; Globin mRNA GibcoBRL cat#18103-028 (dissolved in $H_2O$); $NaPP_I$, 20 mM sodium pyrophosphate (Promega C113A, in deionized water); poly(A) polymerase, (Sigma P4058, 1 U/µl). These reactions were incubated at 37° C. for 30 min, then 2 µl of the reaction was added to 100 µl of L/L Reagent and the light output of the reaction immediately measured using a Turner TD-20e Luminometer. The data is presented in Table 37. These data demonstrate that poly(A) polymerase is capable of pyrophosphorylating the RNA and that the resulting nucleoside triphosphates can be detected using luciferase, even if only very low levels of RNA are present.

TABLE 36

| Reaction | 10X | Globin | NaPPi | Poly A | Water |
|---|---|---|---|---|---|
| 1 | 2 µl | 1 µl of 50 ng/µl | 1 µl | 1 µl | 15 µl |
| 2 | 2 µl | 1 µl of 10 ng/µl | 1 µl | 1 µl | 15 µl |
| 3 | 2 µl | 1 µl of 2 ng/µl | 1 µl | 1 µl | 15 µl |
| 4 | 2 µl | 1 µl of 400 pg/µl | 1 µl | 1 µl | 15 µl |
| 5 | 2 µl | 1 µl of 80 pg/µl | 1 µl | 1 µl | 15 µl |
| 6 | 2 µl | 1 µl of 16 pg/µl | 1 µl | 1 µl | 15 µl |
| 7 | 2 µl | — | 1 µl | 1 µl | 15 µl |

TABLE 37

| Reaction | Light Units | RNA Present in L/L |
|---|---|---|
| 1 | 772.2 | 5000 pg |
| 2 | 172.3 | 1000 pg |
| 3 | 33.53 | 200 pg |
| 4 | 7.727 | 40 pg |
| 5 | 1.85 | 8 pg |
| 6 | 0.743 | 1.6 pg |
| 7 | 0.594 | — |

Example 23
Detection of Poly(A) mRNA Using Reverse Transcriptase and NDPK This example demonstrates another method for the detection of mRNA, particularly poly(A) mRNA. In this method, a DNA segment is hybridized to the mRNA and the probe is pyrophosphorylated using a reverse transcriptase and pyrophosphate. As the pyrophosphorylation occurs, the deoxynucleoside triphosphates are used to convert ADP to ATP using the enzyme NDPK. The ATP of the final solution is then measured using luciferase.

The reactions were assembled as presented in Table 38. The reaction components were: Buffer, 5×MMLV-RT Buffer (Promega Part #M531A, Lot #7090101); mRNA, Globin mRNA (GibcoBRL cat# 18103-028 dissolved in $H_2O$); Poly (dT), 0.2 µM oligo dT(50), NaPPi, 20 mM Sodium Pyrophosphate, (Promega C113A in deionized water); ADP, 10 mM ADP (Sigma A-5285 Lot #56H7815); NDKP, NDPK, 1 U/µl, (Sigma N-0379 Lot #127F81802); MMLV-RT, (Promega Part #M531A, Lot #7090101) 200 U/µl; and 200 U/µl Superscript II (GibcoBRL cat# 18064-014).

These reactions were incubated at 37° C. for 30 min and 2 µl of the reactions was added to 100 µl of L/L reagent. The light production of the reactions was immediately measured using a Turner TD-20e Luminometer. The data is presented in Table 39.

TABLE 38

| Rx | Buffer | mRNA | Poly (dT) | NaPPi | ADP | NDPK | MMLV-RT | Superscript | Water |
|---|---|---|---|---|---|---|---|---|---|
| 1 | 4 µl | 1 µl of 50 ng/µl | 1 µl | 1 µl | 2 µl | 1 µl | 1 µl | — | 9 µl |

TABLE 38-continued

| Rx | Buffer | mRNA | Poly (dT) | NaPPi | ADP | NDPK | MMLV-RT | Superscript | Water |
|---|---|---|---|---|---|---|---|---|---|
| 2 | 4 μl | 1 μl of 10 ng/μl | 1 μl | 1 μl | 2 μl | 1 μl | 1 μl | — | 9 μl |
| 3 | 4 μl | 1 μl of 2 ng/μl | 1 μl | 1 μl | 2 μl | 1 μl | 1 μl | — | 9 μl |
| 4 | 4 μl | 1 μl of 400 pg/μl | 1 μl | 1 μl | 2 μl | 1 μl | 1 μl | — | 9 μl |
| 5 | 4 μl | 1 μof 80 pg/μl | 1 μl | 1 μl | 2 μl | 1 μl | 1 μl | — | 9 μl |
| 6 | 4 μl | — | 1 μl | 1 μl | 2 μl | 1 μl | 1 μl | — | 9 μl |
| 7 | 4 μl | 1 μl of 50 ng/μl | 1 μl | 1 μl | 2 μl | 1 μl | — | 1 μl | 9 μl |
| 8 | 4 μl | 1 μl of 10 ng/μl | 1 μl | 1 μl | 2 μl | 1 μl | — | 1 μl | 9 μl |
| 9 | 4 μl | 1 μl of 2 ng/μl | 1 μl | 1 μl | 2 μl | 1 μl | — | 1 μl | 9 μl |
| 10 | 4 μl | 1 μl of 400 pg/μl | 1 μl | 1 μl | 2 μl | 1 μl | — | 1 μl | 9 μl |
| 11 | 4 μl | 1 μl of 80 pg/μl | 1 μl | 1 μl | 2 μl | 1 μl | — | 1 μl | 9 μl |
| 12 | 4 μl | — | 1 μl | 1 μl | 2 μl | 1 μl | — | 1 μl | 9 μl |

TABLE 39

| Rx | mRNA | Light Units |
|---|---|---|
| 1 | 5 ng | 647.2 |
| 2 | 1 ng | 425.4 |
| 3 | 0.2 ng | 113.9 |
| 4 | 40 pg | 43.56 |
| 5 | 8 pg | 23.66 |
| 6 | — | 21.52 |
| 7 | 5 ng | 648.5 |
| 8 | 1 ng | 500.4 |
| 9 | 0.2 ng | 144.2 |
| 10 | 40 pg | 45.85 |
| 11 | 8 pg | 28.17 |
| 12 | — | 19.71 |

TABLE 40

| Reaction | AMP | Digest # And μl | Polymer Added | PRPP Synthetase Buffer | PRPP Synthetase | Light Units |
|---|---|---|---|---|---|---|
| 1 | 2 μl of 2.9 e-4M (200 ng) | — | — | 20 μl | 2 μl | 3869 |
| 2 | 2 μl of 2.9e-5M (20 ng) | — | — | 20 μl | 2 μl | 1287 |
| 3 | 2 μl of 2.9e-6M (2 ng) | — | — | 20 μl | 2 μl | 192.9 |
| 4 | 2 μl of 2.9e-7M (200 pg) | — | — | 20 μl | 2 μl | 118.6 |
| 5 | — | 1, 0.2 μl | 5 ng | 20 μl | 2 μl | 48.4 |
| 6 | — | 1, 0.02 μl | 0.5 ng | 20 μl | 2 μl | 14.8 |
| 7 | — | 2, 0.2 μl | 5 ng | 20 μl | 2 μl | 10.9 |
| 8 | — | 2, 0.02 μl | 0.5 ng | 20 μl | 2 μl | 10.6 |
| 9 | — | 3, 0.2 μl | — | 20 μl | 2 μl | 10.3 |
| 10 | — | 3, 0.02 μl | — | 20 μl | 2 μl | 11 |

Example 24

Detection of RNA Using Nucleases, PRPP Synthetase

This example demonstrates the detection of RNA by digestion of RNA by nucleases, transformation of the AMP produced to ATP by PRPP Synthetase, and detection of the ATP produced using luciferase. Three reactions were assembled: Digest 1 (250 ng Globin mRNA and S1 nuclease in a 10 μl reaction); Digest 2 (same as Digest 1, however no S1 nuclease was added); Digest 3 (same as Digest 1, but without globin mRNA). After these digests had incubated 30 min at 37° C., they were used to compose the reactions presented in Table 40. [For the concentrations of these solutions, see descriptions under reaction composition table in Example 16.]

The reactions were incubated for 30 min at 37° C., 100 μl LAR-CoA and 10 ng luciferace were added to each tube, and the light output of the reactions were measured using a Turner TD-20e Luminometer. The data is presented in Table 40. These how that this combination of enzymes can be used to detect relatively low levels of RNA.

Example 25
Improved Detection of Cells Through the Addition of Materials that Allow ATP to be Produced From Enzymes in the Cells One common way to detect the presence of cells is to assay the ATP content of materials which may contain cells. However, such detection methods are limited by the very small concentration of ATP that is present in samples which may contain very few cells. Several types of enzymatic activities are required in every living cell. These activities are involved in the transformation of nucleotides into nucleoside triphosphates for use in cellular metabolism. In particular, the activities known as adenylate kinase and NDPK are widely found in cells. Since these enzymes are expected to exist in all cell lysates, addition of AMP and dCTP should result in the formation of ATP in cell lysates through the reactions:

AMP+dCTP+adenylate kinase→ADP+dCDP

ADP+dCTP+NDPK→ATP+dCDP

If however, the enzymes which remove ATP from such extracts are active enough to remove ATP as it is formed, no build-up of ATP will result.

This example demonstrates that ATP can be detected in cell lysate samples to which AMP and dCTP are added. The nucleoside transformations such as those presented above probably increase ATP concentration. Therefore, lower amounts of cells and cellular materials can be detected by taking advantage of the transformation activity of these enzymes to produce ATP from AMP thereby detecting ATP directly.

A sample of E. coli JM109 was grown in Luria broth for 2 hours. The cells were harvested by centrifugation at 7240×g for 10 min and then resuspended in 1×TBS. The cells were centrifuged again the same way and resuspended in 1×TBS. A sample of the resuspended cells was removed, diluted into sterile Luria broth and plated onto Luria Agar plates to determine the number of cells per microliter of resuspended cell culture. The cell culture was lysed by sonication and the lysate used in the reactions presented in Table 41. After an incubation of 40 min at room temperature, 10 ng luciferase was added to the reactions and the light output of the reactions was immediately measured using a Turner TD 20-e luminometer. The data is presented in Table 41.

TABLE 41

| Reaction | Lysate | AMP (0.1 mM) | dCTP (1 mM) | Buffer* | Light |
|---|---|---|---|---|---|
| 1 | 10 μl** | — | 2 μl | 100 μl | 142 |
| 2 | 10 μl** | 2 μl | — | 100 μl | 69 |
| 3 | 10 μl** | — | — | 100 μl | 67 |
| 4 | — | 2 μl | 2 μl | 100 μl | 4 |
| 5 | 10 μl** | 2 μl | 2 μl | 100 μl | 175 |
| 6 | 1 μl** | 2 μl | 2 μl | 100 μl | 18.85 |
| 7 | 0.1 μl | 2 μl | 2 μl | 100 μl | 4.6 |
| 8 | 0.01 μl | 2 μl | 2 μl | 100 μl | 3.5 |

*Buffer = 100 μl LAR
**Lysate made from resuspended cells at a concentration of $1.8 \times 10^5$ cells/μl. Dilutions of this lysate were made in 1X TBS and 10 μl added to reactions 5, 6, 7, and 8, the amount of initial lysate equivalent to that added is above.

This data shows that addition of dCTP (reaction 1) allows more light to be measured from a cell sample than can be measured if no addition was made to the lysate (reaction 3) or if AMP alone was added to the lysate (reaction 2). However, even more light can be found if both AMP and dCTP is added to the lysate (reaction 5). Dilution of the lysate results in a reduction of the light produced by reactions given AMP and dCTP (reactions 6 and 7). However, the amount of light found is still above the amount expected to present by simple dilution of the lysate. These data then, show that improved cell detection can be demonstrated if additions can be made to the lysate which should result in an increased ATP level in the sample.

Example 26
Optimization of the Concentrations of Nucleotides Added to Form Additional ATP in Cell Lysates Example 25 demonstrates that additional ATP can be detected in cell lysates if materials are added to the lysate. This example demonstrates that the concentration of the material added can be adjusted to produce a substantially higher level of ATP than is originally present in the lysates. A cell lysate produced from a known amount of cells was produced as in Example 25. This new lysate was used in the reactions presented in Table 42. The reactions were incubated for 40 min at room temperature. After incubation, 10 ng of luciferase was added to the reactions and the light output of the reactions was immediately read using a Turner TD-20e luminometer. The data is presented in Table 42.

These data indicate that the concentration of both nucleotides can be co-optimized to obtain light values far superior to those seen in either the lystate without additions or with non-optimal additions.

TABLE 42

| Reaction | Stock AMP Conc. | Stock dCTP Conc. | Lysate | LAR-CoA | Light |
|---|---|---|---|---|---|
| 1 | — | 100 mM | 10 μl* | 100 μl | 144.8 |
| 2 | 80 mM | — | 10 μl* | 100 μl | 1.515 |
| 3 | — | — | 10 μl* | 100 μl | 38.4 |
| 4 | 80 mM | 100 mM | — | 100 μl | 1.743 |
| 5 | 0.1 mM | 1 mM | 10 μl* | 100 μl | 139.4 |
| 6 | 1 mM | 1 mM | 10 μl* | 100 μl | 247.3 |
| 7 | 10 mM | 1 mM | 10 μl* | 100 μl | 569.2 |
| 8 | 80 mM | 1 mM | 10 μl* | 100 μl | 336.7 |
| 9 | 80 mM | 1 mM | 10 μl* | 100 μl | 273.9 |
| 10 | 1 mM | 1 mM | 10 μl* | 100 μl | 283.3 |
| 11 | 1 mM | 10 mM | 10 μl* | 100 μl | 239.6 |
| 12 | 1 mM | 100 mM | 10 μl* | 100 μl | 358.8 |
| 13 | 10 mM | 1 mM | 10 μl* | 100 μl | 666.7 |
| 14 | 10 mM | 10 mM | 10 μl* | 100 μl | 1236 |
| 15 | 10 mM | 100 mM | 10 μl* | 100 μl | 2320 |
| 16 | 80 mM | 1 mM | 10 μl* | 100 μl | 339.8 |
| 17 | 80 mM | 10 mM | 10 μl* | 100 μl | 761.9 |
| 18 | 80 mM | 100 mM | 10 μl* | 100 μl | 1970 |

*Lysate was made from resuspended cells at a concentration of $3 \times 10^4$ cells/ul.
**2 μl of stock used.

Example 27

Time Course of ATP Increase in Lysates Following Addition of Enzyme Substrates

The examples above indicate cell detection sensitivity increased by addition of dCTP and/or AMP followed by an incubation period prior to ATP detection using luciferase. This example demonstrates that detection reaction may be temporally optimized as well.

The cell lysate was made as in Example 25 and was frozen. This lysate was thawed and used to compose the reactions presented in Table 43. Samples were removed from reaction 5 at 1, 5, 15, 30, 60, 90, 120, 150, and 180 min and at 5 min for the other reactions. These samples were added to long luciferase and the light output of the reaction was measured immediately using a Turner TD-20e luminometer. The results from the samples taken at 5 min are presented in Table 43. The results from the samples of reaction 5 taken over time (min) are presented in Table 44.

Note that the that the light output for the reaction rises dramatically over time and reaches final values far above those reported in the previous example. These data indicate that the most sensitive detection of cells will require optimization of the reaction time used for detection in addition to optimization of the added materials.

TABLE 43

| Reaction | Lysate | AMP | dCTP | Light |
|---|---|---|---|---|
| 1 | 10 μl | — | 100 mM | 329 |
| 2 | 10 μl | 10 mM | — | 80.4 |
| 3 | 10 μl | — | — | 241.8 |
| 4 | — | 10 mM | 100 mM | 1.129 |
| 5 | 10 μl | 10 mM | 100 mM | 347.5 |

TABLE 44

| Time (Min) | Light |
|---|---|
| 1 | 136.5 |
| 5 | 347.5 |
| 15 | 1325 |
| 30 | 6379 |
| 60 | 21078 |
| 90 | 33204 |
| 120 | 41470 |
| 150 | 43844 |
| 180 | 36579 |

Example 28

Determination of the Effect of Increasing the Number of DNA Ends on Detection of DNA Through Pyrophosphorylation Reverse transcriptases and DNA polymerases usually bind to DNA segments which can be used as substrates in polymerization reactions. Plasmid DNA has no DNA ends since it is a covalently closed circular molecule. In general, such a molecule would not be expected to undergo pyrophosphorylation unless the DNA is first modified to transform it into a substrate for reverse transcriptase or polymerase. In this example, an experiment is described that confirms that plasmid DNA is not as good a substrate for pyrophosphorylation as digested fragments. In addition, using an enzyme to cleave the DNA which generates more new DNA ends than one that generates fewer ends may improve the detection of the DNA.

The reactions were assembled as presented in Table 45. The components were: Plasmid, pGEM 3ZF(+) (1 mg/ml, Promega corporation, Part #P227A); Buffer, 10×Buffer B (Promega Corporation, Part #R002A); Sau 3AI, Endonuclease Sau 3AI, (Promega Corporation, 8 U/$\mu$l, Part #R619E); Bam H1, Endonuclease Bam H1 (Promega Corporation, 10 U/$\mu$l, Part #R602A). The reactions were incubated at 37° C. for 1 hr, then heated at 70° C. for 10 min, and allowed to cool to room temperature.

The solutions were then added to the reactions presented in Table 46. The reactions were incubated at 37° C. for 20 min. After incubation, 2 $\mu$l of the reaction solution was added to 100 $\mu$l of L/L reagent and the light output of the reactions was immediately measured using a Turner TD-20e luminometer. The data is presented in Table 46.

These data again demonstrate that detection of DNA by pyrophosphorylation is possible. In addition, these data demonstrate that digestion of plasmid DNA is needed prior to treatment using reverse transcriptase. Bam H1 produces only one DNA fragment from the plasmid while Sau 3A produces over 10 fragments from this plasmid. These data demonstrate that light production increases with increasing fragment end number.

TABLE 45

| Solution | Plasmid | Buffer | Water | Sau 3A | Bam H1 |
|---|---|---|---|---|---|
| 1 | 1 $\mu$l | 5 $\mu$l | 44 $\mu$l | — | — |
| 2 | — | 5 $\mu$l | 45 $\mu$l | — | — |
| 3 | — | 5 $\mu$l | 44 $\mu$l | — | 1 $\mu$l |
| 4 | — | 5 $\mu$l | 44 $\mu$l | 1 $\mu$l | — |
| 5 | 1 $\mu$l | 5 $\mu$l | 43 $\mu$l | — | 1 $\mu$l |
| 6 | 1 $\mu$l | 5 $\mu$l | 43 $\mu$l | 1 $\mu$l | — |

TABLE 46

| Reaction | MM | MMLV-RT | Solution | Light |
|---|---|---|---|---|
| Rx1− | 18 $\mu$l | — | 1 $\mu$l #1 | 0.87 |
| Rx1+ | 18 $\mu$l | 1 $\mu$l | 1 $\mu$l #1 | 0.787 |
| Rx2− | 18 $\mu$l | — | 1 $\mu$l #2 | 0.906 |
| Rx2+ | 18 $\mu$l | 1 $\mu$l | 1 $\mu$l #2 | 0.75 |
| Rx3− | 18 $\mu$l | — | 1 $\mu$l #3 | 0.932 |
| Rx3+ | 18 $\mu$l | 1 $\mu$l | 1 $\mu$l #3 | 0.714 |
| Rx4− | 18 $\mu$l | — | 1 $\mu$l #4 | 0.856 |
| Rx4+ | 18 $\mu$l | 1 $\mu$l | 1 $\mu$l #4 | 0.713 |
| Rx5− | 18 $\mu$l | — | 1 $\mu$l #5 | 0.837 |
| Rx5+ | 18 $\mu$l | 1 $\mu$l | 1 $\mu$l #5 | 2.909 |
| Rx6− | 18 $\mu$l | — | 1 $\mu$l #6 | 0.811 |
| Rx6+ | 18 $\mu$l | 1 $\mu$l | 1 $\mu$l #6 | 8.757 |

Example 29

Demonstration of DNA Detection Using Pyrophosphorylation Catalyzed by a Thermostable DNA Polymerase Both reverse transcriptases and DNA polymerases catalyze the addition of nucleotides to a DNA strand. As shown in the earlier examples, reverse transcriptases can be used to catalyze the pyrophosphorylation of DNA thereby allowing its detection using coupled enzymatic reactions. In this example, we demonstrate that DNA polymerases also can be used to catalyze this reaction and that the DNA polymerase from *Thermus aquaticus* (Taq) in fact produces more light from a set amount of input DNA than does the reverse transcriptase.

A master mix (MM) was made which comprised: 10×buffer (Promega Part #M190G, Lot #7675526), 20 $\mu$l, 25 mM MgCl$_2$, 40 $\mu$l, 40 mM Sodium Pyrophosphate, 5 $\mu$l; Taq DNA Polymerase (Promega Part #M166B, Lot #7474623) [storage buffer b], 5 U/$\mu$l, 10 $\mu$l; water, 100 $\mu$l. This solution was mixed by vortex and then used to compose the following reactions: Reactions 1–3 (17.5 $\mu$l master mix, 2.5 $\mu$l 1×TE); Reactions 4–6 (17.5 $\mu$l master mix, 1 $\mu$l 100 pg DNA/$\mu$l [PhiX 174 Hin F1 Fragments, Promega G175A diluted to the concentration listed using 1×TE buffer], 1.5 82 1 1×TE); and Reactions 7–9 (17.5 $\mu$l master mix, 2.5 $\mu$l of 100 pg DNA/$\mu$l). The solutions were mixed and 30 $\mu$l mineral oil was used to cover the aqueous solution. The solutions were incubated at 70° C. for 30 min. Fifteen microliters were removed to which 1 $\mu$l of 1 u/$\mu$l NDPK and 1.5 $\mu$l of 1 uM ADP were added. After an additional 15 min at room temperature, 2.3 $\mu$l of each sample was added to 100 $\mu$l of L/L reagent. The light output of the reactions were immediately measured using a luminometer. The data is presented in Table 47.

These results demonstrate the pyrophosphorylation reaction can be catalyzed by DNA polymerases and that low amounts of DNA may be detected. The values obtained from reactions with 10 and 25 pg DNA are statistically different from the no DNA addition values.

TABLE 47

| Reactions | DNA* | Light Units Measured | | | Mean | Sd. | p-Value** |
|---|---|---|---|---|---|---|---|
| 1–3 | 0 pg | 0.915 | 0.653 | 0.837 | 0.802 | 0.135 | |
| 4–6 | 10 pg | 5.718 | 7.718 | 7.397 | 6.958 | 1.089 | <.0094 |
| 7–9 | 24 pg | 11.8 | 11.18 | 14.79 | 12.59 | 1.93 | <.0086 |

*Amount of DNA present in the luciferase assay tube.
**p value for comparison of the results from no DNA addition to this group. Mentioned in earlier examples, any p value <0.05 is considered a significant difference.

Example 30
Additional DNA Detection Experiments

This example is a direct comparison of the detection of DNA by a reverse transcriptase (MMLV-RT) a thermostable DNA polymerase (Taq Polymerase) and a non-thermostable DNA Polymerase (T4 DNA Polymerase). Also shown is another example of how the particular structure of the DNA fragments utilized in the reaction must be matched to the properties of the DNA modifying enzyme. The enzymes generally fail to produce a signal from supercoiled plasmid DNA since all these enzymes require a DNA end to start their reactions. MMLV-RT and Taq DNA Polymerase utilize DNA species having a 5' overhang but cannot use a DNA having a 3' overhang as a substrate. In contrast, T4 DNA Polymerase utilizes DNA substrates with both 5' overhangs and 3' overhangs. This ability may be due to its 3' exonuclease activity. In addition, this Example shows that reactions using T4 DNA polymerase produce more light than from equivalent reactions with either of the other two enzymes.

The reactions were assembled as presented in Table 48. The solutions were incubated at 37° C. for 1 hr then at 70° C. for 10 min. At this point, 1 µl each reaction was diluted to 20 µl with water to give a concentration of 100 pg DNA/µl. Solution MM was made as follows: 40 µl 5×MMLV-RT Reaction Buffer (Promega Part M531A); 5 µl 40 mM Sodium pyrophosphate; 20 µl 1 µM ADP; 5 µl 1 u/µl NDPK; and 180 µl water. The reactions were mixed and 18 µl were transferred into 8 tubes. One microliter reaction 1 above and 1 µl MMLV-RT (200 u/µl) were added to tubes 1 and 2; 1 µl reaction 2 above and 1 µl MMLV-RT were added to tubes 3 and 4; 1 µl reaction 3 above and 1 µl MMLV-RT were added to tubes 5 and 6; and 1 µl reaction 3 was added to tubes 7 and 8. The tubes were incubated 20 min at 37° C. and then 2 µl of the solutions were added to 100 µl L/L and the light output of the resulting mixture was immediately measured using a Turner TD-20e luminometer. The data is presented in Table 49.

A second MM Mix was made for use with T4 DNA Polymerase as follows: 20 µl 10×Buffer C (Promega Part #R003A); 5 µl 40 mM sodium pyrophosphate; 20 µl 1 µM ADP; 5 µl 1 u/µl NDPK; and 130 µl water. This solution was mixed by vortex and then used to compose the 8 reaction mixtures described in the paragraph above. Incubations were performed at 37° C. for 20 min and then 2 µl of the reaction mixtures were added to 100 µl L/L with luciferase. The light output was immediately measured and the data presented in Table 50 was obtained.

These data show that both of these enzymes can pyrophosphorylate DNA having 5' overhangs. However the T4 DNA polymerase can also pyrophosphorylate DNA having 3' overhangs (produced by Sph I digestion of DNA) while the reverse transcriptase cannot utilize this form of DNA.

A final MM Mix was made containing: 20 µl 10×Taq Buffer (Promega Part #M190G); 40 µl 25 mM MgCl$_2$; 5 µl 40 mM sodium pyrophosphate, and 105 µl water. This new MM Mix was used to produce 8 mixtures. Mixture 1 and 2 contained 17 µl new MM Mix, 1 µl diluted DNA reaction 1, and 2 µl Taq DNA Polymerase (Promega Part #M166B); mixtures 3 and 4 contained 17 µl MM, 1 µl reaction 2, and 2 µl Taq; mixtures 5 and 6 contained 17 µl MM, 1 µl reaction 3, and 2 µl Taq; and mixture 7 and 8 contained 17 µl MM and 1 µl reaction 3. The mixtures were mixed by vortex action, 30 µl mineral oil was placed over the mixture and they were incubated at 70° C. for 20 min. Fifteen microliters of each tube was removed and 1 µl 1 u/µl NDPK and 1.5 µl 1 µM ADP was added to each tube. The tubes were incubated at room temperature for 15 min, 2.3 µl were removed from each reaction and added to 100 µl L/L reagent containing luciferase and the light output of the reactions measured immediately using a luminometer. The data is presented in Table 51.

These data show that Taq DNA Polymerase can utilize DNA having a 5' overhang. However, very little light output results when the DNA has a 3' overhang. Thus, Taq polymerase appears to be similar to MMLV-RT in that it will catalyze the pyrophosphorylation of a DNA if it has a 5' overhang but not if it has a 3' overhang. T4 DNA Polymerase will catalyze pyrophosphorylation with either form of DNA overhang. In addition, by comparing all the data it is clear that much more light is produced if the reactions are performed using T4 polymerase than using either of the other enzymes.

TABLE 48

| Reaction | Buffer | DNA | Bam H1 | Sph 1 | Water |
|---|---|---|---|---|---|
| 1 | 5 µl | 1 µl | — | — | 44 µl |
| 2 | 5 µl | 1 µl | 2 µl | — | 42 µl |
| 3 | 5 µl | 1 µl | — | 2 µl | 42 µl |

The solutions used were: Buffer, Promega Buffer B (Part #R002A); DNA, pGEM 3ZF+ (1 mg/ml) Promega Part #P227A; Bam HI, Promega Bam HI, Part #R602A, Sph I, Promega Sph I, Part #R626A.

TABLE 49

| Reaction | Light Units | DNA Condition | MMLV-RT Added |
|---|---|---|---|
| 1 | 1.472 | supercoiled | + |
| 2 | 1.445 | supercoiled | + |
| 3 | 5.156 | linear, 5' overhang | + |
| 4 | 4.699 | linear, 5' overhang | + |
| 5 | 1.504 | linear, 3' overhang | + |
| 6 | 1.494 | linear, 3' overhang | + |
| 7 | 1.412 | linear, 3' overhang | − |
| 8 | 1.378 | linear, 3' overhang | − |

TABLE 50

| Reaction | Light Units | DNA Condition | T4 DNAP Added |
|---|---|---|---|
| 1 | 2.214 | supercoiled | + |
| 2 | 1.946 | supercoiled | + |
| 3 | 44.46 | linear, 5' overhang | + |
| 4 | 32.53 | linear, 5' overhang | + |
| 5 | 37.29 | linear, 3' overhang | + |
| 6 | 32.11 | linear, 3' overhang | + |
| 7 | 1.446 | linear, 3' overhang | − |
| 8 | 1.361 | linear, 3' overhang | − |

TABLE 51

| Reaction | Light Units | DNA Condition | Taq DNAP Added |
|---|---|---|---|
| 1 | 1.125 | supercoiled | + |
| 2 | 1.174 | supercoiled | + |
| 3 | 8.110 | linear, 5' overhang | + |
| 4 | 9.687 | linear, 5' overhang | + |
| 5 | 1.623 | linear, 3' overhang | + |
| 6 | 1.515 | linear, 3' overhang | + |
| 7 | 1.004 | linear, 3' overhang | − |
| 8 | 1.046 | linear, 3' overhang | − |

Example 31
Detection of Genomic DNA

In this example, high molecular weight DNA is measured using pyrophosphorylation of the DNA, transfer of the terminal phosphate from the dNTPs to ADP to form ATP and measurement of the ATP using luciferase. High molecular weight DNA can be detected at a higher sensitivity if it is first cleaved using endonucleases.

The reactions were assembled as in Table 52. The materials used in the reactions were: Buffer; 10×Multicore Buffer (Promega Part #R999A); Yeast DNA, *S. cerevisiae* DNA (380 μg/ml) (Promega Part #G301A); Mouse DNA (300 μg/ml) (Promega Part #G309A); Eco RI, Endonuclease Eco RI, 12 u/μl, (Promega Part #R601A). The reactions were heated at 37° C. for 60 min then at 70° C. for 10 min. At that point, 1 μl of each of these reactions were diluted to 20 μl by the addition of 19 μl water.

A solution (MM) was made which contained: 24 μl 10×Buffer C (Promega Part #R003A); 6 μl 40 mM Sodium Pyrophosphate, 24 μl 1 μM ADP, 6 μl 1 u/μl NDPK, and 156 μl water. The reactions presented in Table 53 were assembled using this mix.

The added DNAs in the reactions 1A through 10A above refer to the diluted materials from reactions 1–4 described in Table 53. The T4 DNA Pol is T4 DNA Polymerase (Promega Part #M421F). These reactions were incubated at 37° C. for 20 min, then 2 μl of the reactions was added to 100 μl L/L reagent. The light produced by the reactions was immediately measured using a Turner TD-20e luminometer. The data is presented in Table 54. Note that the reactions demonstrate that the system can detect genomic DNA. In addition, Eco RI treatment prior to pyrophosphorylation results in higher light values than are seen without Eco RI pretreatment.

TABLE 52

| Reaction | Buffer | Yeast DNA | Mouse DNA | Water | Eco RI |
|---|---|---|---|---|---|
| 1 | 5 μl | 2.6 μl | — | 42.4 μl | — |
| 2 | 5 μl | — | 3.3 μl | 41.7 μl | — |
| 3 | 5 μl | 2.6 μl | — | 40.4 μl | 2 μl |
| 4 | 5 μl | — | 3.3 μl | 39.7 μl | 2 μl |

TABLE 53

| Reaction | MM | DNA Added | T4 DNA Pol |
|---|---|---|---|
| 1A and 2A | 18 μl | 1 μl #1 | 1 μl |
| 3A and 4A | 18 μl | 1 μl #2 | 1 μl |
| 5A and 6A | 18 μl | 1 μl #3 | 1 μl |
| 7A and 8A | 18 μl | 1 μl #4 | 1 μl |
| 9A | 18 μl | 1 μl #3 | — |
| 10A | 18 μl | 1 μl #4 | — |

TABLE 54

| Reaction Sampled | Light Units | Eco R1 Treatment | T4 DNA Pol Treatment |
|---|---|---|---|
| 1A | 2.424 | − | + |
| 2A | 1.94 | − | + |
| 3A | 1.989 | − | + |
| 4A | 1.665 | − | + |
| 5A | 12.27 | + | + |
| 6A | 11.9 | + | + |
| 7A | 23.23 | + | + |
| 8A | 20.26 | + | + |
| 9A | 0.651 | + | − |
| 10A | 0.724 | + | − |

Example 32
Optimization of ADP Concentrations Used in DNA Detection by Pyrophosphorylation In this example, we examine the effect of varying the ADP concentration on the detection of DNA by the T4 DNA Polymerase catalyzed pyrophosphorylation of the DNA and transfer of the terminal phosphates of the dNTPs to ADP using NDPK. Increasing the concentration of ADP increases the background seen without ATP addition. Increasing the ADP concentration also can increase the signal seen upon DNA phosphorylation. An optimal amount of added ADP can be determined by selecting the concentration of ADP which results in the best fold increase in signal over background.

ADP (Sigma potassium ADP, A-5285, Lot #56H7815) was dissolved in distilled water to various concentrations ranging from 0.2 to 20 μM. The Bam HI digest of pGEM 3ZF+ described in example 26 was used to form a reaction solution (solution MM) composed of: 40 μl 10×Buffer C (Promega Part #R003A), 10 μl of 40 mM sodium pyrophosphate; 10 μl 1 u/μl of NDPK; 1 μl 20 ng/μl Bam HI digested pGEM 3ZF+; and 299 μl of water. These solutions were used to compose the reactions presented in Table 55.

As ADP concentration increases, the total light value increases for both the reactions containing polymerase and those without polymerase as demonstrated in Table 56. In this example the best fold increase in the signal, as defined as fold increase in signal over background, is seen with 0.05 μM ADP in the pyrophosphorylation reaction.

TABLE 55

| Reaction | μM | T4 DNA Pol | ADP |
|---|---|---|---|
| 1, 2 | 18 μl | 1 μl | 1 μl of 0.2 uM |
| 3 | 18 μl | — | 1 μl of 0.2 μM |
| 4, 5 | 18 μl | 1 μl | 1 μl of 1 μM |
| 6 | 18 μl | — | 1 μl of 1 μM |
| 7, 8 | 18 μl | 1 μl | 1 μl of 2 μM |
| 9 | 18 μl | — | 1 μl of 2 μM |
| 10, 11 | 18 μl | 1 μl | 1 μl of 10 μM |
| 12 | 18 μl | — | 1 μl of 10 μM |
| 13, 14 | 18 μl | 1 μl | 1 μl of 20 μM |
| 15 | 18 μl | — | 1 μl of 20 μM |

The T4 DNA Pol used was Promega T4 DNA Polymerase (10 u/μl) (Pt# M421F).

TABLE 56

| Reaction | Light | ADP | DNA | Avg. | Blank Avg. .... | Fold Above No Polymerase |
|---|---|---|---|---|---|---|
| 1 | 9.19 | 0.01 μM | + | 8.81 | 8.317 | 16.9 |
| 2 | 8.43 | 0.01 μM | + | | | |
| 3 | 0.43 | 0.01 μM | − | | | |
| 4 | 28.36 | 0.05 μM | + | 29.05 | 28.39 | 42.9 |
| 5 | 29.74 | 0.05 μM | + | | | |
| 6 | 0.662 | 0.05 μM | − | | | |
| 7 | 43.29 | 0.10 μM | + | 41.54 | 40.18 | 29.6 |
| 8 | 39.78 | 0.10 μM | + | | | |
| 9 | 1.359 | 0.10 μM | − | | | |
| 10 | 77.4 | 0.50 μM | + | 74.9 | 68.9 | 11.5 |
| 11 | 72.49 | 0.50 μM | + | | | |
| 12 | 5.969 | 0.50 μM | − | | | |
| 13 | 82.4 | 1.0 μM | + | 80.1 | 69.38 | 6.42 |
| 14 | 77.98 | 1.0 μM | + | | | |
| 15 | 10.81 | 1.0 μM | − | | | |

Example 33
Detection of ATP Using Fluorescence-Based Methods

In addition to detecting ATP by luciferase-based methods, ATP can be detected using fluorescence-based systems. For the fluorescence-based measurements, an ATP determination kit was used (Sigma #366-A Lot#117H6017). This kit uses a combination of phosphoglycerate kinase and glyceraldehyde phosphate dehydrogenase, to catalyze the formation of NAD from NADH in the presence of ATP. Since the NADH is fluorescent, but the NAD is not, ATP can be measured as a loss in fluorescence intensity. The reaction buffer was prepared from kit components as follows : 3 ml supplied buffer solution was diluted in 5.25 ml nanopure water, and 0.75 ml 12% trichloroacetic acid was added. One vial of the supplied NADH was reconstituted in 1 ml nanopure water; the enzyme mix was used as supplied. For each measurement, 10 μl enzyme mix and 20 μl NADH were added to 1.5 ml of reaction buffer in a clear plastic 10 mm cuvette. Fluorescence was read in a SPEX Fluorolog Fluorimeter using SPEX dm3000 Software, with absorbance and emission wavelengths set at 340 nm and 460 nm, respectively.

ATP samples at various concentrations were prepared by serially diluting ATP tenfold into 10 mM Tris, pH 7.3. Varying amounts of each dilution was added to the cuvette and the decrease in fluorescence was recorded (Table 57). For comparison ATP was also quantitated using luciferase. 20 μl of each ATP dilution was added to 100 μl LAR with 10 ng luciferase and light output was measured using a TD-20e luminometer. Each dilution was measured in duplicate (Table 58).

This example indicates that ATP can be detected by at least two separate methods. In the fluorescence-based system, changes of approximately 200,000 fluorescent light units were significant, which corresponds to 1 nanomole ATP. The luciferase assay was sensitive to lower levels of ATP.

TABLE 57

| ATP Concentration | Volume Added | Mass Added | Decrease In Fluoresceuce Units In 10,000's | | |
|---|---|---|---|---|---|
| 10 mM | 20 μl | 200 nmoles | 135 | nd[a] | nd[a] |
| 1 mM | 20 μl | 20 nmoles | 84.3 | 132 | nd[a] |
| 1 mM | 10 μl | 10 nmoles | 89.3 | nd[a] | nd[a] |
| 1 mM | 5 μl | 5 nmoles | 76.4 | nd[a] | nd[a] |
| 100 μM | 40 μl | 4 nmoles | 66.7 | 60.2 | nd[a] |
| 100 μM | 20 μl | 2 nmoles | 23.9 | 21.9 | 20.8 |
| 100 μM | 10 μl | 1 nmole | 19.1 | 22.0 | 18.9 |
| 100 μM | 5 μl | 500 pmoles | 7.6 | 6.9 | 6.8 |
| 10 μM | 20 μl | 200 pmoles | 11.6 | 10.0 | 11.1 |
| 10 μM | 10 μl | 100 pmoles | 10.4 | 6.9 | 6.6 |
| 1 μM | 20 μl | 20 pmoles | 8.2 | 8.4 | 5.2 |
| 1 μM | 10 μl | 10 pmoles | 8.0 | 8.1 | 5.3 |
| 0.1 μM | 20 μl | 2 pmoles | 3.2 | 5.6 | 3.6 |
| 0.01 μM | 20 μl | 200 fmoles | 8.1 | 9.7 | 6.8 |
| Tris | 20 μl | — | 4.3 | 3.7 | 3.8 |
| Tris | 10 μl | — | 4.0 | 3.3 | 3.5 | nd, not done

TABLE 58

| ATP, 20 μl Of | Light Units | |
|---|---|---|
| 10 mM | 102,417 | 102,731 |
| 1 mM | 117,718 | 98,842 |
| 100 μM | 47,676 | 44,101 |
| 10 μM | 7690 | 6998 |
| 1 μM | 812 | 798 |
| 0.1 μM | 76.8 | 67.8 |
| 0.01 μM | 7.0 | 4.5 |
| Tris | 0.06 | 0.06 |

Example 34
Detection of ATP Using Fluorescence; PRPP Synthetase, Reactions with Adenosine Monophosphate ATP was synthesized by the enzyme PRPP Synthetase from the substrates AMP and PRPP as in Example 13, except the reactions were done in larger volumes and the substrates were at higher concentrations. Twenty μl AMP (29 mM) and 20 μl PRPP (26 mM) were incubated with 20 μl PRPP Synthetase ($6 \times 10^{-3}$ units) in 200 μl PRPP Synthetase buffer. The reactions are summarized in Table 59. After a 30 minute incubation at 37° C., the PRPP Synthetase was heat-inactivated at 94° C. 10 min. The ATP was then quantitated using both a fluorescence-based system and a luciferase-based system. For the fluorescence-based measurements, an ATP determination kit was used (Sigma #366-A Lot#117H6017) as described in Example 33. Twenty microliter aliquots of the PRPP reactions were then added to cuvettes containing 1.5 ml buffer, 10 μl enzyme mix and 20 μl NADH. The decrease in fluorescence was monitored. Four to six measurements were made for each reaction (Table 60). For the luciferase-based assay, 20 μl was added to 100 μl LAR and 10 ng luciferase. Each reaction was determined in triplicate. Light output was measured using a Turner TD-20e luminometer (Table 61). This example demonstrates that ATP production by PRPP Synthetase can be measured using fluorescence or luciferase.

TABLE 59

| Reaction | PRPP Syn Buffer | AMP | PRPP | PRPP Synthetase |
|---|---|---|---|---|
| 1 | 200 μl | 20 μl | 20 μl | 20 μl |
| 2 | 200 μl | 20 μl | — | 20 μl |
| 3 | 200 μl | — | 20 μl | 20 μl |
| 4 | 200 μl | 20 μl | 20 μl | — |

TABLE 60

| Reaction | Decrease In Fluorescence Units (In 10,000's) | | | | | | Average |
|---|---|---|---|---|---|---|---|
| 1 | 49.1 | 48.0 | 47.3 | 49.0 | nd[a] | nd[a] | 48.4 |
| 2 | 2.48 | 3.30 | 2.37 | 10.9 | 7.06 | 9.57 | 5.95 |
| 3 | 3.36 | 2.30 | 11.06 | 7.63 | 10.5 | nd[a] | 6.97 |
| 4 | 3.48 | 1.68 | 4.83 | 0.62 | 5.74 | 3.37 | 3.29 |

TABLE 61

| Reaction | Light Units | | |
|---|---|---|---|
| 1 | 8923 | 9995 | 9562 |
| 2 | 0.001 | 0.000 | 0.013 |
| 3 | 1939 | 1760 | 1770 |
| 4 | 27.9 | 23.7 | 23.0 |

Example 35
Detection of ATP Using Fluorescence; Cell Lysates

ATP can also be generated by incubating cell lysates with AMP and dCTP as described in Examples 25, 26 and 27. The Sigma ATP determination kit described in Example 33 was also used to detect ATP in this system. Reactions were assembled as described below (Table 62) and incubated at room temperature. ATP concentrations were quantitated at 80 minutes and 140 minutes using luciferase. In this assay 15 μl each reaction was added to 100 μl LAR and 10 ng luciferase. Light output was measured using a Turner Luminometer TD-20e (Table 63). During the time course, ATP was also measured by fluorescence. The procedure was as described in Example 33, except that 15 μl each reaction was added per reading, instead of 20 μl. The first set of time points began at 80 min; the second set of readings began at 140 min. Each reaction was assayed in duplicate or triplicate (Table 64). This example demonstrates that ATP synthesized in cell lysates can be detected using a luciferase or a fluorescence assay.

TABLE 62

| Reaction | E. coli Lysate | 0.05M MgSO$_4$ | 10 mM AMP | 100 mM dCTP |
|---|---|---|---|---|
| 1 | 100 μl | 20 μl | 20 μl | 10.5 μl |
| 2 | — | 20 μl | 20 μl | 10.5 μl |
| 3 | 100 μl | — | 20 μl | 10.5 μl |
| 4 | 100 μl | 20 μl | — | 10.5 μl |
| 5 | 100 μl | — | — | 10.5 μl |

TABLE 63

| | Light Units | |
|---|---|---|
| Reactions | T = 80 Minutes | T = 140 Minutes |
| 1 | 33,519 | 65,522 |
| 2 | 2.158 | 2.086 |
| 3 | 362.7 | 370.6 |
| 4 | 0.5 | 0.561 |
| 5 | 1.898 | 1.057 |

TABLE 64

| | Decrease In Fluorescence Units (In 10,000's) | | | |
|---|---|---|---|---|
| Reaction | First Time Point | | Second Time Point | |
| 1 | 27.1 | 29.4 | 83.8 | 87.3 |
| 2 | 11.9 | 8.2 | 1.3 | 1.2 |
| 3 | 12.2 | 8.2 | 4.1 | 4.7 |
| 4 | 5.0 | 4.1 | 4.2 | 2.8 |
| 5 | nd[a] | nd[a] | 4.8 | 7.3 |

[a]nd, not done.

Example 36
Extremely Sensitive DNA Measurement by Amplification of Pyrophosphorylation Reaction Products This Example demonstrates that AMP can be a source of extraneous nucleotides that result in unwanted background amplification in reactions spiked with a nucleoside triphosphate and that the detection limit for DNA measured through the pyrophosphorylation of the sample can be lowered if the products are amplified.

Two reactions were assembled. Reaction 1 consisted of: 2 μl 10×Buffer C (Promega Corp. R003A, Lot 7544205); 0.5 μl 40 mM sodium pyrophosphate; 2 μl of 1 mM AMP; 1 μl 0.25 u/μl Myokinase (Sigma M3003, Lot 116H9516); 1 μl 0.17 u/μl Pyruvate Kinase (Sigma N 0379, Lot 127F81802); 1 μl 10 u/μl T4 DNA Polymerase (Promega M421F Lot 617506) and 11.5 μl water. Reaction 2 was identical to Reaction 1 except that the AMP was treated with Apyrase in a reaction consisting of 20 μl 10 mM AMP and 1 μl 1 u/μl Apyrase (Sigma A 6535 lot 127H7010) for 30 min at room temperature, followed by a heat inactivation step to eliminate the Apyrase activity by treatment at 70° C. for 10 min.

At time 0, 1 μl 10 mM PEP was added to each reaction and the reaction was mixed and incubated at room temperature. At 2 min, 2 μl of the reaction was removed and added to 100 μl L/L reagent and the light output measured using a Turner TD-20e Luminometer as described above. The following data were collected: Reaction 1; 817.4 light units, Reaction 2; 7.3 light units. Since there should be no ATP produced by this reaction unless extraneous nucleoside di- or triphosphate is added as a contaminant in a reagent, this demonstrates that the AMP probably contained some level of contaminating nucleotide which was eliminated by Apyrase treatment.

The following reactions were assembled: Reaction A contained the components described in Reaction 2 above except that 1 μl of 1 ng HinF 1 Fragments (Promega Corp, G175A Lot 7733602) diluted to this concentration with 1×TE Buffer/μl was added and the T4 DNA Polymerase was not added to the initial reaction mix; Reaction B, same as Reaction A but the DNA added was at a concentration of 100 pg DNA/μl; Reaction C, same as Reaction A but the DNA added was at a concentration of 10 pg DNA/μl; Reaction D, same as Reaction A but the DNA added was at a concentration of 1 pg DNA/μl; and, Reaction E, same as Reaction A but with 1 μl 1×TE Buffer added and no DNA added.

One microliter of T4 DNA Polymerase was added to each reaction and the reactions were incubated at 37° C. for 15 min. After this incubation, 1 μl 10 mM PEP was added to each reaction and incubated again at room temperature 10 min. At that time, 2 μl each reaction was added to 100 μl L/L reagent and the light output of the reaction was measured using a Turner Luminometer as described above. The data are presented in Table 65. This Example demonstrates that the products of the pyrophosphorylation reaction can be coupled to an ATP amplification system to increase the sensitivity of DNA measurement.

TABLE 65

| | | Light Measured From Samples Incubated At Room Temperature | |
|---|---|---|---|
| Reaction | pg DNA* | 10 Min | 20 Min |
| A | 100 pg | 917.3 | 1156 |
| B | 10 pg | 112.1 | 1119 |
| C | 1 pg | 4.68 | 919 |
| D | 0.1 pg | 2.61 | 873 |
| E | 0 | 1.52 | 650 |

*The DNA reported in this column is the actual DNA equivalent luciferase reaction. The amount is approximately 10% of the total pyrophosphorylated.

Example 37
Detection of a Specific Message by Use of a DNA Primer Exactly Matching the Message Sequence and Lack of a Signal when the DNA Primer is Mismatched at its 3' End In this Example, a luciferase light signal is generated from pyrophosphorylation of a DNA primer that complements the sequence of an RNA species. In addition, evidence is presented to demonstrate that this signal is not generated if the 3' terminal base of the primer does not complement the RNA base in the message sequence. This data demonstrates that primer pyrophosphorylation can be used to detect the presence of specific RNA sequences and that mutations at specific bases in the message can be detected by use of primers that should match the base but that do not give a signal with the message.

A master reaction mix was assembled which contained:

| Capped Kanamycin RNA (0.62 mg/ml) | 1.25 μl |
|---|---|
| 5X MMLV Reaction Buffer | 50 μl |

-continued

| | |
|---|---|
| 40 mM Sodium Pyrophosphate | 2.5 µl |
| 10 µM ADP | 2.5 µl |
| NDPK (1 u/µl) | 5 µl |
| MMLV-RT (200 u/µl) | 12.5 µl |
| Nanopure water | 163.75 µl |

Primers corresponding to SEQ ID NO:1 through 4 (see Table 93 for SEQ ID NOS and primer sequences) were dissolved at a concentration of 1 mg/ml in 1×TE buffer.

Nineteen microliters of the master reaction mix was placed in 10 labeled 0.5 ml tubes and the following additions were made to the tubes: Tubes 1 and 2, 1 µl 1×TE Buffer; Tubes 3 and 4, 1 µl Primer 1, Tubes 5 and 6, 1 µl Primer 2 (SEQ ID NO:2); Tubes 7 and 8, 1 µl Primer 3 (SEQ ID NO:3), and; Tubes 9 and 10, 1 µl Primer 4 (SEQ ID NO:4). Primer 1 was designed to exactly complement a segment of the coding region of the Kanamycin RNA, Primers 2, 3 and 4 were designed to match the sequence of Primer 1 except that the 3' terminal base of the primer was altered to one of each of the other three DNA bases at this position.

The 10 0.5 ml microfuge tubes were incubated at 37° C. 20 min and then 2 µl of the contents of the tubes was added to 100 µl L/L reagent and the light output of the reagent was measured using a luminometer. The following data was collected.

| Tube | Relative Light Units |
|---|---|
| 1 | 3.989 |
| 2 | 3.458 |
| 3 | 49.95 |
| 4 | 52.24 |
| 5 | 3.779 |
| 6 | 4.394 |
| 7 | 4.163 |
| 8 | 7.879 |
| 9 | 7.811 |

These data show that MMLV-RT is able to pyrophosphorylate a DNA primer that hybridized internally to a RNA sequence and that the free nucleoside triphosphates that are formed can be converted to ATP equivalents that can be measured using luciferase. In addition, the data show that this signal is either absent or much weaker when a primer with a 3' mismatch to the expected base is used in the reaction.

Example 38
Detection of a Specific RNA; Globin mRNA

In this Example, the light signal produced from pyrophosphorylation of DNA primers that are complementary to two regions of globin mRNA is compared to the signals from two DNA primers that are the exact sequence of the same regions. Once again, primers that complement the RNA are shown to give a signal above background, whereas those that do not complement the RNA give little or no signal.

Primers 5–8 (SEQ ID NOS:5,6,17,18) shown in the primer sequence listing were diluted to a concentration of 0.5 mg/ml in 1×TE buffer. Purified globin mRNA (GibcoBRL #18103-028) was dissolved in 1×TE buffer to a concentration of 20 ng/1 µl.

Hybridization solutions were assembled as follows:
Solution 1 10 µl Primer 5 and 10 µl Globin mRNA
Solution 2 10 µl Primer 6 and 10 µl Globin mRNA
Solution 3 10 µl Primer 7 and 10 µl Globin mRNA
Solution 4 10 µl Primer 8 and 10 µl Globin MRNA
Solution 5 10 µl Primer 5 and 10 µl 1×TE Buffer
Solution 6 10 µl Primer 6 and 10 µl 1×TE Buffer
Solution 7 10 µl Primer 7 and 10 µl 1×TE Buffer
Solution 8 10 µl Primer 8 and 10 µl 1×TE Buffer
Solution 9 10 µl 1×TE Buffer and 10 µl Globin mRNA These solutions were assembled in 0.5 ml tubes, heated to 50° C. for 15 min and allowed to cool to room temperature for 15 min on a laboratory bench.

The following master reaction mixture was assembled:

| | |
|---|---|
| Nanopure water | 346.5 µl |
| MMLV-RT 5X Reaction Buffer | 132 µl |
| Sodium pyrophosphate (Promega M531, lot 7090105) | 16.5 µl |
| NDPK (1 u/µl) | 33 µl |
| ADP (2 µM) | 33 µl |
| MMLV-RT (adjusted to 100 u/µl) | 33 µl |

The solution above was mixed and 18 µl placed into 27 tubes. Three two-microliter samples of each of the hybridization solutions above were added in three of the tubes containing the master reaction mix and the tubes were then incubated at 37° C. for 15 min. The contents of the tubes were then added to 100 µl of L/L reagent and the light production of the resulting reaction was measured using a Luminometer (Turner 20/20).

The following results were obtained:

TABLE 66

| Hybridization Solution | Light Values | | | Average |
|---|---|---|---|---|
| Primer 5 + RNA | 6.555 | 6.303 | 6.187 | 6.348 |
| Primer 5 + TE Buffer | 6.335 | 5.923 | 6.046 | 6.101 |
| Primer 6 + RNA | 137.8 | 128.5 | 169.2 | 145.2 |
| Primer 6 + TE Buffer | 10.24 | 9.429 | 9.858 | 9.842 |
| Primer 7 + RNA | 6.235 | 6.763 | 6.375 | 6.458 |
| Primer 7 + TE Buffer | 6.436 | 6.545 | 6.138 | 6.388 |
| Primer 8 + RNA | 90.34 | 95.42 | 54.7 | 80.15 |
| Primer 8 + TE Buffer | 10.21 | 12.55 | 9.372 | 10.71 |
| TE Buffer + RNA | 5.579 | 6.509 | 6.388 | 6.159 |

These data show that a strong light signal is seen when the reaction mixes containing primers 6 or 8 and RNA are added to the L/L reagent but little signal is seen when the primers are incubated without RNA, or when the RNA is incubated without these primers. In addition, primers 5 and 7 give very low signals in the presence or absence of added RNA. Primers 6 and 8 were designed to complement two different regions in the coding region of globin mRNA. Primers 5 and 7 were made to exactly mimic the sequence of these same RNA regions. Thus, these data provide a second example of how the pyrophosphorylation of a primer can be used to detect a specific RNA.

Example 39
Specific Detection of RNA: Comparison of Signals From RNA Species That Match Primer Sequences to Those From Random RNA To detect specific RNA using the pyrophosphorylation reaction described in the previous Example it is necessary that the primers should not give a strong signal with RNA species that do not contain the sequence to be detected. In this Example, the strength of the signal of primers designed to detect globin mRNA will be compared to the signal seen when these primers are used in reactions with yeast total RNA.

Primers 6 and 8 and Oligo (dT)(Promega, C110A) were diluted to a concentration of 0.5 mg/ml in 1×TE buffer.

Globin mRNA (GibcoBRL #18103-028) was dissolved in 1×TE buffer to a concentration of 20 ng/µl. Yeast RNA (Sigma Chemical Co. R3629) was dissolved in 1×TE buffer to a concentration of 20 ng/µl.

Hybridization solutions were assembled as follows:

10 µl Oligo dT and 10 µl Globin mRNA

10 µl Primer 6 and 10 µl Globin mRNA

10 µl Primer 8 and 10 µl Globin mRNA

10 µl 1×TE and 10 µl Globin mRNA

10 µl Oligo dT and 10 µl Yeast RNA

10 µl Primer 6 and 10 µl Yeast RNA

10 µl Primer 8 and 10 µl Yeast RNA

10 µl 1× TE and 10 µl Yeast RNA

These solutions were assembled in 0.5 ml tubes, heated to 50° C. for 15 min and then allowed to cool to room temperature for 15 min.

The following master reaction mixture was assembled:

| | |
|---|---|
| Nanopure water | 346.5 µl |
| MMLV-RT 5X Reaction Buffer | 132 µl |
| Sodium pyrophosphate (Promega M531, lot 7090105) | 16.5 µl |
| NDPK (1 u/µl) | 33 µl |
| ADP(2 uM) | 33 µl |
| MMLV-RT (adjusted to 100 u/µl) | 33 µl |

The solution above was mixed and 18 µl placed into 24 tubes. Three two-microliter samples of each of the hybridization solutions above were added in three of the tubes containing the master reaction mix and the tubes were incubated at 37° C. for 15 min. The contents of the tubes were then added to 100 µl of L/L reagent and the light production of the resulting reaction was measured using a Luminometer (Turner 20/20).

The following data were obtained:

TABLE 67

| Hybridiztion Solution | | | | | |
|---|---|---|---|---|---|
| RNA | Primer | Light Units | | | Average |
| Globin RNA | Oligo dT | 614.1 | 680.6 | 657.7 | 650.8 |
| Globin RNA | Primer 6 | 93.29 | 92.19 | 92.9 | 92.79 |
| Globin RNA | Primer 8 | 77.13 | 61.69 | 69.89 | 69.57 |
| Globin RNA | none | 4.11 | 4.07 | 3.92 | 4.03 |
| Yeast RNA | Oligo dT | 2.05 | 2.13 | 2.22 | 2.13 |
| Yeast RNA | Primer 6 | 4.25 | 4.15 | 4.46 | 4.28 |
| Yeast RNA | Primer 8 | 6.21 | 4.83 | 4.37 | 5.14 |
| Yeast RNA | none | 1.97 | 1.53 | 1.97 | 1.81 |

These data show that much higher signals result when the primers are incubated with globin mRNA than when the primers are incubated with yeast total RNA. Since the yeast RNA should not contain the globin sequence, the lack of a high signal is expected. The fact that oligo (dT) also gives a low signal suggests that most of the RNA in this preparation is not mRNA, but other forms of RNA.

Example 40

Specific Detection of RNA: Comparison of Signals From RNA Species That Match Primer Sequences in Reactions with and without Added Extraneous RNA For the pyrophosphorylation reaction described in Example 38 to be used to detect specific messages, another requirement of the system is that the primers should give a very similar signal in the presence and absence of extraneous RNA. In this Example, the strength of the signal of primers designed to detect globin mRNA in the presence of a large amount of yeast RNA will be compared to the signal seen in the absence of added yeast RNA.

Hybridization solutions containing various levels of yeast RNA, primer 6 or primer 8 and globin mRNA were assembled by adding 5 µl 500 ng/µl either primer 6 or primer 8 to 5 µl 40 ng/µl of globin mRNA and 10 µl yeast RNA (Sigma Chemical Co. R3629) in 1×TE buffer to produce solutions containing total amounts of yeast RNA of 0, 2, 20, 200, 400, and 800 ng. The solutions were heated at 50° C. for 15 min and then allowed to cool to room temperature for 15 min.

Reaction master mix was assembled as in Example (38) above and 18 µl of the mix was placed in 18 tubes. After cooling 15 min, 2 µl of the various hybridization solutions containing primer 6 were added to the tubes and the tubes were placed in a 37° C. heating block.

After 15 min of incubation of the hybridization mixture with the reaction master mix, 20 µl of the solution was added to 100 µl of L/L and the light output of the resulting reaction was measured using a Turner TD-20/20 Luminometer.

After the primer 6 data was collected, an identical set of reactions was performed using the hybridization solutions containing primer 8.

The following data were obtained:

TABLE 68

| Primer 6 Reactions | | | | |
|---|---|---|---|---|
| Yeast RNA | Light Output | | | Average |
| None | 96 | 109 | 111 | 105.3 |
| 2 ng | 98.4 | 85.0 | 118.5 | 100.7 |
| 20 ng | 117.9 | 110.9 | 82.7 | 103.65 |
| 200 ng | 56.4 | 110.1 | 93.2 | 86.6 |
| 400 ng | 115.7 | 110.7 | 124.6 | 117 |
| 800 ng | 127.6 | 128.7 | 143.1 | 133.1 |

TABLE 69

| Primer 8 Reactions | | | | |
|---|---|---|---|---|
| Yeast RNA | Light Output | | | Average |
| None | 105.8 | 97.0 | 82.3 | 95.0 |
| 2 ng | 84.5 | 84.6 | 93.7 | 87.6 |
| 20 ng | 99.6 | 111.7 | 104.9 | 105.4 |
| 200 ng | 83.6 | 75.9 | 95.6 | 85.1 |
| 400 ng | 94.7 | 97.2 | 81.9 | 91.2 |
| 800 ng | 50.7 | 89.0 | 82.1 | 73.9 |

These data indicate that addition of very large amounts of yeast RNA to the hybridization reaction does not greatly lower the signal from primers for specific RNA species.

Example 41

Mutation Detection Using Primers to Globin mRNA #1: Detection of Mismatched Bases at the 3' End of the Primer Sequence The pyrophosphorylation reactions for RNA detection, such as shown with Primer 6 and Primer 8, require that the primer be pyrophosphorylated by an added polymerase. If the 3' end of the primer contains a base that does not match the RNA, it might not be a substrate for the pyrophosphorylation reaction. If this is the case, addition of a primer which should detect the presence of an RNA species to reactions containing a sample that should contain the RNA might indicate that the RNA is altered in sequence at the base which matches the 3' end of the primer. Substitution of a new primer that contains the complementary base to the altered RNA sequence then should restore the signal. In this way, the pyrophosphorylation reaction may be used to interrogate the sequence of RNA species in the region matching the 3' end of the primer. To test this concept, primers were designed that were identical in sequence to Primer 6 and Primer 8, with the exception that the 3' base of these primers were varied to one of each of the other three DNA bases. This Example demonstrates the use of such a primer set for confirming that the RNA base at the 3' end of the primer matches the expected base by generating a light signal in the pyrophosphorylation reaction but that the other primers with altered 3' bases do not generate this signal.

The primers 6m1 through 6m3 (SEQ ID NOS:7, 8 and 9) were dissolved in 1×TE buffer to a concentration of 500 ng/μl.

Hybridization solutions containing primer 6 through primer 6m3 or primer 8 through primer 8m3 (SEQ ID NO:18, 19, 20 and 21) were assembled by adding 5μl of 20 ng/μl of globin mRNA or Tris buffer. The solutions were heated at 50° C. for 15 min then allowed to cool to room temperature for 15 min.

Reaction master mix was assembled as in Example 38 above and 18 μl of the mix was placed in 18 tubes. After cooling for 15 min, 2 μl of the various hybridization solutions containing primer 6 through primer 6m3 were added to the tubes and the tubes were placed in a 37° C. heating block.

After a 15 min incubation at 37° C. of the hybridization mixes with the Reaction Master Mix, 20 μl the reaction was added to 100 μl L/L reagent and the light output of the reaction measured immediately. The following data were recorded:

TABLE 70

| Primer | RNA (+/−) | Light Units | | | Average |
|---|---|---|---|---|---|
| Primer 6 | + | 157.3 | 150 | 130.5 | 149.9 |
| Primer 6 | − | 16.2 | 13.3 | 11.1 | 13.6 |
| Primer 6m1 | + | 7.3 | 7.4 | 7.5 | 7.4 |
| Primer 6m1 | − | 6.8 | 6.7 | 6.7 | 6.7 |
| Primer 6m2 | + | 7.9 | 8.8 | 9.2 | 8.7 |
| Primer 6m2 | − | 7.9 | 7.3 | 6.5 | 7.2 |
| Primer 6m3 | + | 6.9 | 7.4 | 7.4 | 7.2 |
| Primer 6m3 | − | 6.1 | 6.8 | 7.2 | 6.7 |
| (no primer) | + | 7.0 | 6.3 | 7.4 | 6.9 |

Reaction master mix was again assembled as in Example 38 above and 18 μl of the mix was placed in 18 tubes. After cooling for 15 min, 2 μl of the various hybridization solutions containing primer 8 through primer 8m3 were added to the tubes and the tubes were placed in a 37° C. heating block.

After a 15 min incubation at 37° C. of the hybridization mixes in the Reaction Master Mix, 20 μl of the reaction was added to 100 μl L/L reagent and the light output of the reaction measured immediately. The following data were recorded:

TABLE 71

| Primer | RNA (+/−) | Light Units | | | Average |
|---|---|---|---|---|---|
| Primer 8 | + | 29.1 | 28.7 | 25.2 | 27.66 |
| Primer 8 | − | 5.0 | 4.3 | 5.9 | 5.1 |
| Primer 8m1 | + | 2.5 | 2.5 | 2.5 | 2.5 |
| Primer 8m1 | − | 2.3 | 2.2 | 2.4 | 2.3 |
| Primer 8m2 | + | 7.4 | 7.1 | 5.9 | 6.8 |

TABLE 71-continued

| Primer | RNA (+/−) | Light Units | | | Average |
|---|---|---|---|---|---|
| Primer 8m2 | − | 2.0 | 2.1 | 2.1 | 2.1 |
| Primer 8m3 | + | 3.4 | 2.5 | 2.4 | 2.8 |
| Primer 8m3 | − | 2.1 | 2.1 | 1.9 | 2.0 |
| (no primer) | + | 2.3 | 2.2 | 2.1 | 2.2 |

These data again demonstrate that if the 3' base of a primer is not able to hybridize to the corresponding base on an RNA template, it will not generate a strong light signal in the pyrophosphorylation reaction as described above. These data also demonstrate that this method can be used to determine if the terminal base of a primer does complement the expected base in the RNA and thus can be used to confirm that the RNA base at the site of pyrophosphorylation initiation is as expected.

Example 42

Mutation Detection Using Primers to Globin mRNA #2: Detection of Mismatched Bases Pentultimate to the 3' End of the Primer Sequence Since Example 41 shows that a mismatch at the end of a primer can be detected by the absence of a light signal under conditions allowing pyrophosphorylation, a series of primers corresponding to Primer 6 and Primer 8 were made that had altered based at the pentultimate base from the 3' end of the primer sequence.

The primers 6m4 through 6m6 were dissolved in 1×TE buffer to a concentration of 500 ng/μl.

Hybridization solutions containing primer 6 and primer 6m4 through primer 6m6 (SEQ ID NO:10, 11 and 12) or primer 8 and primers 8m4 through primer 8m8 (SEQ ID NO:22, 23, 24, 25 and 26) were assembled by adding 5 μl of 20 ng/μl of globin mRNA or Tris-Cl buffer. The solutions were heated at 50° C. for 15 min and then allowed to cool to room temperature for 15 min.

Reaction master mix was assembled as in Example 38 above and 18 μl of the mix was placed in 18 tubes. After cooling for 15 min, 2 μl of the various hybridization solutions containing primer 6 through primer 6m6 were added to the tubes and the tubes were placed in a 37° C. heating block.

After a 15 min incubation at 37° C. of the hybridization mixes in the Reaction Master Mix, 20 μl of the reaction was added to 100 μl L/L reagent and the light output of the reaction measured immediately. The following data were recorded:

TABLE 72

| Primer | RNA (+/−) | Light Units | | | Average |
|---|---|---|---|---|---|
| Primer 6 | + | 138.6 | 111.6 | 116.0 | 122.1 |
| Primer 6 | − | 14.67 | 12.28 | 9.57 | 12.17 |
| Primer 6m4 | + | 7.21 | 6.82 | 7.46 | 7.16 |
| Primer 6m4 | − | 6.24 | 5.90 | 6.28 | 6.14 |
| Primer 6m5 | + | 19.97 | 19.30 | 16.80 | 18.69 |
| Primer 6m5 | − | 6.27 | 6.23 | 6.23 | 6.23 |
| Primer 6m6 | + | 8.22 | 6.92 | 7.02 | 7.39 |
| Primer 6m6 | − | 6.40 | 6.32 | 5.98 | 6.23 |
| (no primer) | + | 4.91 | 7.59 | 5.14 | 6.24 |

Reaction master mix was assembled as in Example 38 and 18 μl of the mix was placed in 18 tubes. After cooling 15 min, 2 μl of the various hybridization solutions containing primer 8 through primer 8m6 were added to the tubes and the tubes were placed in a 37° C. heating block.

After a 15 min incubation at 37° C. of the hybridization mixes in the Reaction Master Mix, 20 μl of the reaction was added to 100 µl L/L reagent and the light output of the reaction measured immediately. The following data were recorded:

TABLE 73

| Primer | RNA (+/-) | Light Units | | | Average |
|---|---|---|---|---|---|
| Primer 8 | + | 71.24 | 55.85 | 76.33 | 67.81 |
| Primer 8 | - | 12.65 | 10.15 | 6.96 | 9.91 |
| Primer 8m4 | + | 5.10 | 5.48 | 5.31 | 5.30 |
| Primer 8m4 | - | 4.76 | 5.08 | 5.04 | 4.96 |
| Primer 8m5 | + | 5.60 | 5.06 | 5.61 | 5.42 |
| Primer 8m5 | - | 2.63 | 4.42 | 4.88 | 3.98 |
| Primer 8m6 | + | 5.68 | 6.13 | 5.79 | 5.87 |
| Primer 8m6 | - | 4.72 | 4.60 | 4.84 | 4.72 |
| (no primer) | + | 5.33 | 4.64 | 4.18 | 4.72 |

These data demonstrate that if the penultimate base to the 3' end of a primer is not able to hybridize to the corresponding base on an RNA template, very little pyrophosphorolysis occurs and a strong signal is not generated. These data also demonstrate that this method can be used to determine if the penultimate base of a primer does complement the expected base in the RNA and thus can be used to confirm that the RNA base at the site of the penultimate base of the primer is as expected.

Example 43
Modification of the Length of Primers Used for Pyrophosphorylation #1, Alteration of Length by Extending the 3' and 5' End of Primers It is possible that changing the length of primers used as substrates in the pyrophosphorylation reaction might affect either the specificity of the reaction or the strength of the signal produced. In this study, various primer combinations will be used to determine the effect of altering the length or the ends of primers.

Primers 9 through 17 were dissolved in 1×TE Buffer to a concentration of 500 ng/µl. These solutions were then each diluted to a primer concentration of 20 ng/µpl using 10 mM Tris-Cl buffer pH 7.3. Globin mRNA (Gibco BRL Product number #18103-010, lot KB6705) was dissolved in 10 mM Tris-Cl, pH 7.3 buffer at a concentration of 20 ng/µl. Separate 10 µl hybridization reactions were assembled by mixing 5 µl of Primers 6 and Primers 9–17 (SEQ ID NO:28, 29, 30, 31, 32, 33, 34, 35 and 36) with 5 µl of globin mRNA solution. Control mock hybridization solutions were also made by mixing 5 µl Primer 6 and 9–17 with 5 µl 10 mM Tris-Cl pH 7.3 and an RNA alone control made by mixing 5 µl globin mRNA solution with 10 mM Tris-Cl pH 7.3. All of these reactions were heated at 50° C. for 15 min and then were allowed to cool on to room temperature for 15 min.

A master reaction mix was made which contained per reaction assembled:

| | |
|---|---|
| Nanopure water | 10.5 µl |
| 5X MMLV-RT Buffer | 4.0 µl |
| 40 mM Sodium Pyrophosphate | 0.5 µl |
| NDPK (0.1 u/µl) | 1.0 µl |
| ADP (2 µM) | 1.0 µl |
| MMLV-RT enzyme | 1.0 µl |

Triplicate reactions were formed for each hybridization solution, primer control solution and globin RNA solution. Each of these was formed by adding two microliters of each solution to 18 µl of master reaction mix, mixing and incubating the resulting solution at 37° C. for 20 min. After this incubation, each solution was added to 100 µl L/L reagent and the light output of the solution read immediately using a Turner 20/20 Luminometer.

The following data were obtained:

TABLE 74

| Hybridization Solution | Light Values | | | Average | Net Average* |
|---|---|---|---|---|---|
| Primer 9 + Globin mRNA | 123.8 | 141.4 | 124.1 | 129.8 | 124 |
| Primer 9 w/o Globin mRNA | 5.7 | 5.5 | 6.1 | 5.8 | |
| Primer 10 + Globin mRNA | 182.4 | 164.4 | 170.5 | 172.4 | 166.6 |
| Primer 10 w/o Globin mRNA | 5.7 | 5.9 | 5.9 | 5.8 | |
| Primer 6 + Globin mRNA | 298.8 | 306.8 | (nd) | 302.8 | 289.6 |
| Primer 6 w/o Globin mRNA | 12.8 | 13.7 | 13.0 | 13.2 | |
| Primer 11 + Globin mRNA | 278.2 | 247.3 | 271.9 | 265.8 | 260.0 |
| Primer 11 w/o Globin mRNA | 5.7 | 5.8 | 5.8 | 5.8 | |
| Primer 12 + Globin mRNA | 280.5 | 322.0 | 345.9 | 316.1 | 309.6 |
| Primer 12 w/o Globin mRNA | 6.5 | 6.5 | 66 | 6.5 | |
| Primer 13 + Globin mRNA | 94.0 | 83.2 | 89.7 | 89.0 | 83.2 |
| Primer 13 w/o Globin mRNA | 5.8 | 5.7 | 5.8 | 5.8 | |
| Primer 14 + Globin mRNA | 276.8 | 328.8 | 348.0 | 317.9 | 312.1 |
| Primer 14 w/o Globin mRNA | 5.7 | 5.7 | 5.8 | 5.7 | |
| Primer 15 + Globin mRNA | 180.0 | 159.3 | 176.7 | 172.0 | 166.1 |
| Primer 15 w/o Globin mRNA | 5.8 | 5.9 | 6.0 | 5.9 | |
| Primer 16 + Globin mRNA | 67.2 | 60.5 | 67.4 | 65.0 | 58.8 |
| Primer 16 w/o Globin mRNA | 6.2 | 6.2 | 6.3 | 6.2 | |
| Primer 17 + Globin mRNA | 232.7 | 197.0 | 207.0 | 212.2 | 206.4 |
| Primer 17 w/o Globin mRNA | 5.7 | 5.8 | 6.0 | 5.8 | |
| No Primer + Globin mRNA | 6.5 | 6.3 | 6.4 | 6.4 | |

*Net average is average with primer and RNA minus average with primer but w/o RNA.

These data the following comparisons:
Primers with identical 3' ends but various lengths:

TABLE 75

| Primer Length (Bases) | Light Signal |
|---|---|
| 10 | 124.0 |
| 20 | 166.6 |
| 30 | 289.6 |
| 40 | 260.0 |
| 50 | 309.6 |

Primers with Identical 5' ends but various lengths:

TABLE 76

| Primer Length (Bases) | Light Signal |
|---|---|
| 10 | 83.2 |
| 20 | 312.1 |
| 30 | 166.1 |
| 40 | 58.8 |
| 50 | 294.4 |

These (Tables 75 and 76) suggested that increasing primer length at the 5' end of the primer might be an effective way to increase the light output from pyrophosphorylation reactions performed as described above. However, these results might have been due to the position where the primer hybridized on the RNA. In order to further test if primer length could affect light output in a regular way, another study was performed. In this study, the 3' sequence of the primer was kept constant and the 5' end extended to match larger and larger regions of the RNA. The region selected for hybridization was included in some of the region that was the target of the primers above where the 5' sequence of the primer was held constant.

Primers 18–22 (SEQ ID NO:37, 38, 39, 40 and 41) were dissolved and diluted as above. Hybridization solutions of these primers with globin mRNA, primer alone and RNA alone were prepared, heated and cooled as above.

These solutions were added to master mix made as above and incubated and tested for the presence of ATP as above. The following data were obtained:

TABLE 77

| Hybridization Solution | Light Values | | | Average | Net Average |
|---|---|---|---|---|---|
| Primer 18 + Globin mRNA | 19.4 | 19.8 | 18.3 | 19.2 | 13.2 |
| Primer 18 w/o Globin mRNA | 6.0 | 5.5 | 6.4 | 6.0 | |
| Primer 19 + Globin mRNA | 172.0 | 137.7 | 140.5 | 150.1 | 144.4 |
| Primer 19 w/o Globin mRNA | 5.8 | 5.8 | 5.5 | 5.7 | |
| Primer 20 + Globin mRNA | 77.1 | 65.9 | 66.7 | 69.9 | 64.3 |
| Primer 20 w/o Globin mRNA | 5.5 | 5.6 | 5.6 | 5.6 | |
| Primer 21 + Globin | 139.6 | 151.5 | 142.8 | 144.6 | 139.0 |
| Primer 21 w/o Globin mRNA | 5.5 | 5.7 | 5.6 | 5.6 | |
| Primer 22 + Globin mRNA | 62.3 | 99.6 | 52.1 | 71.3 | 60.8 |
| Primer 22 w/o Globin mRNA | 10.5 | 10.4 | 10.6 | 10.5 | |
| No Primer + Globin mRNA | 8.1 | 8.2 | 8.3 | 8.2 | |

These primers did not give increasing light values as primer length was increased as seen for the other set of primers varied at their 5' end above (Table 75). This suggests that, while primers of a wide range of sizes appear to give some signal in this detection of RNA, variability in the strength of the signal between primers is not totally unexpected.

Example 44
Effect of Mismatch Location on the Signal Derived From Pyrophosphorylation of a Primer to a Known RNA Since primers that are mismatched at the 3' base or the penultimate 3' base do not give a light signal following incubation in the pyrophosphorylation reaction conditions given in Examples 41 and 42 above, the following experiment was performed to determine if a mismatched base further within the primer sequence could affect the light signal generated from pyrophosphorylation reactions.

Primers 6m7 through 6m10 (SEQ ID NO:13, 14, 15 and 16) and primers 8m7 through 8m9 (SEQ ID NO:25, 26 and 27) were dissolved and diluted as in the Example 42 above. Globin mRNA (Gibco BRL Product number #18103-010, lot KB6705) was dissolved in 10 mM Tris-Cl, pH 7.3 buffer at a concentration of 20 ng/μl. Ten microliter hybridization reactions were assembled by mixing 5 μl Primers 6, 6m1, 6m6, and 6m7 through 6M10, 8, 8m3, 8m5 and 8m7–9 with 5 μl globin mRNA solution. Control mock hybridization solutions were also made by mixing 5 μl of the primers listed above with 5 μl 10 mM Tris-Cl pH 7.3 and an RNA alone control made by mixing 5 μl globin mRNA solution with 10 mM Tris-Cl pH 7.3. All of these were heated at 50° C. for 15 min and then were allowed to cool on to room temperature for 15 min.

A master reaction mix was made which contained per reaction assembled:

| Nanopure water | 10.5 μl |
|---|---|
| 5X MMLV-RT Buffer | 4.0 μl |
| 40 mM Sodium Pyrophosphate | 0.5 μl |
| NDPK (0.1 u/μl) | 1.0 μl |
| ADP (2 μM) | 1.0 μl |
| MMLV-RT enzyme | 1.0 μl |

Triplicate reactions were formed for each hybridization solution, primer control solution and globin RNA solution. Each of these was formed by adding two microliters of each solution to 18 μl of master reaction mix, mixing and incubating the resulting solution at 37° C. for 20 min. After this incubation, each solution was added to 100μl L/L reagent and the light output of the solution read immediately using a Turner 20/20 Luminometer.

The following data were obtained:

TABLE 78

| Hybridization Solution | Mismatch Location From Primer 3' End | Light Values | Average | Net Average |
|---|---|---|---|---|
| Primer 6 + Globin mRNA | none | 284.9, 283.2300.0 | 289.3 | 268.7 |
| Primer 6 – Globin mRNA | none | 20.5, 20.720.8 | 20.7 | |
| Primer 6m1 + Globin mRNA | 1 (terminal) | 6.5, 6.3 6.3 | 6.4 | 1.3 |
| Primer 6m1 – Globin mRNA | 1 (terminal) | 5.2, 5.1 5.1 | 5.1 | |
| Primer 6m6 + Globin mRNA | 2 | 10.7, 11.5 12.7 | 11.6 | 6.6 |
| Primer 6m6 – Globin mRNA | 2 | 5.2, 4.9 4.8 | 5.0 | |
| Primer 6m7 + Globin mRNA | 3 | 33.3, 30.5 31.3 | 31.7 | 27.0 |
| Primer 6m7 – Globin mRNA | 3 | 4.4, 4.9 4.7 | 4.7 | |
| Primer 6m8 + Globin mRNA | 4 | 38.7, 37.7 37.1 | 37.8 | 33.0 |
| Primer 6m8 – Globin mRNA | 4 | 4.9, 4.8 4.8 | 4.8 | |
| Primer 6m9 + Globin mRNA | 5 | 68.3, 66.1 66.8 | 67.i | 62.1 |
| Primer 6m9 – Globin mRNA | 5 | 5.0, 4.95.1 | 5.0 | |
| Primer 6m10 + Globin mRNA | 6 | 37.9, 35.6 36.0 | 36.5 | 31.6 |
| Primer 6m10 – Globin mRNA | 6 | 4.9, 4.9 5.0 | 4.9 | |
| Primer 8 + Globin mRNA | none | 144.1, 159.0165.9 | 156.3 | 122.5 |
| Primer 8 – Globin mRNA | none | 33.7, 33.6 34.1 | 33.8 | |
| Primer 8m3 + Globin mRNA | 1 (terminal) | 6.2, 6.3 6.2 | 6.2 | 1.0 |
| Primer 8m3 – Globin mRNA | 1 (terminal) | 5.3, 5.1 5.1 | 5.2 | |
| Primer 8m5 + Globin mRNA | 2 | 6.4, 6.2 6.2 | 6.3 | 1.1 |
| Primer 8m5 – Globin mRNA | 2 | 4.9, 4.8 6.0 | 5.2 | |
| Primer 8m7 + Globin mRNA | 3 | 8.3, 8.2 7.6 | 8.0 | 3.1 |
| Primer 8m7 – Globin mRNA | 3 | 4.9, 4.9 5.0 | 4.9 | |
| Primer 8m8 + Globin mRNA | 4 | 27.12, 26.4 26.5 | 26.7 | 21.9 |
| Primer 8m8 – Globin mRNA | 4 | 4.9, 4.7 4.7 | 4.8 | |
| Primer 8m9 + Globin mRNA | 5 | 42.5, 43.7 45.3 | 43.8 | -7.3 |
| Primer 8m9 – Globin mRNA | 5 | 53.9, 50.1 49.4 | 51.1 | |
| Globin mRNA Alone | na | 5.7, 5.8 5.5 | 5.7 | |
| No Primer, No RNA | na | 5.2, 5.2 5.3 | 5.2 | |

These data indicate that even mismatches as far as 6 base pairs from the 3' end of the primer will significantly reduce the light output from primer pyrophosphorylation reactions where an RNA template and MMLV-RT are used in the reaction. Thus, such a reduction can be used to indicate that a mutation has taken place in a region of an RNA at least 6 base pairs in length.

Example 45
Detection of DNA Using an Internal Primer

This experiment is designed to demonstrate that specific DNA sequences can be detected by denaturing the DNA in the presence of a short oligonucleotide (a primer) that encodes a nucleotide sequence that can hybridize to the DNA, allowing the solution containing the denatured DNA to cool, and performing a pyrophosphorylation reaction on the solution followed by transfer of the terminal phosphate of the nucleoside triphosphates produced to ADP to form ATP. The ATP produced can be measured using a luciferase/luciferin reaction.

Two microliters of a 1 mg/ml DNA solution of a plasmid containing the kanamycin resistance gene was incubated with 5 µl buffer K (Promega Corp), 4 µl of Endonuclease Sph I (10 u/µl, Promega Corporation), and 39 µl nuclease-free water for 1 hr at 37° C. The solution was then incubated at 70° C. for 10 min to inactivate the endonuclease. The final solution was labeled as Sph I digested pKAN (40 ng/µl).

The following solutions were assembled:

Solutions 1 and 2:
  2 µl Sph I digested pKAN
  18 µl nuclease-free water
Solutions 3 and 4:
  1 µl 1 mg/ml Primer 1
  19 µl nuclease-free water
Solutions 5 and 6:
  2 µl Sph I digested pKAN
  1 µl 1mg/ml Primer 1
  17 µl nuclease-free water.

These solutions were heated at 95° C. 3 min and cooled to room temperature in approximately 10 min by placing them on a laboratory bench.

A 2X Master Mix was assembled as follows:
  40 µl 10×DNA Polymerase buffer (Promega, M195A)
  10 µl 40 mM Sodium Pyrophosphate
  10 µl (10 u/µl) Klenow exo minus DNA Polymerase (Promega, M218B)
  2 µl NDPK at a concentration of 1 u/µl
  4 µl 10 µM ADP
  134 µl nuclease-free water The Master Mix components were mixed and 20 µl 2X MasterMix was added to each of the solutions heated to 95° C. after they had cooled to room temperature. The reactions were then heated to 37° C. for 20 min and then 4 µl of the reaction was added to 100 µl L/L reagent and the light produced by the reaction was immediately measured using a Turner 20/20 luminometer. The following data were obtained:

TABLE 79

| Reaction | Light Output |
| --- | --- |
| #1 | 5.1 |
| #2 | 4.6 |
| #3 | 2.2 |
| #4 | 2.0 |
| #5 | 423.4 |
| #6 | 430.5 |

These results show that a strong light signal can be produced from reactions containing a target DNA sequence, a primer that hybridizes to this DNA sequence internally, Klenow DNA polymerase and the other components of the reaction listed in this example. Note that the signal produced is far greater when all the components are present than when either the target DNA or primer are not present in the reaction.

Example 46
Identification of a Specific DNA Sequence in Plasmid DNA Through the Use of Primers That Hybridize to the DNA The previous example indicates that specific DNA sequences can be detected using primers that hybridize to the sequence through the use of a pyrophosphorylation reaction. Previous examples demonstrate that such a reaction can also be used to detect mutations in RNA sequences if primers are designed to identify the base pair present at the 3' end of the primer. This example describes how an analogous reaction can be performed using DNA as a template for the pyrophosphorylation reaction.

The following solutions were assembled:

TABLE 80

| Solution | pKAN DNA | Primer/µl | Water* |
| --- | --- | --- | --- |
| 1 and 2 | 1 µl | — | 19 µl |
| 3 and 4 | 1 µl | 1 µl Primer 1 | 18 µl |
| 5 and 6 | 1 µl | 1 µl Primer 2 | 18 µl |
| 7 and 8 | 1 µl | 1 µl Primer 3 | 18 µl |
| 9 and 10 | 1 µl | 1 µl Primer 4 | 18 µl |

*Nuclease free water.

These solutions were heated at 95° C. 3 min and cooled to room temperature for 10 min. A 2X MasterMix was assembled and mixed as described in Example 45 and 20 µl of this Master Mix was added to each of the solutions above. These reactions were incubated at 37° C. for 20 min and then 4 µl of each was added to 100 µl L/L and the light production of the resulting reaction was measured using a Turner 20/20 luminometer.

The following data were obtained:

TABLE 81

| Reaction | Light Units |
| --- | --- |
| #1 | 2.2 |
| #2 | 2.3 |
| #3 | 227.5 |
| #4 | 225.8 |
| #5 | 28.1 |
| #6 | 27.1 |
| #7 | 17.9 |
| #8 | 18.3 |
| #9 | 21.6 |
| #10 | 21.6 |

These data demonstrate that primers that exactly match a DNA sequence present on a plasmid give much higher light signals than do primers that contain a mismatch at the 3' end of the primer. Since the primer can be designed to match the base expected at the site, a drastic drop in this signal can indicate that the expected base is not present at the site. This system then can be used to detect mutations in DNA that alter a base from an expected sequence to another base.

Example 47
Initial Detection Limit for Plasmid DNA by Use of Primer Pyrophosphorylation In the previous two examples, plasmid DNA was specifically detected using primers that hybridized to a sequence in the DNA. In this example, we perform a titration of DNA in the pyrophosphorylation reaction to determine the level of DNA needed to obtain a signal from this reaction.

The Sph I cut pKAN DNA (40,000 pg/µl) was serially diluted using nuclease-free water to obtain concentrations of 10,000, 2,500, 625, 156 and 39 pg/µl. Duplicate solutions containing 1 µl each of these DNA solutions, 1 µl Primer 1 and 18 μl nuclease-free water were assembled as was a pair of solutions containing 1 μl primer 1 and 19 μl of nuclease-free water. All of these were heated at 95° C. for 3 min and then cooled for 10 min to room temperature. A 2×master mix was made as described in Example 45 and 20 μl of the mix was then added to all tubes and the tubes incubated at 37° C. for 20 min. A 4 μl sample of the solution was then added to 100 μl L/L reagent and the light measured using a Turner 20/20 luminometer. The following results were obtained:

TABLE 82

| Reaction | DNA Assayed* | Light Units |
|---|---|---|
| #1 | 4000 pg | 168.4 |
| #2 | 4000 pg | 169.4 |
| #3 | 1000 pg | 57.7 |
| #4 | 1000 pg | 77.9 |
| #5 | 250 pg | 19.3 |
| #6 | 250 pg | 21.1 |
| #7 | 62.5 pg | 6.3 |
| #8 | 62.5 pg | 6.4 |
| #9 | 15.6 pg | 2.4 |
| #10 | 15.6 pg | 2.3 |
| #11 | 3.9 pg | 1.4 |
| #12 | 3.9 pg | 1.4 |
| #13 | 0 pg | 1.1 |
| #14 | 0 pg | 1.4 |

These data demonstrate that the detection limit for DNA by this reaction under these conditions is at least 62.5 pg of DNA and is probably 15.6 pg of DNA or less.

Example 48
Detection of β-galactosidase Sequences in Plasmids

In this example, two primers are used that complement each other. One of these matches the sequence of the β-galactosidase gene exactly (sense orientation) and the other primer exactly matches the complementary strand (antisense orientation) of this gene. This example demonstrates that, while both primers can be used to detect the presence of the β-galactosidase gene in plasmid DNA, the level of background signal given by reactions containing only primer DNA can be very different.

Primer 23 and 24 (SEQ ID NO:42 and 43) were dissolved as described above to a concentration of 500 ng/μl and then diluted in nuclease-free water to 100 and 20 ng/μl. Plasmid pGEM7zf+ (Promega Corp.) was digested with Sac I (Promega Corporation) and diluted to give a solution containing 20 ng of plasmid DNA/μl of solution.

The following solutions were assembled:

| Solution | Plasmid DNA | Primer, Concentration | H₂O |
|---|---|---|---|
| #1 | 1 μl | (none, 1 μl of 1 X TE added) | 18 μl |
| #2 | 0 | 1 μl Primer 23, 500 ng/μl | 19 μl |
| #3 | 0 | 1 μl Primer 23, 100 ng/μl | 19 μl |
| #4 | 0 | 1 μl Primer 23, 20 ng/μl | 19 μl |
| #5 | 1 μl | 1 μl Primer 23, 500 ng/μl | 18 μl |
| #6 | 1 μl | 1 μl Primer 23, 100 ng/μl | 18 μl |
| #7 | 1 μl | 1 μl Primer 23, 20 ng/μl | 18 μl |
| #8 | 0 | 1 μl Primer 24, 500 ng/μl | 19 μl |
| #9 | 0 | 1 μl Primer 24, 100 ng/μl | 19 μl |
| #10 | 0 | 1 μl Primer 24, 20 ng/μl | 19 μl |
| #11 | 1 μl | 1 μl Primer 24, 500 ng/μl | 18 μl |
| #12 | 1 μl | 1 μl Primer 24, 100 ng/μl | 18 μl |
| #13 | 1 μl | 1 μl Primer 24, 20 ng/μl | 18 μl |

These solutions were heated at 95° C. 3 min and cooled to room temperature. Then, 20 μl 2X MasterMix—made as described in Example 45 was added and the solutions incubated for another 20 min at 37° C. Four microliters of the solution were then added to 100 μl L/L and the light output of the reaction measured using a Turner 20/20 luminometer.

The following data were obtained:

TABLE 83

| Reaction | Light Output | Net Light Output* |
|---|---|---|
| #1 | 2.8 | |
| #2 | 4.0 | |
| #3 | 1.9 | |
| #4 | 1.3 | |
| #5 | 52.4 | 45.6 |
| #6 | 13.6 | 8.9 |
| #7 | 4.1 | 0 |
| #8 | 34.3 | |
| #9 | 6.6 | |
| #10 | 1.7 | |
| #11 | 59.8 | 22.7 |
| #12 | 19.3 | 9.9 |
| #13 | 6.0 | 1.5 |

*Net light output is calculated by subtracting the primer alone and DNA alone values from that obtained with both components present.

These data indicate that both primers can be used to generate a signal indicating the presence of the region encoding the β-galactosidase gene matching the primers is present in the plasmid. They also demonstrate that the level of signal produced with a primer in the absence of target DNA can vary and that the signal from a primer and the complement of that primer will not necessarily be equal.

Example 49
Detection of Specific DNA Sequences on Lambda DNA

In this example, detection of the β-galactosidase gene in the DNA of a recombinant Lambda phage will be demonstrated.

Duplicate solutions were made that contained: Solution 1 and 2, 1 μl 300 ng/μl of Lambda gt11 DNA and 19 μl of nuclease free water; Solution 3 and 4, 1 μl 500 ng/μl Primer 23 and 19 μl nuclease-free water; Solution 5 and 6, 1 μl 300 ng/μl Lambda gt11 DNA, 1 μl 500 ng/μl Primer 23, and 18 μl nuclease-free water. All these were heated at 95° C. 3 min and then cooled to room temperature for 10 min. At this point, 20 μl 2×Master Mix made as described in Example 45 was added and the solution incubated for another 20 min at 37° C. A 4 μl sample of the reaction was then taken and added to 100 μl L/L and the light production of the solution measured. The following data were obtained.

TABLE 84

| Reaction | DNA Components | Light Units |
|---|---|---|
| #1 | Lambda DNA | 16.5 |
| #2 | Lambda DNA | 7.4 |
| #3 | Primer 23 | 2.9 |
| #4 | Primer 23 | 2.9 |
| #5 | Lambda DNA and Primer 23 | 88.1 |
| #6 | Lambda DNA and Primer 23 | 70.4 |

These data indicate that the primer pyrophosphorylation system can be used to detect specific sequences on lambda gt11 DNA.

Example 50
Detection of Low Levels of Endonuclease by Substrate Destruction

In this example, a sample of double-stranded DNA is exposed to decreasing levels of a nonspecific endonuclease.

After digestion, the solutions are added to the pyrophosphorylation reaction mix to determine the amount of residual double-stranded DNA. By this approach, we will demonstrate that the measurement of extremely low levels of endonuclease is possible.

An enzyme dilution solution was made by adding 20 µl of 10 mg/ml BSA (Promega R396, lot 8560803) to 180 µl Buffer A (made by dilution of 18 µl 10×Buffer A (Promega R001, lot 7651104 with 162 µl nanopure water (Promega AA399, LSS652). This solution was used to dilute RQ1 DNAse (Promega M610, lot 7520108) to concentrations 0.001×, 0.00033×, 0.0001×, 0.000033×, and 0.00001× the original concentration of the enzyme (1 u/ul).

A diluted DNA solution was made by diluting a 500 bp DNA fragment (the 500 bp fragment used in a DNA ladder (Promega G210) to a concentration of 10 ng/µl.

Six DNA substrate mixes were made by adding: 8 µl nanopure water; 4 µl 10 mM $CaCl_2$; 2 µl 10×Buffer A; 2 µl 10 mg/ml BSA; 2 µl diluted DNA to six 0.5 ml microfuge tubes and mixing. One microliter of the different RQ1 DNAse solutions above was added to one of the tubes and one microliter of nanopure water was added to the final tube as a control.

The tubes were again mixed and incubated overnight at 37° C. and placed on ice.

A master reaction mix was made by adding: 250 µl nanopure water; 40 µl 10×Buffer A; 20 µl NDPK (0.1 u/µl); 20 µl 2 µM ADP; 10 µl 20 mM sodium pyrophosphate (made by a 1:1 dilution of Promega C113, lot 6675705 with nanopure water; and, 20 µl E. coli polymerase I (Promega M205, lot 8104702), in a 1.5 ml microfuge tube and mixing the tube by vortex action. Eighteen 0.5 ml tubes were labeled and 18 µl of the master reaction mix was added to each tube. Two microliters of each DNA digest (incubated overnight) were added to three tubes and the resulting solutions were mixed by vortex and incubated at 37° C. for 18 min. After incubation, the contents of each tube was added to 100 µl L/L and the light production of the resulting reaction measured immediately using a Turner Luminometer. The following data were obtained:

TABLE 85

| | Light Units | | | |
|---|---|---|---|---|
| RQ1 DNAse Dilution | Rx1 | Rx2 | Rx3 | Average Light Units |
| 0.001X | 131.8 | 126.0 | 120.0 | 125.9 |
| 0.00033X | 251.4 | 271.4 | 271.4 | 264.7 |
| 0.0001X | 459.5 | 457.8 | 446.5 | 454.6 |
| 0.000033X | 1351 | 1377 | 1397 | 1375 |
| 0.00001X | 1620 | 1711 | 1708 | 1680 |
| no enzyme | 1895 | 1840 | 1933 | 1889 |

These data show that even as little as a 1 to 100,000 fold dilution of the RQ1 DNase can be easily measured by this assay.

Example 51
Detection of Specific Endonuclease Activity

In this example, a different endonuclease, Rsa I, is incubated with closed circular plasmid DNA. Closed circular DNA is not normally a substrate for pyrophosphorylation. However, if the endonuclease creates double-strand DNA breaks in the plasmid, the resulting linear DNA will be a substrate for the reaction using T4 DNA polymerase. Samples of plasmid DNA incubated with Rsa I are taken and subjected to the pyrophosphorylation reaction. The resulting solutions are then added to solutions of luciferase and luciferin and the ATP formed detected by light production. The resulting data indicate that the activity of endonucleases can be detected at very low levels using such methods.

A 1×Buffer C stock was made by diluting 20 µl of 10×Buffer C (Promega R003, lot 7544205) with 180 µl nanopure water (Promega AA399, lot LSS652). This was used to produce an Rsa I dilution buffer by adding 20 µl 10 mg/ml BSA (Promega R396, lot 8560803) to 180 µl 1×Buffer C. The Rsa I dilution buffer was used to dilute a solution of Rsa I (Promega R937 lot 7980003) to concentrations 0.1×, 0.01×, 0.001×, 0.00033×, 0.0001×, 0.000033× and 0.00001× the starting enzyme concentration (3 u/ul).

A solution of plasmid substrate was made by dilution of 1 µl of plasmid (pGEM 3ZF, Promega P227, 814180) to 100 µl with 10 mM Tris-Cl pH 7.3 (made by dilution of a 2M stock with nanopure water) to yield a 10 ng/µl plasmid DNA solution.

Six reaction tubes were assembled that contained: 13 µl nanopure water, 2 µl 10×Buffer C, 2 µl 10 mg/ml BSA, 2 µl 10 ng/µl DNA . One of these tubes received 1 µl RSA I dilution buffer. The remaining 5 tubes received 1 µl of the Rsa I dilutions from 0.001 to 0.00001×. The tubes were incubated overnight at 37° C.

The next day, 2 µl samples of the incubated tubes were added to pyrophosphorylation reaction mixes as described in the previous example and incubated 18 min at 37° C. After that time, the content of the tubes was added to 100 µl of L/L and the light produced by this reaction was measured using a Turner 20/20 Luminometer. The following data were obtained:

TABLE 86

| Rsa I Dilution | Light Units | | | Average |
|---|---|---|---|---|
| 0.001X | 555.9 | 584.3 | 535.5 | 558.6 |
| 0.00033X | 302.9 | 298.4 | 296.4 | 299.2 |
| 0.0001X | 299.5 | 310.9 | 325.4 | 311.9 |
| 0.000033X | 176.0 | 181.3 | 182.8 | 180.0 |
| 0.00001X | 96.7 | 104.4 | 106.4 | 102.5 |
| No Rsa 1 | 136.3 | 150.8 | 146.6 | 144.6 |

These data show that very low levels of Rsa I as a model endonuclease can be detected using this assay.

Example 52
Detection of Low Levels of Exonuclease

In this example, exonuclease will be detected by: using the exonuclease to produce 5' nucleotide monophosphates; transforming the dAMPs to the triphosphate form using PRPP Synthetase and PRPP; using the dATP to transform ADP to ATP using NDPK and measuring the ATP using luciferase.

An Exonuclease III dilution buffer was made by first diluting 20 µl 10×Exonuclease III reaction buffer (Promega E577, lot 4853218) with 180 µl nanopure water (Promega AA399, LSS9652) to form a 1×Exonuclease III solution then diluting 20 µl 10 mg/ml BSA (Promega R396, lot 8560803) with 180 µl 1×Exonuclease III buffer.

Exonuclease III (Promega M181, lot 5512708) was serially diluted with the Exonuclease III dilution buffer to obtain enzyme concentrations 0.1×, 0.01×, 0.001×, 0.00033×, 0.0001×, 0.000033× and 0.00001× the stock enzyme concentration (175 u/ul)/

Seven microliters of DNA (PhiX 174 HinF I DNA, Promega G175, lot 7733604) was diluted with 14 µl 10 mM Tris-Cl buffer made as in the previous example to obtain a solution containing 115 ng/µl DNA.

Six reaction tubes were assembled that contained: 13 µl nanopure water, 2 µl 10× Exonuclease III reaction buffer, 2

µl 10 mg/ml BSA, and 1 µl of the 115 ng/µl DNA stock. One tube received an additional microliter of nanopure water to act as a negative control reaction. The other five tubes received 1 µl of the diluted Exonuclease III samples at the concentrations ranging from 0.0001× to 0.00001× concentration. The reactions were incubated at 37° C. for 1 hr.

Eighteen 0.5 ml microfuge tubes received 5 µl of one of the digests made as described in the paragraph above, 2 µl ADP, 2 µl NDPK (both made as in the previous example), 2 µl PRPP (100 ug/ml made by diluting PRPP from the solid, Sigma Chemical Co.), 17 µl PRPP Synthase Reaction Buffer and 2 µl 0.01×PRPP Synthase in PRPP Synthase Reaction Buffer. The tubes were incubated at 37° C. for 30 min and then the reactions added to L/L and measured the light produced by the reaction.

The following data were obtained:

TABLE 87

| Exonuclease III Dilution | Light Values | | | Average Light Values |
|---|---|---|---|---|
| 0.001X | 106.3 | 96.2 | 110.0 | 104.2 |
| 0.00033X | 64.5 | 63.9 | 57.2 | 61.9 |
| 0.0001X | 58.6 | 48.4 | 51.3 | 52.8 |
| 0.000033X | 44.1 | 41.5 | 41.8 | 42.5 |
| 0.00001X | 38.9 | 38.3 | 42.6 | 39.9 |
| no enzyme | 49.9 | 40.7 | 40.4 | 43.6 |

These data show that Exonuclease III can be detected at dilutions at least as low as 0.0001× of 175 u/µl under these conditions.

Example 53
Detection of Exonuclease Activity by Substrate Digestion

In this example, an exonuclease is used to digest a linear double-stranded DNA. The remaining DNA is measured using pyrophosphorylation, phosphate transfer and luciferase-based light production. Since the exonuclease does not produce deoxynucleotide triphosphates from the DNA, any DNA digested by the exonuclease is expected to result in a loss of substrate for the latter reaction. Thus, by measuring the drop in substrate concentration left after incubation with the exonuclease, one can detect the exonuclease activity.

Exonuclease III was diluted as described in the previous example. A 1 µl sample of a 500 bp linear DNA segment (Promega G370, lot 79280), 1.46 mg/ml was diluted to 146 µl with nanopure water to form a solution of 10 ug/ml.

Six 0.5 ml tubes were assembled containing 12 µl nanopure water, 2 µl Exonuclease III 10× reaction buffer, 2 µl 10 mg/ml BSA, 1 µl diluted 500 bp DNA fragment. One of the tubes received an additional microliter nanopure water and was used as a no enzyme control. The other tubes received 1 µl concentrated Exonuclease III or diluted Exonuclease III at concentrations ranging from 0.1 to 0.0001× (stock 175 µ/µl). The tubes were incubated at 37° C. for 1 hr.

A master reaction mix was made that contained 275 µl nanopure water, 44 µl 10×Buffer A (Promega R001, lot 7651103), 22 µl NDPK (0.1 µ/µl), 22 µl ADP(2 µM), 11 µl sodium pyrophosphate (Promega C113, lot 6675705)and 22 µl T4 DNA polymerase (Promega M241, lot 6175711). Eighteen 0.5 ml microfuge tubes received 18 µl master reaction mix and 2 µl of each of the six tubes incubated at 37° C. with various concentrations of Exonuclease III were added to the tubes in triplicate. These new tubes were incubated for 1 hr at 37° C. and the contents of the tubes were added to 100 µl L/L and light output of the reaction measured using a Turner luminometer. The following results were obtained:

TABLE 88

| Exonuclease III Dilution | Light Units | | | Average Light Units |
|---|---|---|---|---|
| 1X (no dilution) | 21.6 | 23.5 | 19.3 | 21.5 |
| 0.1X | 32.0 | 44.9 | 32.8 | 36.6 |
| 0.01X | 72.0 | 69.9 | 75.3 | 72.4 |
| 0.001X | 554.3 | 539.2 | 542.6 | 545.4 |
| 0.0001X | 1028 | 1041 | 1025 | 1031 |
| no enzyme | 1170 | 1172 | 1114 | 1152 |

These data show that low levels of a double-stranded DNA exonuclease can be measured using this method.

Example 54
Primer Dependent Detection of a PCR Product by Pyrophosphorolysis

A 613 bp PCR product was synthesized by reverse transcription PCR (RT-PCR) from a 1.2 kb synthetic RNA corresponding to the kanamycin resistance gene in plasmid pKanDeltaCG. The RNA was synthesized using a commercial kit from Ambion (mMESSAGE mMACHINE SP6 Kit Cat#1340) Austin, Tex. PKanDeltaCG was first linearized with EcoR 1 to enable a run-off transcript to be made. The plasmid was digested for one hour at 37° C. in the following reaction:

25 µl 1 mg/ml pKan DeltaCG
10 µl 10X Multi-Core Buffer (Promega R999A)
5 µl 80 u/µl EcoR 1 (Promega R6011)
60 µl water 100 µl Ten microliters 5M NaCl was added to the EcoR 1 digested DNA and the reaction was extracted with 110 µl phenol:chloroform:isoamyl alcohol (49:49:2, Promega, Z529A). The supernatant was precipitated with two volumes ethanol, the pellet vacuum-dried and dissolved in 30 µl TE (10 mM Tris-HCl pH 8, 1 mM EDTA). The concentration of the digested plasmid was then adjusted to 0.5 mg/ml by the addition of TE.

The kanamycin transcript was generated in the following reaction:

16 µl RNase-free water (Ambion 9910G)
8 µl 10X Transcription Buffer (8153G)
40 µl 2X Ribonucleotide Mix (8055G)
8 µl EcoR 1 cut plasmid (4 µg)
8 µl 10X Enzyme Mix (2079G)

80 µl

The reaction was incubated at 37° C. for one hour. Most of the synthesized RNA contains a cap structure at the 5' end (GpppG) because a cap analogue was present in the ribonucleotide Mix. Following completion of the reaction, 4 µl DNase I (Ambion 2226G) was added and incubation continued for another 15 min at 37° C. One hundred twenty microliters water and 100 µl LiCl Precipitation Solution (Ambion 9480G) were then added. The reaction was chilled at −20° C. for 30 min and centrifuged in a microcentrifuge at 14,000 rpm for 15 min. The pellet was washed once in 70% ethanol and dissolved in 50 μl water. The concentration of the RNA was determined spectrophotometrically assuming that a 1 mg/ml solution would give an absorbance of 25 at 260 nm. The RNA was first prepared by attaching a small RNA oligonucleotide at the 5' end which served as a PCR anchor. In this way the entire 5' end of the RNA could be amplified by the PCR. Prior to the ligation of this RNA oligo to the kanamycin RNA, the kanamycin RNA was first treated with calf intestinal alkaline phosphatase (CIAP) and tobacco acid pyrophosphatase (TAP). The phosphatase step makes unavailable for the ligation pathway any RNA molecules which do not contain a 5' cap. Once the phosphatase is removed, the cap itself is removed with TAP. The synthetic kanamycin RNA was treated with CIAP in the following reaction:

---

0.6 μl 850 μg/ml total Mouse Liver RNA (Promega F160A)
1 μl 5 pg/μl capped Kanamycin RNA
5 μl 10X CIAP buffer
1 μl 40 u/μl rRNasin® (Promega N251E)
2 μl 1 ul/μl CIAP
40.4 μl water 50 μl

---

Following a one-hour 37° C. incubation, 250 μl water, 75 μl 10M ammonium acetate and 375 μl phenol:chloroform:isoamyl alcohol (49:49:2) were added. The reaction was vortexed and phases separated by a 5 min centrifugation in a microcentrifuge. The supernatant (350 μl) was removed and the extraction repeated. The supernatant was precipitated by the addition of 900 μl ethanol and centrifuged 5 min. Following a 70% ethanol wash, the pellet was dissolved in 43.5 μl water. To the CIAP-treated RNA was added:

5 μl 10×TAP buffer
1 μl 40 u/μl rRNasin®
1 μl 0.1 u/μl TAP (Epicentre T19500)

Following a one-hour incubation at 37° C., the reaction was extracted and precipitated as above and the pellet dissolved in 13 μl water. To it was then added:

41 μl 10×RNA Ligase buffer
1 μl 0.25 ug/μl RNA oligo 30 mer
1 μl 40 u/μl rRNasino®
1 μl 10 u/μl RNA Ligase (Promega M1051)
20 μl 40% polyethylene glycol (Sigma P-2139)

and the reaction incubated overnight at 16° C.
10×CIAP buffer: 100 mM Tris-HCl pH 8, 100 mM MgCl2, 0.5 M NaCl, 10 mM DTT
10×TAP buffer: 0.5M sodium acetate pH 6, 10 mM EDTA, 1% beta-mercaptoethanol, 0.1% Triton X-100
10×RNA Ligase buffer: 0.5M Tris-HCl pH 8, 100 mM MgCl2, 0.68% beta-mercaptoethanol, 10 mM ATP
Sequence of the RNA Oligo: 5' AGAGUCUUGACG-GAUCCAGGUACCAGUAAA3'

Following the ligation step, 250 μl water, 75 μl 10M ammonium acetate and 900 μl ethanol were added to the reaction. The mixture was vortexed and then centrifuged 20 min in a microcentrifuge at 14,000 rpm at 4° C. The pellet was washed in 70% ethanol and dissolved in 15 μl water. cDNA was first synthesized from the RNA prior to PCR. To the RNA was added 1 μl (50 pmoles) of a cDNA synthesis primer and the mixture heated at 70° C. for 5 min, then cooled to room temperature for 10 min. To the RNA/primer mix was added:

5 μl 5×First Strand buffer (Promega C121A)
1 μl 40 u/μl rRNasin®
2.5 μl 40 mM sodium pyrophosphate (Promega C113A)
1 μl 25 u/μl AMV reverse transcriptase (Promega M5108)

The reaction was incubated for 1 hr at 42° C. and then terminated by the addition of 0.5 μl 0.5M EDTA and 74 μl water. To 5 μl of the cDNA was added:

5 μl 10×Thermophilic buffer (Promega M190G)
5 μl 10×PCR dNTP
5 μl 25 mM MgCl2 (Promega A351H)
1 μl 320 ug/ml upstream primer
26.5 μl water The reaction was mixed and covered with 50 μl mineral oil. It was put into a thermalcycler (Perkin-Elmer Model 480) at 95° C. After 2 min, 1 μl 5 u/μl Taq DNA polymerase (Promega M166B) was added and the reaction cycled 95° C. 1 minute, 43° C. 1 minute, 72° C. 2 minutes for 5 cycles and then brought to 85° C. Then 1 μl 320 ug/ml downstream primer was added and the reaction cycled 95° C. 30 seconds, 55° C. 30 seconds, 72° C. 1 minute for 30 cycles followed by 5 minutes at 72° C. then 4° C.
10×PCR dNTP: 1 mM each of dATP, dGTP, dCTP and dTTP
Upstream primer: 5' TGATCGTAAGAGTCTTGACG-GATC3'
Downstream primer: 5' TCATTC(GTGATTGCGCCTGAGCGA3'

The PCR reaction generated a 613 bp product. To remove unincorporated primers and dNTP, a 15 μl aliquot of the PCR reaction was purified with Promega's Wizard PCR Preps (A7170) according to kit instructions. The concentration of the purified PCR product was determined by a pyrophosphorolysis assay. A Master Mix (MM) was assembled containing the following components:

---

20 μl 10X Buffer A (Promega R001A)
2 μl 40 mM sodium pyrophosphate
2 μl 10 μM ADP (Sigma A5285)
5 μl 1 u/μl NDPK (Sigma N0379)
151 μl water 180 μl

---

This mix was used in reactions containing control PhiX 174 HinF I DNA standard (Promega G175A) or aliquots of the PCR reaction, with and without added T4 DNAP (10 u). The PCR reaction was diluted 10× in TE buffer for use in the assay.

The results are below:

TABLE 89

| MM | 1 ng/μl | PhiX DNA | PCR | T4 DNAP | LU |
|---|---|---|---|---|---|
| 1– | 18 μl | — | — | + | 0.950 |
| 2– | 18 μl | 1 μl | — | + | 44.92 |
| 3– | 18 μl | 2 μl | — | + | 68.86 |
| 4– | 18 μl | 3 μl | — | + | 90.88 |
| 5– | 18 μl | — | 1 μl | — | 1.244 |
| 6– | 18 μl | — | 2 μl | — | 1.388 |
| 7– | 18 μl | — | 1 μl | + | 47.97 |
| 8– | 18 μl | — | 2 μl | + | 68.69 |

Light units (LU) generated resulted from adding 2 μl of reaction mixes to 100 μl L/L (Promega F202A).

As can be seen, the PhiX 174 HinF I DNA produced a light signal that was proportional to the amount of DNA added. The concentration of the tenfold diluted PCR reaction is almost exactly that of the DNA standard, so the undiluted PCR product DNA is at a concentration of 10 ng/µl. Note that only background light units are seen for the reactions that contained the PCR product but no T4 DNAP. This indicates essentially complete removal of the dNTP's during clean-up on the Wizard resin.

Next, we detected the PCR product by hybridizing and pyrophosphorolyzing a primer which bound to internal sequences. The sequence of the primer was 5'GCAACGC-TACCTTTGCCATGTTTC3'. For this purpose it was found most suitable to use the exonuclease minus Klenow DNAP (Promega M218B) in place of T4 DNAP. A 2X MasterMix (MM) was assembled as below:

| |
|---|
| 60 µl 10X DNAP buffer (Promega M195A) |
| 15 µl 40 mM sodium pyrophosphate |
| 15 µl 10 u/µl Klenow exonuclease minus DNAP |
| 3 µl 1 u/µl NDPK |
| 6 µl 10 uM ADP |
| 201 µl water |
| 300 µl |

PCR product (between 0 and 20 ng) was mixed (or not) with 1 µl of 1 µg/µl primer and water as below. The mixtures were heated at 95° C. 3 min and then allowed to cool to room temperature for 10 minutes. Then 20 µl of 2×MM was added and the reactions incubated 20 min at 37° C. before adding 4 µl to 100 µl L/L.

TABLE 90

| | PCR Prod. | Primer | Water | LU |
|---|---|---|---|---|
| 1 | 20 ng | – | 18 µl | 37.84 |
| 2 | 20 ng | + | 17 µl | 423.2 |
| 3 | 10 ng | – | 19 µl | 16.51 |
| 4 | 10 ng | + | 18 µl | 366.1 |
| 5 | 5 ng | – | 19 µl | 7.79 |
| 6 | 5 ng | + | 18 µl | 226.0 |
| 7 | 2.5 ng | – | 19 µl | 4.994 |
| 8 | 2.5 ng | + | 18 µl | 171.2 |
| 9 | 1.25 ng | – | 19 µl | 3.176 |
| 10 | 1.25 ng | + | 18 µl | 85.6 |
| 11 | 0 ng | + | 19 µl | 2.656 |

It can be seen that substantially higher LU results when the primer is present along with the DNA and that this signal is not due to the primer alone (reaction 11). It is surprising that only a very small amount of the PCR product has reannealed to give a signal during the course of the assay, even at the higher DNA amounts. The light units generated represent only one tenth of the DNA which was added to the reactions and from the data it is apparent that about 10 pg of the PCR product could easily be detected in a primer-dependent fashion.

Example 55
Mismatch (Mutation) Detection in a PCR Product

To demonstrate base interrogation, or mismatch detection, four different primers were used on the above PCR product. The wild-type (WT) primer was the same as that used in Example 37. In addition, three additional primers were used which differed in their terminal base at the 3' end. The WT primer (Primer 1) contained a C which matched to the G present on the PCR template. Three additional primers contained either G, A or T at the 3' terminal position (Primers 2, 3 and 4 respectively) and thus when hybridized to the template would create mismatches of GG, GA and GT, respectively. These mismatched bases should substantially block pyrophosphorolysis of the hybridized primer, allowing one to determine which base is present on the DNA template at that position. A 2X Master Mix (2X MM) was prepared as in Example 54 and 1 µl 10 ng/µl PCR product mixed with 1 µl 1 µg/µl primer and water or TE as below. The mixtures were heated 3 min at 95° C. then allowed to cool to room temperature for 10 min. Then 20 µl 2×MM was added, the reactions mixed and allowed to incubate for 20 min at 37° C. prior to adding 4 µl to 100 µl L/L and measuring the resulting light units produced.

TABLE 91

| | PCR/Primer | Water | TE | LU |
|---|---|---|---|---|
| 1 | +– | 18 µl | 1 µl | 21.82 |
| 2 | –1 | 19 µl | — | 2.628 |
| 3 | +1 | 18 µl | — | 322.1 |
| 4 | +– | 18 µl | 1 µl | 14.69 |
| 5 | –2 | 19 µl | — | 3.277 |
| 6 | +2 | 18 µl | — | 57.44 |
| 7 | +– | 18 µl | 1 µl | 23.14 |
| 8 | –3 | 19 µl | — | 4.861 |
| 9 | +3 | 18 µl | — | 40.90 |
| 10 | +– | 18 µl | 1 µl | 14.98 |
| 11 | –4 | 19 µl | — | 5.899 |
| 12 | +4 | 18 µl | — | 43.33 |

It can be seen that the greatest LU was obtained in the case of the matched primer (Primer 1). Subtracting the backgrounds of PCR product alone and primer alone, the following LU are obtained in the case of the matched and mismatched primers:

TABLE 92

| Primer And Template Resulting In | LU |
|---|---|
| GC match | 297.7 |
| GG mismatch | 39.47 |
| GA mismatch | 12.90 |
| GT mismatch | 22.45 |

It is clear that having a 3' terminal base which mismatches with the template dramatically reduces the rate of pyrophosphorolysis of the hybridized primer.

The primer alone backgrounds seen above are low (<10 LU). We have, however encountered primers which give very high backgrounds (as much as 500 LU per 100 ng primer). Such primers are generally complementary and capable of forming either self-dimers or hairpin structures leading to double-stranded regions at their 3' ends. Such primers are to be avoided and can often be detected using various secondary structure prediction programs. If one set of primers gives high background, it may be possible to use adjacent primers to the other strand with their 3' ends interrogating the same site.

Example 56
Mutation Detection on Pseudo-PCR Product Synthetic Templates

In order to show base interrogation on DNA templates where a base has actually been changed (mutation), synthetic oligonucleotides were made which correspond to a region of cytomegalovirus DNA in which a mutation can be present which has been shown to be responsible for resistance to the drug ganciclovir. The upper strand of the wild type template corresponds to sequence 1 below (SEQ ID NO:44), the bottom strand, sequence 2 below (SEQ ID NO:45). The base that is mutated is indicated in bold type. The upper strand of the mutant template (sequence 3 below, SEQ ID NO:46) is the same as sequence 1 but the bolded base has been changed from an A to a G. The bottom strand of the mutant template (sequence 4 below, SEQ ID NO:47) is the same as sequence 2 but the bolded base has been changed from a T to a C. Two oligos were used to interrogate the position of the mutated base, one corresponding to the wild type and the other to the mutant sequence. The sequence of the wild type interrogation oligo is sequence 5 (SEQ ID NO:48) below and the sequence of the mutant interrogation oligo is sequence 6 below (SEQ ID NO:49). These oligos were identified by the numbers 9211 and 9212, respectively. Sequence 5 differs from sequence 6 at the position of the bolded base and for these oligos the mismatched base is three nucleotides in from the 3' end of each oligo. It was expected that the wild type oligo would give the strongest signal on the wild type template and the mutant oligo the strongest signal on the mutant template. This was found to be the case as demonstrated in the experiment detailed below.

Wild type and mutant DNA templates to be interrogated were assembled by mixing together oligo sequence 1 with oligo sequence 2 and oligo sequence 3 with oligo sequence 4 to a final concentration of 0.3 micrograms/ml. Interrogation oligos 9211 and 9212 were both dissolved to a concentration of 1 mg/ml in TE buffer. Reactions were assembled as below and contained either template only, primer only or template plus primer:

| Wild Type | Template | 9211 | 9212 | Water |
|---|---|---|---|---|
| 1 and 2 | 1 µl | — | — | 19 µl |
| 3 and 4 | — | 1 µl | — | 19 µl |
| 5 and 6 | — | — | 1 µl | 19 µl |
| 7 and 8 | 1 µl | 1 µl | — | 18 µl |
| 9 and 10 | 1 µl | — | 1 µl | 18 µl |

Reactions were mixed and heated at 95° C. for 3 min and then allowed to cool to room temperature for 10 min on the bench. Then 20 µl of a 2X Master Mix was added, the reactions incubated 20 min at 37° C. then 4 µl was added to 100 µl of L/L and the resulting light units determined in a luminometer.

2X Master Mix:
60 µl 10× DNAP buffer
15 µl 40 mM sodium pyrophosphate
15 µl Klenow exo⁻ DNAP
3 µl 1u/µl NDPK
6 µl 10 µM ADP
201 µl water
300 µl The resulting relative light units were found to be:

| Reaction | Light Units |
|---|---|
| 1 | 1.687 |
| 2 | 1.732 |
| 3 | 4.313 |
| 4 | 3.948 |
| 5 | 10.54 |
| 6 | 10.04 |
| 7 | 220.8 |
| 8 | 206.8 |
| 9 | 49.67 |
| 10 | 37.33 |

It can be seen (1 and 2) that the DNA template itself yields very few LU as is the case for the interrogation primers alone (3 through 6). Wild type interrogation primer mixed with wild type template gives over 200 LU while the mutant primer mixed with the wild type template gives less than 50 LU. After subtracting the background given by the template and primers alone, it can be seen that the wild type oligo gives roughly five fold more signal on the wild type template than does the mutant oligo.

The above experiment was then repeated but substituting the mutant DNA template for the template. The resulting LU are shown below:

| Reaction | Light units |
|---|---|
| 1 | 1.760 |
| 2 | 1.779 |
| 3 | 4.157 |
| 4 | 4.316 |
| 5 | 11.0 |
| 6 | 10.56 |
| 7 | 34.31 |
| 8 | 29.53 |
| 9 | 241.9 |
| 10 | 264.5 |

Again it can be seen that background of template alone and primers alone are low (1–6) and that this time the greatest signal is seen with the mutant (9212) primer instead of the wild type primer. Thus, by comparing the ratio of signals obtained with the wild type and mutant primers, it is possible to distinguish the wild type from the mutant DNA.

TABLE 93

| Primer Designation | Sequence ID Number | Sequence |
|---|---|---|
| Primer 1 | SEQ ID NO:1 | 5'GCAACGCTACCTTTGCCATGTTTC3' |
| Primer 2 | SEQ ID NO:2 | 5'GCAACGCTACCTTTGCCATGTTTG3' |
| Primer 3 | SEQ ID NO:3 | 5'GCAACGCTACCTTTGCCATGTTTA3' |
| Primer 4 | SEQ ID NO:4 | 5'GCAACGCTACCTTTGCCATGTTTT3' |

TABLE 93-continued

| Primer Designation | Sequence ID Number | Sequence |
| --- | --- | --- |
| Primer 5 | SEQ ID NO:5 | 5'ATGGTGCATCTGTCCAGTGAGGAGAAGTCT3' |
| Primer 6 | SEQ ID NO:6 | 5'AGACTTCTCCTCACTGGACAGATGCACCAT3' |
| Primer 6m1 | SEQ ID NO:7 | 5'AGACTTCTCCTCACTGGACAGATGCACCAA3' |
| Primer 6m2 | SEQ ID NO:8 | 5'AGACTTCTCCTCACTGGACAGATGCACCAG3' |
| Primer 6m3 | SEQ ID NO:9 | 5'AGACTTCTCCTCACTGGACAGATGCACCAC3' |
| Primer 6m4 | SEQ ID NO:10 | 5'AGACTTCTCCTCACTGGACAGATGCACCCC3' |
| Primer 6m5 | SEQ ID NO:11 | 5'AGACTTCTCCTCACTGGACAGATGCACCGC3' |
| Primer 6m6 | SEQ ID NO:12 | 5'AGACTTCTCCTCACTGGACAGATGCACCTC3' |
| Primer 6m7 | SEQ ID NO:13 | 5'AGACTTCTCCTCACTGGACAGATGCACTAT3' |
| Primer 6m8 | SEQ ID NO:14 | 5'AGACTTCTCCTCACTGGACAGATGCATCAT3' |
| Primer 6m9 | SEQ ID NO:15 | 5'AGACTTCTCCTCACTGGACAGATGCTCCAT3' |
| Primer 6m10 | SEQ ID NO:16 | 5'AGACTTCTCCTCACTGGACAGATGTACCAT3' |
| Primer 7 | SEQ ID NO:17 | 5'GCTGCTGGTTGTCTACCCATGGACCC3' |
| Primer 8 | SEQ ID NO:18 | 5'GGGTCCATGGGTAGACAACCAGCAGC3' |
| Primer 8m1 | SEQ ID NO:19 | 5'GGGTCCATGGGTAGACAACCAGCAGA3' |
| Primer 8m2 | SEQ ID NO:20 | 5'GGGTCCATGGGTAGACAACCAGCAGG3' |
| Primer 8m3 | SEQ ID NO:21 | 5'GGGTCCATGGGTAGACAACCAGCAGT3' |
| Primer 8m4 | SEQ ID NO:22 | 5'GGGTCCATGGGTAGACAACCAGCACC3' |
| Primer 8m5 | SEQ ID NO:23 | 5'GGGTCCATGGGTAGACAACCAGCATC3' |
| Primer 8m6 | SEQ ID NO:24 | 5'GGGTCCATGGGTAGACAACCAGCAAC3' |
| Primer 8m7 | SEQ ID NO:25 | 5'GGGTCCATGGGTAGACAACCAGCTGC3' |
| Primer 8m8 | SEQ ID NO:26 | 5'GGGTCCATGGGTAGACAACCAGTAGC3' |
| Primer 8m9 | SEQ ID NO:27 | 5'GGGTCCATGGGTAGACAACCATCAGC3' |
| Primer 9 | SEQ ID NO:28 | 5'GATGCACCAT3' |
| Primer 10 | SEQ ID NO:29 | 5'TCACTGGACAGATGCACCAT3' |
| Primer 11 | SEQ ID NO:30 | 5'CAGTGACCGCAGACTTCTCCTCACTGGACAGATGCACCA3' |
| Primer 12 | SEQ ID NO:31 | 5'CCCCACAGGGCAGTGACCGCAGACTTCTCCTCACTGGACAGATGCACCA3' |
| Primer 13 | SEQ ID NO:32 | 5'GGGTCCATGG3' |
| Primer 14 | SEQ ID NO:33 | 5'GGGTCCATGGGTAGACAACC3' |
| Primer 15 | SEQ ID NO:34 | 5'GGGTCCATGGGTAGACAACCAGCAGCCTGC3' |
| Primer 16 | SEQ ID NO:35 | 5'GGGTCCATGGGTAGACAACCAGCAGCCTGCCCAGGGCCTC3' |
| Primer 17 | SEQ ID NO:36 | 5'GGGTCCATGGGTAGACAACCAGCAGCCTGCCCAGGGCCTCACCACCAACT3' |
| Primer 18 | SEQ ID NO:37 | 5'AACCAGCAGC3' |
| Primer 19 | SEQ ID NO:38 | 5'ATGGGTAGACAACCAGCAGC3' |
| Primer 20 | SEQ ID NO:39 | 5'CTCTGGGTCCATGGGTAGACAACCAGCAGC3' |
| Primer 21 | SEQ ID NO:40 | 5'CTCGAAGAACCTCTGGGTCCATGGGTAGACAACCAGCAGC3' |
| Primer 22 | SEQ ID NO:41 | 5'CCCCAAAGGACTCGAAGAACCTCTGGGTCCATGGGTAGACAACCAGCAGC3' |
| Primer 23 | SEQ ID NO:42 | 5'CAGTCACGACGTTGTAAAACGACGGCCAGT3' |

TABLE 93-continued

| Primer Designation | Sequence ID Number | Sequence |
|---|---|---|
| Primer 24 | SEQ ID NO:43 | 5'ACTGGCCGTCGTTTTACAACGTCGTGACTG3' |
| PCR Sequence 1 | SEQ ID NO:44 | 5'CGTGTATGCCACTTTGATATTACACCCATGAACGTGCTCATCGACGTGAACCCGCACAACGAGCT3' |
| PCR Sequence 2 | SEQ ID NO:45 | 5'CGTTGTGCGGGTTCACGTCGATGAGCACGTTCATGGGTGTAATATCAAAGTGGCATACACGAGCT3' |
| PCR Sequence 3 | SEQ ID NO:46 | 5'CGTGTATGCCACTTTGATATTACACCCGTGAACGTGCTCATCGACGTGAACCCGCACAACGAGCT3' |
| PCR Sequence 4 | SEQ ID NO:47 | 5'CGTTGTGCGGGTTCACGTCGATGAGCACGTTCACGGGTGTAATATCAAAGTGGCATACACGAGCT3' |
| PCR Sequence 5 (9211) | SEQ ID NO:48 | 5'CACTTTGATATTACACCCATG3' |
| PCR Sequence 6 (9212) | SEQ ID NO:49 | 5'CACTTTGATATTACACCCGTG3' |

What is claimed is:

1. A method for interrogating the identity of a specific base in a nucleic acid sample comprising:
   a) providing at least one nucleic acid probe and a sample suspected of containing at least one target nucleic acid, wherein said nucleic acid probe is substantially complementary to said target nucleic acid and comprises at least one predetermined nucleotide at an interrogation position, and wherein said target nucleic acid comprises at least one base to be identified;
   b) hybridizing said nucleic acid probe to said target nucleic acid to form a nucleic acid probe-target nucleic acid complex, wherein said predetermined nucleotide at said interrogation position is aligned with said base to be identified in said target nucleic acid so that base pairing may occur;
   c) treating said nucleic acid probe-target nucleic acid complex in the presence of inorganic pyrophosphate under conditions such that said probe is depolymerized and releases nucleotides; and
   d) detecting said released nucleotides thereby indicating the identity of said specific bases.

2. The method of claim 1, comprising the further step of identifying said base to be identified.

3. The method of claim 1, wherein said target nucleic acid is selected from the group consisting of deoxyribonucleic acid and ribonucleic acid.

4. The method of claim 3, further comprising a first probe, a second probe, a third probe and a fourth probe.

5. The method of claim 4, wherein said interrogation position of said first probe comprises a nucleic acid residue is selected from the group consisting of deoxyadenosine residues and adenosine residues, said interrogation position of said second probe comprises a nucleic acid residue selected from the group consisting of uridine residues and deoxythymidine residues, said interrogation position of said third probe comprises a nucleic acid residue selected from the group consisting of deoxyguanosine and guanosine residues, and said fourth nucleic acid probe comprises a nucleic acid residue selected from the group consisting of deoxycytosine and cytosine residues.

6. The method of claim 5, further comprising the step of determining the identity of said base to be identified.

7. The method of claim 2, wherein said nucleic acid probe further comprises a 5' end and a 3' end, said interrogation position being within ten bases of said 3' end.

8. The method of claim 2 wherein said treating said nucleic acid probe-target nucleic acid complex comprises:

a) providing a solution comprising said nucleic acid probe-nucleic acid target complex, adenosine 5' diphosphate, and pyrophosphate, said nucleic acid probe having a terminal nucleotide and terminal internucleotide phosphodiester bond, said terminal nucleotide covalently joined to said nucleic acid by said terminal internucleotide phosphodiester bond;

b) depolymerizing said nucleic acid probe-target nucleic acid complex at a nucleic acid probe terminal nucleotide by enzymatically cleaving said terminal internucleotide phosphodiester bond by addition of said pyrophosphate molecule to form a free nucleoside triphosphate molecule having a terminal 5' phosphate group according to the reaction:

$$probeNA_n + PP_i \rightarrow probeNA_{n-1} + XTP;$$

and c) enzymatically transferring terminal 5' phosphate groups from said nucleoside triphosphate molecules to adenosine 5'-diphosphate molecules to form adenosine 5'-triphosphate according to the following general reaction:

$$XTP^* + ADP \rightarrow XDP + ATP^*$$

wherein P* is the terminal 5' phosphate so transferred.

9. The method of claim 2, wherein the depolymerization is catalyzed by a polymerase selected from the group consisting of Klenow exo minus polymerase, Taq polymerase, AMV reverse transcriptase and MMLV reverse transcriptase.

10. The method of claim 8, wherein the detecting step further comprises quantitating said adenosine 5' triphosphate.

11. The method of claim 8, wherein the detecting step is selected from the group consisting of luciferase and NADH detection systems.

12. A method of discriminating between substantially identical nucleic acids in a sample comprising a) providing a sample suspected of containing at least two target nucleic acids, wherein said target nucleic acids comprise a region of identity having a mismatch of at least a single nucleotide at a predetermined position;

b) providing at least one nucleic acid probe, wherein said nucleic acid probe is substantially complementary to said target nucleic acid region of identity and comprises at least one nucleotide at an interrogation position, wherein said nucleotide at said interrogation position is complementary to said nucleotide at said predetermined position of said region of identity of said target nucleic acid;

c) hybridizing said nucleic acid probe to said target nucleic acid to form a nucleic acid probe-target nucleic acid complex, wherein said nucleotide at said interrogation position is aligned with said nucleotide at said predetermined position in said region of identity;

d) treating said nucleic acid probe-target nucleic acid complex in the presence of inorganic pyrophosphate under conditions such that said probe is depolymerized and releases nucleotides; and e) detecting said released nucleotides, thereby permitting discrimination between substantially identical nucleic acids in a sample.

13. The method of claim 12, wherein said target nucleic acid is selected from the group consisting of deoxyribonucleic acid and ribonucleic acid.

14. The method of claim 13, further comprising a first probe and a second probe.

15. The method of claim 14, wherein said first probe comprises a nucleotide at said interrogation position which is complementary to said first nucleic acid at said predetermined position and said second probe comprises a nucleotide at the interrogation position which is complementary to said second nucleic acid at said predetermined position.

16. The method of claim 13 wherein said nucleic acid probe further comprises a 5' end and a 3' end, said interrogation position being within ten bases of said 3' end.

17. The method of claim 13 wherein said treating said nucleic acid probe-nucleic acid target complex comprises:

a) providing a solution comprising said nucleic acid probe-nucleic acid target complex, adenosine 5' diphosphate, and pyrophosphate, said nucleic acid probe having a terminal nucleotide and terminal internucleotide phosphodiester bond, said terminal nucleotide covalently joined to said nucleic acid by said terminal internucleotide phosphodiester bond;

b) depolymerizing said nucleic acid probe-target nucleic acid complex at a nucleic acid probe terminal nucleotide by enzymatically cleaving said terminal internucleotide phosphodiester bond by addition of said pyrophosphate molecule to form a free nucleoside triphosphate molecule having a terminal 5' phosphate group according to the reaction:

$$probeNA_n + PP_i \rightarrow probeNA_{n-1} + XTP;$$

and c) enzymatically transferring terminal 5' phosphate groups from said nucleoside triphosphate molecules to adenosine 5'-diphosphate molecules to form adenosine 5'-triphosphate according to the following general reaction:

$$XTP^* + ADP \rightarrow XDP + ATP^*$$

wherein P* is the terminal 5' phosphate so transferred;

d) repeating steps a–c.

18. The method of claim 17, wherein the depolymerization is catalyzed by a polymerase selected from the group consisting of Klenow exo minus polymerase, Taq polymerase, AMV reverse transcriptase and MMLV reverse transcriptase.

19. The method of claim 17, wherein the detecting step further comprises quantitating said adenosine 5' triphosphate.

20. The method of claim 17, wherein the detecting step is selected from the group consisting of luciferase and NADH detection systems.

21. The method of claim 12, wherein the first and second nucleic acids are alleles.

22. The method of claim 12, wherein the first nucleic acid is from a first species and wherein the second nucleic acid is from a second species.

23. A method for detecting a nucleic acid comprising:

a) providing at least one nucleic acid probe and a sample suspected of containing a target nucleic acid, wherein said nucleic acid probe is substantially complementary to said target nucleic acid;

b) hybridizing said nucleic acid probe to said target nucleic acid to form a nucleic acid probe-target nucleic acid complex;

c) treating said nucleic acid probe-target nucleic acid complex in the presence of inorganic pyrophosphate under conditions that allow said nucleic acid probe to be depolymerized to release nucleotides; and d) detecting said released nucleotides thereby indicating the presence or absence of said target nucleic acid.

24. The method of claim 23, wherein said target nucleic acid is selected from the group consisting of deoxyribonucleic acid and ribonucleic acid.

25. The method of claim 23, wherein said nucleic acid probe is selected from the group consisting of deoxyribonucleic acid and ribonucleic acid.

26. The method of claim 23, wherein said treating said nucleic acid probe-nucleic acid target complex comprises:

a) providing a solution comprising said nucleic acid probe-nucleic acid target complex, adenosine 5' diphosphate, and pyrophosphate, said nucleic acid probe having a terminal nucleotide and terminal internucleotide phosphodiester bond, said terminal nucleotide covalently joined to said nucleic acid by said terminal internucleotide phosphodiester bond;

b) depolymerizing said nucleic acid probe-target nucleic acid complex at said nucleic acid probe terminal nucleotide by enzymatically cleaving said terminal internucleotide phosphodiester bond by addition of said pyrophosphate molecule to form a free nucleoside triphosphate molecule having a terminal 5' phosphate group according to the reaction:

$$\text{probeNA}_n + \text{PP}_i \rightarrow \text{probeNA}_{n-1} + \text{XTP};$$

and c) enzymatically transferring said terminal 5' phosphate groups from said nucleoside triphosphate molecules to adenosine 5'-diphosphate molecules to form adenosine 5'-triphosphate according to the following general reaction:

$$\text{XTP}^* + \text{ADP} \rightarrow \text{XDP} + \text{ATP}^*,$$

wherein P* is the terminal 5' phosphate so transferred.

27. The method of claim 23 wherein the depolymerization is catalyzed by a polymerase selected from the group consisting of Klenow fragment, Klenow exo minus polymerase, DNA polymerase I, Taq polymerase, Tne polymerase, Tth polymerase, AMV reverse transcriptase and MMLV reverse transcriptase.

28. The method of claim 26 wherein the detecting step further comprises quantitating said adenosine 5' triphosphate.

29. The method of claim 26 wherein the detecting step is selected from the group consisting of luciferase and NADH detection systems.

30. The method of claim 23, wherein said probe nucleic acid further comprises a 5' end and a 3' end, and said target nucleic acid further comprises a region of complementarity to said nucleic acid probe, said region of complementarity having a first end defined by the 3' end of said nucleic acid probe and a second end defined by said 5' of said nucleic acid probe, said region of complementarity having therein a lesion between said first end and said second end and said nucleic acid probe.

31. The method of claim 30, wherein said lesion comprises an insertion mutation.

32. The method of claim 30, wherein said lesion comprises a deletion mutation.

33. The method of claim 30, wherein said lesion is within ten bases of said 3' end of said nucleic acid probe.

* * * * *

SEQUENCE LISTING

<160> NUMBER OF SEQ ID NOS: 49

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:
      complementary to a segment of the coding region of kanamycin RNA

<400> SEQUENCE: 1
gcaacgctac ctttgccatg tttc                                         24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:
      complementary to a segment of the coding region of kanamycin RNA,
      altered at 3' terminal base

<400> SEQUENCE: 2
gcaacgctac ctttgccatg tttg                                         24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:
      complementary to a segment of the coding region of kanamycin RNA,
      altered at the 3' terminal base

<400> SEQUENCE: 3
gcaacgctac ctttgccatg ttta                                         24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:
      complementary to a segment of the coding region of kanamycin RNA,
      altered at the 3' terminal base

```
<400> SEQUENCE: 4
gcaacgctac ctttgccatg tttt                                              24

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:  nucleic
      acid probe with same sequence as a portion of globin mRNA

<400> SEQUENCE: 5
atggtgcatc tgtccagtga ggagaagtct                                        30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:  nucleic
      acid probe with sequence complementary to a portion of globin
      mRNA

<400> SEQUENCE: 6
agacttctcc tcactggaca gatgcaccat                                        30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:  3'
      terminus-modified

<400> SEQUENCE: 7
agacttctcc tcactggaca gatgcaccaa                                        30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: 3'
      terminus-modified  nucleic acid probe with sequence complementary
      to a portion of globin mRNA

<400> SEQUENCE: 8
agacttctcc tcactggaca gatgcaccag                                        30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:  3'
      terminus-modified  nucleic acid probe with sequence complementary
      to a portion of globin mRNA

<400> SEQUENCE: 9
agacttctcc tcactggaca gatgcaccac                                        30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:
``` modification of base penultimate to 3' terminus of nucleic acid
        probe with sequence complementary to a portion of globin mRNA

<400> SEQUENCE: 10
agacttctcc tcactggaca gatgcacccc                                              30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:
        modification of base penultimate to 3' terminus of nucleic acid
        probe with sequence complementary to a portion of globin mRNA

<400> SEQUENCE: 11
agacttctcc tcactggaca gatgcaccgc                                              30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:
        modification of base penultimate to 3' terminus of nucleic acid
        probe with sequence complementary to a portion of globin mRNA

<400> SEQUENCE: 12
agacttctcc tcactggaca gatgcacctc                                              30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:  mismatch
        at position 3 from 3' end in nucleic acid probe with sequence
        complementary to a portion of globin mRNA

<400> SEQUENCE: 13
agacttctcc tcactggaca gatgcactat                                              30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:  mismatch
        at position 4 from 3' end in nucleic acid probe with sequence
        complementary to a portion of globin mRNA

<400> SEQUENCE: 14
agacttctcc tcactggaca gatgcatcat                                              30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:  mismatch
        at position 5 from 3' end in nucleic acid probe with sequence
        complementary to a portion of globin mRNA

<400> SEQUENCE: 15
agacttctcc tcactggaca gatgctccat                                              30

<210> SEQ ID NO 16

```
<211> LENGTH: 30
<212> TYPE: DNA
<213> ORGANISM: Artificial Sequence
<220> FEATURE:
<223> OTHER INFORMATION: Description of Artificial Sequence:    mismatch
      at position 6 from 3' end in nucleic acid probe with sequence
      complementary to a portion of globin mRNA

<400> SEQUENCE: 16
agacttctcc tcactggaca gatgtaccat                                              30

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence:   nucleic
      acid probe with same sequence as a portion of globin mRNA

<400> SEQUENCE: 17
gctgctggtt gtctacccat ggaccc                                                  26

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence:   nucleic
      acid probe with sequence complementary to a portion of globin mRNA

<400> SEQUENCE: 18
gggtccatgg gtagacaacc agcagc                                                  26

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence:   3'
      terminus-modified

<400> SEQUENCE: 19
gggtccatgg gtagacaacc agcaga                                                  26

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence:   3'
      terminus-modified

<400> SEQUENCE: 20
gggtccatgg gtagacaacc agcagg                                                  26

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence:   3'
      terminus-modified

<400> SEQUENCE: 21
gggtccatgg gtagacaacc agcagt                                                  26

<210> SEQ ID NO 22
```

-continued

```
<211> LENGTH: 26
<212> TYPE: DNA
<213> ORGANISM: Artificial Sequence
<220> FEATURE:
<223> OTHER INFORMATION: Description of Artificial Sequence:
      modification of base penultimate to 3' terminus of nucleic acid
      probe with sequence complementary to a portion of globin mRNA

<400> SEQUENCE: 22
gggtccatgg gtagacaacc agcacc                                          26

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence:
      modification of base penultimate to 3' terminus of nucleic acid
      probe with sequence complementary to a portion of globin mRNA

<400> SEQUENCE: 23
gggtccatgg gtagacaacc agcatc                                          26

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence:
      modification of base penultimate to 3' terminus of nucleic acid
      probe with sequence complementary to a portion of globin mRNA

<400> SEQUENCE: 24
gggtccatgg gtagacaacc agcaac                                          26

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence:  mismatch
      at position 3 from 3' end in nucleic acid probe with sequence
      complementary to a portion of globin mRNA

<400> SEQUENCE: 25
gggtccatgg gtagacaacc agctgc                                          26

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence:  mismatch
      at position 4 from 3' end in nucleic acid probe with sequence
      complementary to a portion of globin mRNA

<400> SEQUENCE: 26
gggtccatgg gtagacaacc agtagc                                          26

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence:  mismatch
      at position 5 from 3' end in nucleic acid probe with sequence
      complementary to a portion of globin mRNA

<400> SEQUENCE: 27
```
gggtccatgg gtagacaacc atcagc                    26

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence: nucleic
      acid probe for globin mRNA, identical 3' ends but length of 10

<400> SEQUENCE: 28
gatgcaccat                                       10

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: nucleic
      acid probe for globin mRNA, identical 3' ends but length of 20

<400> SEQUENCE: 29
tcactggaca gatgcaccat                            20

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence:  nucleic
      acid probe for globin mRNA, identical 3' ends but length of 40

<400> SEQUENCE: 30
cagtgaccgc agacttctcc tcactggaca gatgcacca       39

<210> SEQ ID NO 31
<211> LENGTH: 49
<212> TYPE: DNA
<213> ORGANISM: Artificial Sequence
<220> FEATURE:
<223> OTHER INFORMATION: Description of Artificial Sequence:  nucleic
      acid probe for globin mRNA, identical 3' ends but length of 50

<400> SEQUENCE: 31
ccccacaggg cagtgaccgc agacttctcc tcactggaca gatgcacca    49

<210> SEQ ID NO 32
<211> LENGTH: 10
<212> TYPE: DNA
<213> ORGANISM: Artificial Sequence
<220> FEATURE:
<223> OTHER INFORMATION: Description of Artificial Sequence:  nucleic
      acid probe for globin mRNA, identical 5' end but length of 10

<400> SEQUENCE: 32
gggtccatgg                                       10

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence:  nucleic
      acid probe for globin mRNA, identical 5' end but length of 20

<400> SEQUENCE: 33

-continued gggtccatgg gtagacaacc                                      20

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence:   nucleic
      acid probe for globin mRNA, identical 5' end but length of 30

<400> SEQUENCE: 34
gggtccatgg gtagacaacc agcagcctgc                           30

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence:   nucleic
      acid probe for globin mRNA, identical 5' end but length of 40

<400> SEQUENCE: 35
gggtccatgg gtagacaacc agcagcctgc ccagggcctc                40

<210> SEQ ID NO 36
<211> LENGTH: 50
<212> TYPE: DNA
<213> ORGANISM: Artificial Sequence
<220> FEATURE:
<223> OTHER INFORMATION: Description of Artificial Sequence: nucleic
      acid probe for globin mRNA, identical 5' end but length of 50

<400> SEQUENCE: 36
gggtccatgg gtagacaacc agcagcctgc ccagggcctc accaccaact     50

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: nucleic
      acid probe for globin mRNA

<400> SEQUENCE: 37
aaccagcagc                                                 10

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:   nucleic
      acid probe for globin mRNA

<400> SEQUENCE: 38
atgggtagac aaccagcagc                                      20

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence:   nucleic
      acid probe for globin mRNA

<400> SEQUENCE: 39
ctctgggtcc atgggtagac aaccagcagc                           30

```
<210> SEQ ID NO 40
<211> LENGTH: 40
<212> TYPE: DNA
<213> ORGANISM: Artificial Sequence
<220> FEATURE:
<223> OTHER INFORMATION: Description of Artificial Sequence:  nucleic
      acid probe for globin mRNA

<400> SEQUENCE: 40
ctcgaagaac ctctgggtcc atgggtagac aaccagcagc                               40

<210> SEQ ID NO 41
<211> LENGTH: 50
<212> TYPE: DNA
<213> ORGANISM: Artificial Sequence
<220> FEATURE:
<223> OTHER INFORMATION: Description of Artificial Sequence:  nucleic
      acid probe for globin mRNA

<400> SEQUENCE: 41
ccccaaagga ctcgaagaac ctctgggtcc atgggtagac aaccagcagc                    50

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: beta-gal
      gene nucleic acid probe

<400> SEQUENCE: 42
cagtcacgac gttgtaaaac gacggccagt                                          30

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: beta-gal
      gene nucleic acid probe

<400> SEQUENCE: 43
actggccgtc gttttacaac gtcgtgactg                                          30

<210> SEQ ID NO 44
<211> LENGTH: 65
<212> TYPE: DNA
<213> ORGANISM: Artificial Sequence
<220> FEATURE:
<223> OTHER INFORMATION: Description of Artificial Sequence:  synthetic
      cytomegalovirus nucleic acid target sequence

<400> SEQUENCE: 44
cgtgtatgcc actttgatat tacacccatg aacgtgctca tcgacgtgaa cccgcacaac         60
gagct                                                                     65

<210> SEQ ID NO 45
<211> LENGTH: 65
<212> TYPE: DNA
<213> ORGANISM: Artificial Sequence
<220> FEATURE:
<223> OTHER INFORMATION: Description of Artificial Sequence:  synthetic
      cytomegalovirus nucleic acid target sequenc

<400> SEQUENCE: 45
```

-continued

```
cgttgtgcgg gttcacgtcg atgagcacgt tcatgggtgt aatatcaaag tggcatacac    60
gagct                                                                65

<210> SEQ ID NO 46
<211> LENGTH: 65
<212> TYPE: DNA
<213> ORGANISM: Artificial Sequence
<220> FEATURE:
<223> OTHER INFORMATION: Description of Artificial Sequence:  mutated
      synthetic cytomegalovirus nucleic acid target
      sequenc

<400> SEQUENCE: 46
cgtgtatgcc actttgatat tacacccgtg aacgtgctca tcgacgtgaa cccgcacaac    60
gagct                                                                65

<210> SEQ ID NO 47
<211> LENGTH: 65
<212> TYPE: DNA
<213> ORGANISM: Artificial Sequence
<220> FEATURE:
<223> OTHER INFORMATION: Description of Artificial Sequence:  mutated

<400> SEQUENCE: 47
cgttgtgcgg gttcacgtcg atgagcacgt tcacgggtgt aatatcaaag tggcatacac    60
gagct                                                                65

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence:
      cytomegalovirus nucleic acid probe

<400> SEQUENCE: 48
cactttgata ttacacccat g                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence:  mutated
      cytomegalovirus nucleic acid probe

<400> SEQUENCE: 49
cactttgata ttacacccgt g                                              21
```